US010071156B2

(12) United States Patent
Ma et al.

(10) Patent No.: US 10,071,156 B2
(45) Date of Patent: *Sep. 11, 2018

(54) AQUEOUS GEL FORMULATIONS CONTAINING IMMUNE RESPONSE MODIFIERS

(71) Applicant: 3M INNOVATIVE PROPERTIES COMPANY, Saint Paul, MN (US)

(72) Inventors: David Q. Ma, South Saint Paul, MN (US); Christopher S. Perman, Brooklyn Park, MN (US); Raymond D. Skwierczynski, Andover, MA (US); John C. Hedenstrom, Saint Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/971,230

(22) Filed: Dec. 16, 2015

(65) Prior Publication Data

US 2016/0101173 A1  Apr. 14, 2016

Related U.S. Application Data

(62) Division of application No. 11/883,665, filed as application No. PCT/US2006/004201 on Feb. 3, 2006, now Pat. No. 9,248,127.

(60) Provisional application No. 60/650,030, filed on Feb. 4, 2005.

(51) Int. Cl.
| | | |
|---|---|---|
| *A01N 43/42* | (2006.01) |
| *A61K 31/44* | (2006.01) |
| *A01N 43/50* | (2006.01) |
| *A61K 31/415* | (2006.01) |
| *A61K 39/39* | (2006.01) |
| *A61K 9/00* | (2006.01) |
| *A61K 31/4745* | (2006.01) |
| *A61K 47/10* | (2017.01) |
| *A61K 9/06* | (2006.01) |
| *A61K 47/20* | (2006.01) |
| *A61M 31/00* | (2006.01) |
| *A61K 47/12* | (2006.01) |
| *A61K 47/32* | (2006.01) |
| *A61K 47/36* | (2006.01) |

(52) U.S. Cl.
CPC ............ *A61K 39/39* (2013.01); *A61K 9/0034* (2013.01); *A61K 9/06* (2013.01); *A61K 31/4745* (2013.01); *A61K 47/10* (2013.01); *A61K 47/20* (2013.01); *A61M 31/007* (2013.01); *A61K 47/12* (2013.01); *A61K 47/32* (2013.01); *A61K 47/36* (2013.01)

(58) Field of Classification Search
USPC .......................... 424/434; 514/293, 303, 292
See application file for complete search history.

(56) References Cited

U.S. PATENT DOCUMENTS

| | | |
|---|---|---|
| 3,314,941 A | 4/1967 | Lundquist, Jr. et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |

(Continued)

FOREIGN PATENT DOCUMENTS

| | | |
|---|---|---|
| AU | 2004220534 A1 | 9/2004 |
| AU | 2004229478 A1 | 10/2004 |

(Continued)

OTHER PUBLICATIONS

Lacarrubba et al. Advances in the use of topical imiquimod to treat dermatologic disorders Ther Clin Risk Manag. Feb. 2008; 4(1): 87-97).*
(Cação, et al. "Failure of imiquimod 5% cream to prevent recurrence of surgically excised trunk keloids." Dermatologic Surgery 35.4 (2009): 629-633).*
Berge et al., J. Pharm. Sciences, 66, 1-19 (1977).
International Search Report and Written Opinion for PCT/US2006/004201 dated Jan. 30, 2007.
International Preliminary Report on Patentability for PCT/US2006/004201 dated Aug. 16, 2007.
[No Author Listed] "Aqueous cream." Wikipedia. Available at http://en.wikipedia.org/wiki/Aqueous_cream. Last accessed Sep. 15, 2010.

(Continued)

*Primary Examiner* — Layla Soroush

(57) ABSTRACT

Aqueous gel formulations, including an immune response modifier (IRM), such as those chosen from imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, imidazotetrahydronaphthyridine amines, oxazoloquinoline amines, thiazoloquinoline amines, oxazolopyridine amines, thiazolopyridine amines, oxazolonaphthyridine amines, thiazolonaphthyridine amines, pyrazolopyridine amines, pyrazoloquinoline amines, tetrahydropyrazoloquinoline amines, pyrazolonaphthyridine amines, tetrahydropyrazolonaphthyridine amines, and 1H-imidazo dimers fused to pyridine amines, quinoline amines, tetrahydroquinoline amines, naphthyridine amines, or tetrahydronaphthyridine amines, are provided. Methods of use and kits are also provided.

24 Claims, No Drawings

(56) References Cited

U.S. PATENT DOCUMENTS

| | | |
|---|---|---|
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman et al. |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster et al. |
| 5,268,376 A | 12/1993 | Gerster |
| 5,274,113 A | 12/1993 | Kang et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A | 1/1996 | Lindstrom et al. |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman et al. |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,017,537 A | 1/2000 | Alexander ............ A61K 39/21 424/184.1 |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomei et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |

(56) References Cited

U.S. PATENT DOCUMENTS

| | | |
|---|---|---|
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom ........ A61K 9/0014 514/292 |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun ................ A61K 39/39 424/184.1 |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0058673 A1 | 3/2005 | Scholz et al. ................ 424/401 |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2006/0188913 A1 | 8/2006 | Krieg et al. ..................... 435/6 |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |

(56) References Cited

U.S. PATENT DOCUMENTS

| | | | |
|---|---|---|---|
| 2007/0099901 | A1 | 5/2007 | Krepski et al. |
| 2007/0155767 | A1 | 7/2007 | Radmer et al. |
| 2007/0166384 | A1 | 7/2007 | Zarraga .................. 424/486 |
| 2007/0167476 | A1 | 7/2007 | Kshirsagar et al. |
| 2007/0208052 | A1 | 9/2007 | Prince et al. |
| 2007/0213356 | A1 | 9/2007 | Merrill et al. |
| 2007/0219196 | A1 | 9/2007 | Krepski et al. |
| 2007/0219228 | A1 | 9/2007 | Niwas et al. |
| 2007/0259881 | A1 | 11/2007 | Dellaria et al. |
| 2007/0259907 | A1 | 11/2007 | Prince |
| 2007/0287725 | A1 | 12/2007 | Miser et al. |
| 2007/0292456 | A1 | 12/2007 | Hammerbeck et al. |
| 2008/0015184 | A1 | 1/2008 | Kshirsagar et al. |
| 2008/0070907 | A1 | 3/2008 | Griesgraber et al. |
| 2008/0085895 | A1 | 4/2008 | Griesgraber et al. |
| 2008/0114019 | A1 | 5/2008 | Kshirsagar et al. |
| 2008/0119508 | A1 | 5/2008 | Slade et al. |
| 2008/0207674 | A1 | 8/2008 | Stoesz et al. |
| 2008/0269192 | A1 | 10/2008 | Griesgraber et al. |
| 2008/0306252 | A1 | 12/2008 | Crooks et al. |
| 2008/0312434 | A1 | 12/2008 | Lindstrom et al. |
| 2008/0318998 | A1 | 12/2008 | Prince et al. |
| 2009/0005371 | A1 | 1/2009 | Rice et al. |
| 2009/0017076 | A1 | 1/2009 | Miller et al. |
| 2009/0018122 | A1 | 1/2009 | Lindstrom et al. |
| 2009/0023722 | A1 | 1/2009 | Coleman et al. |
| 2009/0029988 | A1 | 1/2009 | Kshirsagar et al. |
| 2009/0030030 | A1 | 1/2009 | Bonk et al. |
| 2009/0030031 | A1 | 1/2009 | Kshirsagar et al. |
| 2009/0042925 | A1 | 2/2009 | Kshirsagar et al. |
| 2009/0062272 | A1 | 3/2009 | Bonk et al. |
| 2009/0062328 | A1 | 3/2009 | Kshirsagar et al. |
| 2009/0069299 | A1 | 3/2009 | Merrill et al. |
| 2009/0069314 | A1 | 3/2009 | Kshirsagar et al. |
| 2009/0075980 | A1 | 3/2009 | Hays et al. |
| 2009/0099161 | A1 | 4/2009 | Rice et al. |
| 2009/0105295 | A1 | 4/2009 | Kshirsagar et al. |
| 2009/0124611 | A1 | 5/2009 | Hays et al. |
| 2009/0163533 | A1 | 6/2009 | Hays et al. |
| 2009/0176821 | A1 | 7/2009 | Kshirsagar et al. |
| 2009/0240055 | A1 | 9/2009 | Krepski et al. |
| 2009/0253695 | A1 | 10/2009 | Kshirsagar et al. |
| 2009/0270443 | A1 | 10/2009 | Stoermer et al. |
| 2009/0318435 | A1 | 12/2009 | Hays et al. |
| 2010/0113565 | A1 | 5/2010 | Gorden et al. |
| 2010/0240693 | A1 | 9/2010 | Lundquist, Jr. et al. |

FOREIGN PATENT DOCUMENTS

| | | | | |
|---|---|---|---|---|
| AU | 2004264336 | A1 | 2/2005 | |
| AU | 2004268625 | A1 | 3/2005 | |
| AU | 2002239547 | B2 | 11/2006 | |
| CA | 2044087 | A1 | 12/1991 | |
| CA | 2158996 | A1 | 10/1994 | |
| CN | 1354663 | A | 6/2002 | |
| EP | 0 145 340 | A2 | 6/1985 | |
| EP | 0 223 420 | A1 | 5/1987 | |
| EP | 0 310 950 | A1 | 4/1989 | |
| EP | 0 385 630 | A2 | 9/1990 | |
| EP | 0 389 302 | A1 | 9/1990 | |
| EP | 0 394 026 | A1 | 10/1990 | |
| EP | 0 425 306 | A2 | 5/1991 | |
| EP | 0 510 260 | A2 | 10/1992 | |
| EP | 0 556 008 | A1 | 8/1993 | |
| EP | 0 645 389 | A1 | 3/1995 | |
| EP | 0 778 277 | A1 | 6/1997 | |
| EP | 0 894 797 | A1 | 2/1999 | |
| EP | 1 082 960 | A2 | 3/2001 | |
| EP | 1 097 709 | A2 | 5/2001 | |
| EP | 1 104 764 | A1 | 6/2001 | |
| EP | 1 145 340 | A2 | 10/2001 | |
| EP | 1 256 582 | A1 | 11/2002 | |
| EP | 1 341 791 | B1 | 9/2003 | |
| EP | 1 495 758 | A2 | 1/2005 | |
| HU | 34479 | A2 | 3/1985 | |
| HU | 210051 | A2 | 6/1991 | |
| HU | 218950 | A2 | 9/1995 | |
| IL | 73534 | A | 12/1990 | |
| JP | 53050197 | A | 5/1978 | |
| JP | 63010787 | A | 1/1988 | |
| JP | 1180156 | A | 7/1989 | |
| JP | 4066571 | A | 3/1992 | |
| JP | 4327587 | A | 11/1992 | |
| JP | 5286973 | A | 11/1993 | |
| JP | 9208584 | A | 8/1997 | |
| JP | 11222432 | A | 8/1999 | |
| JP | 2000247884 | A | 9/2000 | |
| NZ | 545412 | A | 12/2008 | |
| RU | 2076105 | C1 | 3/1997 | |
| RU | 2127273 | C1 | 3/1999 | |
| RU | 2221798 | C2 | 1/2004 | |
| WO | WO-91/06682 | A1 | 5/1991 | |
| WO | WO-92/06093 | A1 | 4/1992 | |
| WO | WO-92/15581 | A1 | 9/1992 | |
| WO | WO-92/15582 | A1 | 9/1992 | |
| WO | WO-93/05042 | A1 | 3/1993 | |
| WO | WO-93/09119 | A1 | 5/1993 | |
| WO | WO-93/20847 | A1 | 10/1993 | |
| WO | WO-94/10171 | A1 | 5/1994 | |
| WO | WO-95/02597 | A1 | 1/1995 | |
| WO | WO-95/02598 | A1 | 1/1995 | |
| WO | WO-96/11199 | A1 | 4/1996 | |
| WO | WO-96/21663 | A1 | 7/1996 | |
| WO | WO-97/48703 | A1 | 12/1997 | |
| WO | WO-97/48704 | A1 | 12/1997 | |
| WO | WO-98/17279 | A1 | 4/1998 | |
| WO | WO-98/30562 | A1 | 7/1998 | |
| WO | WO-98/48805 | A1 | 11/1998 | |
| WO | WO-98/50547 | A2 | 11/1998 | |
| WO | WO-98/54226 | A1 | 12/1998 | |
| WO | WO-99/18105 | A1 | 4/1999 | |
| WO | WO-99/29693 | A1 | 6/1999 | |
| WO | WO-00/06577 | A1 | 2/2000 | |
| WO | WO-00/09506 | A1 | 2/2000 | |
| WO | WO-00/19987 | A1 | 4/2000 | |
| WO | WO-00/40228 | A2 | 7/2000 | |
| WO | WO-00/47719 | A2 | 8/2000 | |
| WO | WO-00/75304 | A1 | 12/2000 | |
| WO | WO-00/76505 | A1 | 12/2000 | |
| WO | WO-00/76518 | A1 | 12/2000 | |
| WO | WO-00/76519 | A1 | 12/2000 | |
| WO | WO-01/34709 | A1 | 5/2001 | |
| WO | WO-01/51486 | A2 | 7/2001 | |
| WO | WO-01/55439 | A1 | 8/2001 | |
| WO | WO-01/58900 | A1 | 8/2001 | |
| WO | WO-01/74343 | A2 | 10/2001 | |
| WO | WO-01/74821 | A1 | 10/2001 | |
| WO | WO 0174343 | A2 | 10/2001 | ......... A61K 31/4745 |
| WO | WO 2001/97795 | | 12/2001 | |
| WO | WO-02/07725 | A1 | 1/2002 | |
| WO | WO-02/22809 | A2 | 3/2002 | |
| WO | WO-02/24225 | A1 | 3/2002 | |
| WO | WO-02/36592 | A1 | 5/2002 | |
| WO | WO-02/46188 | A2 | 6/2002 | |
| WO | WO-02/46189 | A2 | 6/2002 | |
| WO | WO-02/46190 | A2 | 6/2002 | |
| WO | WO-02/46191 | A2 | 6/2002 | |
| WO | WO-02/46192 | A2 | 6/2002 | |
| WO | WO-02/46193 | A2 | 6/2002 | |
| WO | WO-02/46194 | A2 | 6/2002 | |
| WO | WO-02/46749 | A2 | 6/2002 | |
| WO | WO-02/85905 | A1 | 10/2002 | |
| WO | WO-02/102377 | A1 | 12/2002 | |
| WO | WO-03/008421 | A1 | 1/2003 | |
| WO | WO-03/009852 | A1 | 2/2003 | |
| WO | WO-03/20889 | A2 | 3/2003 | |
| WO | WO-03/43572 | A1 | 5/2003 | |
| WO | WO-03/45391 | A1 | 6/2003 | |
| WO | WO-03/45494 | A2 | 6/2003 | |
| WO | WO-03/45929 | A1 | 6/2003 | |
| WO | WO-03/50117 | A1 | 6/2003 | |
| WO | WO-03/50118 | A1 | 6/2003 | |
| WO | WO-03/50119 | A2 | 6/2003 | |
| WO | WO-03/50121 | A1 | 6/2003 | |

(56) References Cited

FOREIGN PATENT DOCUMENTS

| | | |
|---|---|---|
| WO | WO-03/77944 A1 | 9/2003 |
| WO | WO-03/80114 A2 | 10/2003 |
| WO | WO-03/86280 A2 | 10/2003 |
| WO | WO-03/86350 A1 | 10/2003 |
| WO | WO-03/89602 A2 | 10/2003 |
| WO | WO-03/97641 A2 | 11/2003 |
| WO | WO-03/101949 A2 | 12/2003 |
| WO | WO-03/103584 A2 | 12/2003 |
| WO | WO-2004/009593 A1 | 1/2004 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO 2005/018551 A2 | 3/2005 |
| WO | WO-2005/018555 A2 | 3/2005 |
| WO | WO 2005/018556 A2 | 3/2005 |
| WO | WO 2005/020999 A1 | 3/2005 |
| WO | WO-2005/023190 A2 | 3/2005 |
| WO | WO-2005/025614 A3 | 3/2005 |
| WO | WO-2005/029037 A2 | 3/2005 |
| WO | WO 2005/032484 A2 | 4/2005 |
| WO | WO-2005/041891 A2 | 5/2005 |
| WO | WO 2005/048933 A2 | 6/2005 |
| WO | WO 2005/048945 A2 | 6/2005 |
| WO | WO-2005/049076 A1 | 6/2005 |
| WO | WO 2005/051317 A2 | 6/2005 |
| WO | WO 2005/051324 A2 | 6/2005 |
| WO | WO-2005/054237 A2 | 6/2005 |
| WO | WO-2005/054238 A1 | 6/2005 |
| WO | WO-2005/065678 A1 | 7/2005 |
| WO | WO 2005/066169 A2 | 7/2005 |
| WO | WO 2005/066170 A1 | 7/2005 |
| WO | WO 2005/066172 A1 | 7/2005 |
| WO | WO-2005/067500 A2 | 7/2005 |
| WO | WO 2005/076783 A2 | 8/2005 |
| WO | WO 2005/079195 A2 | 9/2005 |
| WO | WO 2005/094531 A2 | 10/2005 |
| WO | WO-2005/110013 A2 | 11/2005 |
| WO | WO-2005/123079 A2 | 12/2005 |
| WO | WO-2005/123080 A2 | 12/2005 |
| WO | WO-2006/004737 A2 | 1/2006 |
| WO | WO-2006/009826 A1 | 1/2006 |
| WO | WO-2006/009832 A1 | 1/2006 |
| WO | WO-2006/026760 A2 | 3/2006 |
| WO | WO-2006/028451 A1 | 3/2006 |
| WO | WO-2006/028545 A2 | 3/2006 |
| WO | WO-2006/028962 A2 | 3/2006 |
| WO | WO-2006/029115 A2 | 3/2006 |
| WO | WO-2006/031878 A2 | 3/2006 |
| WO | WO-2006/038923 A2 | 4/2006 |
| WO | WO-2006/063072 A2 | 6/2006 |
| WO | WO-2006/063152 A2 | 6/2006 |
| WO | WO-2006/065280 A2 | 6/2006 |
| WO | WO 2006/073939 | 7/2006 |
| WO | WO-2006/073940 A2 | 7/2006 |
| WO | WO-2006/074003 A2 | 7/2006 |
| WO | WO-2006/074045 A2 | 7/2006 |
| WO | WO-2006/083440 A2 | 8/2006 |
| WO | WO 2006/084073 | 8/2006 |
| WO | WO-2006/084251 A2 | 8/2006 |
| WO | WO-2006/086449 A2 | 8/2006 |
| WO | WO-2006/086633 A2 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/002646 A2 | 1/2008 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-60.
Agrawal et al., Synthetic agonists of Toll-like receptors 7, 8 and 9. Biochem Soc Trans. Dec. 2007;35(Pt 6):1461-7.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct. 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon A gene requires cooperation between multiple binding factors in the interferon alpha promoter region. J Biol Chem. Nov. 15, 1993;268(32):24032-40.
Auerbach et al., Erythema nodosum following a jellyfish sting. J Emerg Med. Nov.-Dec. 1987;5(6):487-91.
Auwers, [Uber die Isomerie-Verhaltnisse in der Pyrazol-Reihe. Berichte. VI.] 1926;601-607. German.
Bachman et al., Synthesis of substituted quinolylamines. Derivatives of 4-amino-7-chloroquinoline. J Org Chem. 1950;15(6):1278-84.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with Porphyromonas gingivalis and induced alveolar bone loss in immunocompetent and severe combined immunodeficient mice. Arch Oral Biol. Dec. 1994;39(12):1035-40.

(56) References Cited

OTHER PUBLICATIONS

Baldwin et al., Amino Acid Synthesis via Ring Opening of N-Sulphonyl Aziridine-2-Carboxylate Esters with Organometallic Reagents. Tetrahedron. 1993;49:6309-30.
Baranov et al., Imidazo[4-5c]quinolines. In Chemical Abstracts. 1976;85:637. Abstract 94362z.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (−)-Methadone from D-(−)-Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-68.
Berenyi et al., Ring transformation of condensed dihyrdo-astriazines. J Heterocyclic Chem. 1981;18:1537-40.
Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.
Bertino et al., Principles of Cancer Therapy. Cecil Textbook of Medicine. Goldman et al., eds. 21th Ed. W.B. Saunders Company. 2000:1:1060-74.
Beutler et al., Tumor necrosis factor in the pathogenesis of infectious diseases. Crit Care Med. Oct. 1993;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.
Bishop et al., Molecular mechanisms of B lymphocyte activation by the immune response modifier R-848. J Immunol. Nov. 15, 2000;165(10):5552-7.
Bitterman-Deutsch et al., [Brown spider bite]. Harefuah. Sep. 1990;119(5-6):137-9. Hebrew.
Booth et al., Dapsone suppresses integrin-mediated neutrophil adherence function. J Invest Dermatol. Feb. 1992;98(2):135-40.
Borkan et al., An outbreak of venomous spider bites in a citrus grove. Am J Trop Med Hyg. Mar. 1995;52(3):228-30.
Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.
Brants, The Distribution of Tobacco Mosaic Virus (TMV) in Excised Tomato Roots Cultivated in Vitro. Tijdschr Plantenziekten, 1962;68:198-207.
Brassard et al., Interferon-α as an immunotherapeutic protein. J Leukoc Biol. Apr. 2002;71(4):565-81.
Breathnach, Azelaic acid: potential as a general antitumoural agent. Med Hypotheses. Mar. 1999;52(3):221-6.
Brennan et al., Automated bioassay of interferons in microtest plates. Biotechniques. Jun./Jul. 1983(1):78-82.
Broughton, Management of the brown recluse spider bite to the glans penis. Mil Med. Oct. 1996;161(10):627-9.
Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.
Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.
Burleson, Chapter 14. Influenza Virus Host Resistance Model for Assessment of Immunostimulation, and Antiviral Compounds. Methods in Immunology. 1995;2:181-202.
Buschle et al., Interferon γ inhibits apoptotic cell death in B cell chronic lymphocytic leukemia. J Exp Med. Jan. 1, 1993;177(1):213-8.
Cai et al., Evaluation of trifluoroacetic acid as an ion-pair reagent in the separation of small ionizable molecules by reversed-phase liquid chromatography. Analytica Chmica Acta. 1999; 399:249-258.
Cantell et al., IFN-γ Enhances Production of IFN-α in Human Macrophages but Not in Monocytes. J Interferon and Cytokine Res. 1996;16:461-63.
Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.
Carrigan et al., Synthesis and in vitro pharmacology of substituted quinoline-2,4-dicarboxylic acids as inhibitors of vesicular glutamate transport. J Med Chem. May 23, 2002;45(11):2260-76.
Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997; 330(12):383-6.
Cheson et al., National Cancer Institute-sponsored Working Group guidelines for chronic lymphocytic leukemia: revised guidelines for diagnosis and treatment. Blood. Jun. 15, 1996;87(12):4990-7.
Chuang et al., Toll-like receptor 9 mediates CpG-DNA signaling. J Leukoc Biol. Mar. 2002;71(3):538-44.
Claisen, [Über α-Methyl-isoxazol.] Berichte. 1909;42:59-69. German.
Cohen et al., Cytokine function: a study in biologic diversity. Am J Clin Pathol. May 1996;105(5):589-98.
Cole et al., Brown recluse spider envenomation of the eyelid: an animal model. Ophthal Plast Reconstr Surg. Sep. 1995; 11(3):153-64.
Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.
Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.
Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.
Davis, Current therapy for chronic hepatitis C. Gastroenterology. Feb. 2000;118(2 Suppl 1):S104-14.
Davis et al., Heterocyclic Syntheses with Malonyl Chloride. Part VI. 3-Substituted Pyridine Derivatives from α-Methylene-nitriles. J Chem Soc. 1962:3638-44.
Davis et al., Self-administered topical imiquimod treatment of vulvar intraepithelial neoplasia. A report of four cases. J Reprod Med. Aug. 2000;45(8):619-23.
De et al., Structure-activity relationships for antiplasmodial activity among 7-substituted 4-aminoquinolines. J Med Chem. Dec. 3, 1998;41(25):4918-26.
Debol et al., Anti-inflammatory action of dapsone: inhibition of neutrophil adherence is associated with inhibition of chemoattractant-induced signal transduction. J Leukoc Biol. Dec. 1997;62(6):827-36.
De Clerq, Synthetic interferon inducers. Top Curr Chem. 1974;52:173-208.

(56) References Cited

OTHER PUBLICATIONS

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.
Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.
Delgado, Textbook of Organic Medicinal and Pharmaceutical Chemistry, Ninth Edition, Remers, ed., 1991:30-1.
Denzel et al. Imidazo [4,5-c]- and [4,5-b]pyridines. J. Heterocyclic Chem. 1977;14:813-821.
Diaz-Arrastia et al., Clinical and molecular responses in high-grade intraepithelial neoplasia treated with topical imiquimod 5%. Clin Cancer Res. Oct. 2001;7(10):3031-3.
Di Carlo et al., Neutrophils in anti-cancer immunological strategies: old players in new games. J Hematother Stem Cell Res. Dec. 2001;10(6):739-48.
Dicken et al., Reactions at High Pressures. [3+2] Dipolar Cycloaddition of Nitrones with Vinyl Ethers. J Org Chem. 1982;47:2047-51.
Dockrell et al., Imiquimod and resiquimod as novel immunomodulators. J Antimicrob Chemother. Dec. 2001;48(6):751-5.
Dorwald, "Preface." Side Reactions in Organic Synthesis. A Guide to Successful Synthesis Design. Wiley-VCH. 2005: IX.
Douglas, Introduction to Viral Diseases. In: Cecil Textbook of Medicine. Bennet et al., eds. 20th Ed. W.B. Saunders Company. 1996:2:1739-47.
Doyle et al., Toll-like receptor 3 mediates a more potent antiviral response than Toll-like receptor 4. J Immunol. Apr. 1, 2003;170(7):3565-71.
Drexler et al., Bryostatin 1 induces differentiation of B-chronic lymphocytic leukemia cells. Blood. Oct. 1989;74(5):1747-57.
Dzionek et al. BDCA-2, BDCA-3, and BDCA-4: three markers for distinct subsets of dendritic cells in human peripheral blood. J Immunol. Dec. 1, 2000;165(11):6037-46.
Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.
Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.
Fecci et al., The history, evolution, and clinical use of dendritic cell-based immunization strategies in the therapy of brain tumors. J Neurooncol. Aug.-Sep. 2003;64(1-2):161-76.
Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract p. 81.
Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.
Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.
Frankel et al., The Preparation of N-Disubstituted Formamides. Tetrahedron Lett. 1959;7:5-7.
Frantz et al., Toll4 (TLR4) expression in cardiac myocytes in normal and failing myocardium. J Clin Invest. Aug. 1999;104(3):271-80.
Fu et al., Regioselective Catalytic Hydrogenation of Polycyclic Aromatic Hydocarbons under Mild conditions. J Org Chem. 1980;45:2979-803.
Fuchsberger et al., Priming Interferon-a 1 or Interferon-a 2 Enhances the Production of Both Subtypes Simultaneously. J Interferon and Cytokine Res. 1995;15:637-39.

Galose, DAPSONE (diaminodiphenylsulphone DDS). Clinical Toxicology Review. 1999:21(9). 3 pages.
Gendron, Loxosceles ignali Envenomation. Am J Emerg Med. Jan. 1990;8(1):51-4.
Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.
Giannini et al., Influence of the Mucosal Epithelium Microenvironment on Langerhans Cells: Implications for the Development of Squamous Intraepithelial Lesions of the Cervix. Int J Cancer. 2002;97:654-59.
Gibson et al., Cellular requirements for cytokine production in response to the immunomodulators imiquimod and S-27609. J Interferon Cytokine Res. Jun. 1995;15(6):537-45.
Gibson et al., Plasmacytoid dendritic cells produce cytokines and mature in response to the TLR7 agonists, imiquimod and resiquimod. Cell Immunol. Jul.-Aug. 2002;218(1-2):74-86.
Gitelson et al., Chronic lymphocytic leukemia-reactive T cells during disease progression and after autologous tumor cell vaccines. Clin Cancer Res. May 2003;9(5):1656-65.
Gomez et al., Intradermal anti-loxosceles Fab fragments attenuate dermonecrotic arachnidism. Acad Emerg Med. 1999;6:1195-202.
Gorden et al., Synthetic TLR agonists reveal functional differences between human TLR7 and TLR8. J Immunol. Feb. 1, 2005;174(3):1259-68.
Gordon, Pattern recognition receptors: doubling up for the innate immune response. Cell. Dec. 27, 2002;111(7):927-30.
Gunning et al., Chemoprevention by lipoxygenase and leukotriene pathway inhibitors of vinyl carbamate-induced lung tumors in mice. Cancer Res. Aug. 1, 2002;62(15):4199-201.
Gürsel et al., Differential and competitive activation of human immune cells by distinct classes of CpG oligodeoxynucleotide. J Leukoc Biol. May 2002;71(5):813-20.
Hart, Napthyridines Hydroxynaphthyridies, Journal of Chemical Society, 1956;Part III:212-4.
Hartmann et al., Rational design of new CpG oligonucleotides that combine B cell activation with high IFN-alpha induction in plasmacytoid dendritic cells. Eur J Immunol. Jun. 2003;33(6):1633-41.
Hayashi Toll-like receptors stimulate human neutrophil function. Blood. Oct. 1, 2003;102(7):2660-69. Epub Jun. 26, 2003.
Hayes et al., Regulation of Interferon Production by Human Monocytes: Requirements for Priming for Lipopolysaccharide-Induced Production. J Leukocyte Biol. 1991;50:176-81.
Heil et al., Species-specific recognition of single-stranded RNA via toll-like receptor 7 and 8. Science. Mar. 5, 2004;303(5663):1526-9. Epub Feb. 19, 2004.
Heil et al., Synthetic immunostimulatory compounds activate immune cells via TLR7 and TLR8. 33th Annual Meeting of the Deutsche Gessellschaft Mr Immunologie, Marburg 2002. Abstract C.6.
Hemmi et al., Small anti-viral compounds activate immune cells via the TLR7 MyD88-dependent signaling pathway. Nat Immunol. Feb. 2002;3(2):196-200. Epub Jan. 22, 2002.
Hobbs et al., Comparison of hyperbaric oxygen and dapsone therapy for loxosceles envenomation. Acad Emerg Med. Aug. 1996;3(8):758-61.
Hoffman et al., Conformational requirements for histamine H2-receptor inhibitors: a structure-activity study of phenylene analogues related to cimetidine and tiotidine. J Med Chem. Feb. 1983;26(2):140-4.
Hofmanová et al., Lipoxygenase inhibitors induce arrest of tumor cells in S-phase of the cell cycle. Neoplasma. 2002;49(6):362-7.
Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.
Horng et al., The adaptor molecule TIRAP provides signaling specificity for Toll-like receptors. Nature. Nov. 21, 2002;420(6913):329-33.
Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

(56) References Cited

OTHER PUBLICATIONS

Houben-Weyl, Quinoline and Isoquinoline. Methoden der Organischen Chemie. 1980:271-79. German.
Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.
Huppatz, Systemic fungicides. The synthesis of certain pyrazole analogues of carboxin. Aust J Chem. 1983;36:135-47.
Iino et al., Treatment of Chronic Hepatitis C With High-Dose Interferon α-2b. Multicenter Study. Dig Dis Sci. 1993;38(4):612-18.
Ito et al., Interferon-alpha and interleukin-12 are induced differentially by Toll-like receptor 7 ligands in human blood dendritic cell subsets. J Exp Med. Jun. 3, 2002;195(11):1507-12.
Iwashita et al., Syntheses of Isoretronecanol and Lupinine. J Org Chem. 1982;47:230-33.
Izumi et al., 1H-Imidazo[4,5-c]quinoline derivatives as novel potent TNF-alpha suppressors: synthesis and structure-activity relationship of 1-, 2-and 4-substituted 1H-imidazo[4,5-c]quinolines or 1H-imidazo[4,5-c]pyridines. Bioorg Med Chem. Jun. 12, 2003;11(12):2541-50.
Jacobs, Chapter 1. The Synthesis of Acetylenes. In: Organic Reactions. New York: Wiley & Sons, Inc., 1949. vol. 5. 1-78.
Jahnsen et al., Extensive recruitment of IL-3Rαhigh dendritic-cell precursors to allergic nasal mucosa during allergen challenge. Immunology Left. 1999;69(1):123. Abstract #32.2.
Jain et al., Chemical and pharmacological investigations of some omega-substituted alkylamino-3-aminopyridines. J Med Chem. Jan. 1968;11(1):87-92.
Jurk et al. Human TLR7 and TLR8 independently confer responsiveness to the antiviral compound R-848. Nat Immunol. Jun. 2002;3(6):499.
Juweid, Radioimmunotherapy of B-Cell Non-Hodgkin's Lymphoma: From Clinical Trials to Clinical Practice. J Nuclear Med. 2002;43(11):1507-29.
Katritsky et al., Comprehensive Heterocyclic Chemistry: The Structure, Reactions, Synthesis and Uses of Heterocyclic Compounds. 1984;2:586-587.
Keating et al., Long-term follow-up of patients with chronic lymphocytic leukemia treated with fludarabine as a single agent. Blood. Jun. 1, 1993;81(11):2878-84.
Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-74.
Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some ò-nitrokenes. J Am Chem Soc. 1947;69:2271-2275.
Kornnau, Host modulation as a therapeutic strategy in the treatment of periodontal disease. Clin Infect Dis. Mar. 1999;28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et al., Autoimmune aspects of cytokine and anticytokine therapies. Am J Med. Oct. 1, 2003;115(5):390-7.
Krenitsky et al., Imidazo[4,5-c]pyridines (3-deazapurines) and their nucleosides as immunosuppressive and anti-inflammatory agents. J Med Chem. Jan. 1986;29(1):138-43.
Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.
Lee et al., p38 mitogen-activated protein kinase inhibitors—mechanisms and therapeutic potentials. Pharmacol Ther. 1999;82:389-97.
Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.
Lehner et al., The role of γδ cells and β-chemokines in mucosal protection against SIV infection. Immunology Lett. 1999;69:25-192. Abstract 2.1.
Levy et al., Unique efficacy of Toll-like receptor 8 agonists in activating human neonatal antigen-presenting cells. Blood. Aug. 15, 2006;108(4):1284-90. Epub Apr. 25, 2006.
Leynadier et al., Allergic reactions to North African scorpion venom evaluated by skin test and specific IgE. J Allergy Clin Immunol. Jun. 1997;99(6 Pt 1):851-3. 4 pages.
Li et al., An improved protocol for the preparation of 3-pyridyl- and some arylboronic acids. J Org Chem. Jul. 26, 2002;67(15):5394-7.
Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.
Litt et al., Mucosal delivery of vaccine antigens displayed on the surface of Lactococcus lactis. Immunology Lett. 1999:69(1):61. Abstract #11.26.
Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.
Loesche et al., Treatment paradigms in periodontal disease. Compend Contin Educ Dent. Mar. 1997;18(3):221-6, 228-30, 232 passim; quiz 234. Review.
Luger et al., Evidence for an epidermal cytokine network. J Invest Dermatol. Dec. 1990;95(6 Suppl):100S-104S.
Luskin et al., Olefinic Derivatives of 2,4-Diamino-s-triazines. J Org Chem. 1958;23:1032-37.
Macchia et al., Synthesis and antiviral properties of 9-[(2-methyleneaminoxyethoxy)methyl]guanine derivatives as novel Acyclovir analogues. Farmaco. Feb. 2000;55(2):104-8.
Majeski et al., Action of venom from the brown recluse spider (*Loxosceles reclusa*) on human neutrophils. Toxicon. 1977;15(5):423-7.
Makarenkova et al., Identification of delta- and mu-type opioid receptors on human and murine dendritic cells. J Neuroimmunol. 2001;117:68-77.
Male et al., Introduction to the Immune System. In: Immunology. Elsevier. 2006:6-7.
Masihi, Progress on novel immunomodulatory agents for HIV-1 infection and other infectious diseases. Expert Opin Ther Patents. 2003;13(6):867-82.
Masiukiewicz et al., Scalable Syntheses of N$^\alpha$-Benzyloxy carbonyl-$_L$-Ornithine and of N$^\alpha$-(9-Fluorenylmethoxy)Carbonyl-$_L$-Ornithine. Org Prep Proced Int. 2002;34:531-37.
Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.
Mathur et al., Cell-mediated immune system regulation in periodontal diseases. Crit Rev Oral Biol Med. 1997;8(1):76-89.
Maynor et al., Brown recluse spider envenomation: a prospective trial of hyperbaric oxygen therapy. Acad Emerg Med. Mar. 1997;4(3):184-92.
Mbow et al., Small molecule and biologic modulators of the immune response to hepatitis C virus. Mini Rev Med Chem. May 2006;6(5):527-31.
McCarthy et al., Opioids, opioid receptors, and the immune response. Drug & Alcohol Dependence. 2001;62:111-23.
McKennon et al., A Convenient Reduction of Amino Acids and Their Derivatives. J Org Chem. 1993;58:3568-71.

(56) References Cited

OTHER PUBLICATIONS

McLaughlin et al., Opioid growth factor (OGF) inhibits the progression of human squamous cell carcinoma of the head and neck transplanted into nude mice. Cancer Lett. 2003;199:209-17.
Medzhitov, Toll-Like Receptors and Innate Immunity. Nature Rev Immunol. 2001;1:135-45.
Mee et al., Stille coupling made easier—the synergic effect of copper(I) salts and the fluoride ion. Angew Chem. 2004;116:1152-56.
Merigian et al., Envenomation From the Brown Recluse Spider: Review of Mechanism and Treatment Options. Am J Ther. Oct. 1996;3(19):724-734.
Miller et al., Imiquimod applied topically: a novel immune response modifier and new class of drug. Int J Immunopharmacol. Jan. 1999;21(1):1-14.
Minakawa et al., Nucleosides and Nucleotides. 184. Synthesis and Conformational Investigation of Anti-Fixed 3-Deaza-3-halopurine Ribonucleosides. J Org Chem. 1999;64:7158-72.
Moebius et al., The mysteries of sigma receptors: new family members reveal a role in cholesterol synthesis. Trends Pharmacol Sci. Mar. 1997;18(3):67-70.
Moldoveanu et al., Poly-L-lysine as a potential mucosal adjuvant. Immunology Lett. 1999;69(1):62. Abstract #11.28.
Mollick et al., MUC1-like tandem repeat proteins are broadly immunogenic in cancer patients. Cancer Immun. Mar. 17, 2003;3:3. 17 pages.
Moody et al., Lipoxygenase inhibitors prevent lung carcinogenesis and inhibit non-small cell lung cancer growth. Exp Lung Res. Jul.-Aug. 1998;24(4):617-28.
Moraczewski et al., Using Hydrogen Bonding to Control Carbamate C—N Rotamer Equilibria. Org Chem. Oct. 16, 1998;63(21):7258-7262.
Mosbech et al., [Allergy to insect stings] Ugeskr Laeger. Oct. 28, 1991;153(44):3067-71. Danish.
Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.
Muller et al., An improved one-pot procedure for the synthesis of alkynes from aldehydes. Synlett. 1996;6:521-522.
Mutschler et al., 9.2 Anti-infectives. In: Drug Actions: Basic Principles and Therapeutic Aspects. 1995:515-80.
Muzio et al., Differential expression and regulation of toll-like receptors (TLR) in human leukocytes: selective expression of TLR3 in dendritic cells. J Immunol. Jun. 1, 2000;164(11):5998-6004.
Nagarajan et al., Condensed heterotricycles: synthesis of pyrazolo[3,4-c]quinoline derivatives. Indian Journal of Chemistry. 1992;31B:316-321.
Nagase et al., Expression and function of Toll-like receptors in eosinophils: activation by Toll-like receptor 7 ligand. J lmmunol. Oct. 15, 2003;171(8):3977-82.
Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.
Ohana et al., Differential effect of adenosine on tumor and normal cell growth: focus on the A3 adenosine receptor. Journal of Cellular Physiology. Jan. 2001;186(1):19-23. Review.
O'Mahony et al., New patient-applied therapy for anogenital warts is rated favourably by patients. Intl J STD & AIDS. 2001;12:565-70.
Osol et al., Chapter 27: Structure-Activtiy Relationship and Drug Design. In: Remington's Pharmaceutical Sciences. 16th Ed. Mach Publishing. 1980:420-35.
Ottonello et al., Sulphonamides as anti-inflammatory agents: old drugs for new therapeutic strategies in neutrophilic inflammation? Clin Sci (Lond). Mar. 1995;88(3):331-6.
Ozinsky et al., The repertoire for pattern recognition of pathogens by the innate immune system is defined by cooperation between Toll-like receptors. Proc. Nat. Acad. Sci. 2000; 97(25):13766-71.
Page et al., Advances in the pathogenesis of periodontitis: summary of developments, clinical implications and future directions. Periodontal 2000. Jun. 1997:14:216-48.
Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.
Park et al., Sodium Dithionite Reduction of Nitroarenes Using Viologen as an Electron Phase-Transfer Catalyst. Tetrahedron Lett. 1993;34(46):7445-46.
Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.
Patrick et al., Paragraph 10.3: Drug optimization: strategies in drug design. In: An Introduction to Medicinal Chemistry. Oxford: Oxford University Press. Jan. 2005. 200-218.
Pavletic et al., Outcome of allogeneic stem cell transplantation for B cell chronic lymphocytic leukemia. Bone Marrow Transplant. Apr. 2000;25(7):717-22.
Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.
Payvandi et al., Exogenous and Endogenous IL-10 Regulate IFN-α Production by Peripheral Blood Mononuclear Cells in Response to Viral Stimulation. J Immunol. 1998;160:5861-68.
Peschke et al., Synthesis and in vitro characterization of new growth hormone secretagogues derived from ipamorelin with dipeptidomimetic N-terminals. Eur J Med Chem. 1999;34:363-380.
Peterson et al., The opioid-cytokine connection. J Neuroimmunol. 1998;83:63-69.
Phillips et al., Therapy of brown spider envenomation: a controlled trial of hyperbaric oxygen, dapsone, and cyproheptadine. Ann Emerg Med. Mar. 1995;25(3):363-8.
Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.
Poljakovic et al., iNOS and COX-2 immunoreactivity in the mice bladder and kidney after bacterial instillation. Immunology Lett. 1999;69(1):122. Abstract #31.5.
Powell et al., Compendium of excipients for parenteral formulations. PDA J Pharm Sci Technol. Sep.-Oct. 1998;52(5):238-311.
Prelog et al., Cycloalkeno-pyridine. Hely Chem Acta. 1945;28:1684-93. German.
Rees et al., Brown recluse spider bites. A comparison of early surgical excision versus dapsone and delayed surgical excision. Ann Surg. Nov. 1985;202(5):659-63.
Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.
Rhodes, Discovery of immunopotentiatory drugs: current and future strategies. Clin Exp Immunol. Dec. 2002;130(3):363-9.
Ribera et al., "Spontaneous" complete remissions in chronic lymphocytic leukemia: report of three cases and review of the literature. Blood Cells. 1987;12(2):471-79.
Ritter et al., A new reaction of nitriles; amides from alkenes and mononitriles. J Am Chem Soc. Dec. 1948;70(12):4045-8.
Rocca et al., Carbolines. Part VII. Ansidines, Convenient tools to synthesize fficien-β-carbolines. J Heterocyclic Chem. 1995;32:1171-1175.
Rocca et al., Connection between metalation and cross-coupling strategies. A new convergent route to azacarbazoles. Tetrahedron. 1993;49(1):49-64.
Rollins, Chemokines. Blood. Aug. 1, 1997;90(3):909-28. Review.
Rosenberg et al., Treatment of 283 consecutive patients with metastatic melanoma or renal cell cancer using high-dose bolus interleukin 2. JAMA. Mar. 23-30, 1994;271(12):907-13.

(56) References Cited

OTHER PUBLICATIONS

Rothel et al., The use of recombinant ovine IL-1beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymetry. 1999;10:3417-30.

Severa et al., Sensitization to TLR7 agonist in IFN-beta-preactivated dendritic cells. J Immunol. May 15, 2007;178(10):6208-16.

Seymour et al., Cellular immunity and hypersensitivity as components of periodontal destruction. Oral Dis. Mar. 1996;2(1):96-101. Review.

Shelburne et al., Quantitation of Bacteroids forsythus in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science. Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, Loxosceles reclusa. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. Latrodectus mactans. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3): 697-700.

Testerman et al., Cytokine induction by the immunomodulators imiquimod and S-27609. J Leukoc Biol. Sep. 1995;58(3):365-72.

(56) References Cited

OTHER PUBLICATIONS

Thesing et al., [Darstellung and Eigenschaften des $\Delta^1$-Pyrrolin-N-oxyds.]. Chem Ber. 1959;92:1748-55. German. abstract Only.
Thiruvikraman et al., Synthesis and reactions of pyrazolo-[3,4-c]quinoline derivatives. Indian Journal of Chemistry. 1987;266:695-696.
Tomai et al., Imiquimod: in vivo and in vitro characteristics and toxicology. In: Cutaneous Infection and Therapy. Aly et al., eds. Marcel Dekkar, Inc., New York. 1997:405-15.
Tomic et al., Sensitization of IL-2 Signaling through TLR-7 Enhances B Lymphoma Cell Immunogenicity. J Immunol. 2006;176:3830-39.
Tomioka et al., Asymmetric Alkylation of $\alpha$-Alkyl $\beta$-Keto Esters. J Am Chem Soc. 1984;106:2718-19.
Totterman et al., Phorbol ester-induced differentiation of chronic lymphocytic leukaemia cells. Nature. Nov. 13, 1980;288(5787):176-8.
Tracy et al., Studies in the Pyridine Series. II. Synthesis of 2-Methyl-3-($\beta$-Hydroxyethyl)pyridine and of the Pyridine Analog of Thiamine (Vitamin B2). J Org Chem. 1941;6:54-62.
Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.
Urosevic et al., Imiquimod treatment induces expression of opioid growth factor receptor: a novel tumor antigen induced by interferon-alpha? Clin Cancer Res. Aug. 1, 2004;10(15):4959-70.
Van De Kerhof, New Immunomodulatory Drugs. In: Skin and Environment: Perception and Protection. Ring et al., eds., 10th EADV Congress, Oct. 10-14, Munich, Germany. 2001:1:343-48.
Vasilakos et al., Adjuvant Activities of Immune Response Modifier R-848: Comparison with CoG ODN. Cell Immunol. 2000;204:64-74.
Vieweg et al., Tumor vaccines: from gene therapy to dendritic cells—the emerging frontier. Urol Clin North Am. Aug. 2003;30(3):633-43.
Vilcek, The cytokines: An overview. In: The Cytokine Handbook, Fourth Ed. M. Lotze and A.W. Thompson (eds.), 2003;1:3-14.
Volhardt, 18-5. Amides: The Least-Reactive Carboxylic Acid Derivatives. Organic Chemistry. 1987:813.
Vollmer et al., Highly immunostimulatory CpG-free oligodeoxynucleotides for activation of human leukocytes. Antisense Nucleic Acid Drug Dev. Jun. 2002;12(3):165-75.
Wagner et al., Induction of cytokines in cynomolgus monkeys by the immune response modifiers, imiquimod, S-27609 and S-28463. Cytokine. Nov. 1997;9(11):837-45.
Wagner et al., Modulation of TH1 and TH2 Cytokine Production with the Immune Response Modifiers, R-848 and Imiquimod. Cellular Immunology. 1999;191:10-19.
Wang, Structure and Chemistry of 4-Hydroxy-6-methyl-2-pyridone. J Heterocyclic Chem. 1970;7:389-92.
Warren et al., Macrophage Growth Factor CSF-1 Stimulates Human Monocyte Production of Interferon, Tumor Necrosis Factor, and Colony Stimulating Activity. J Immunol. 1986;137(7):2281-85.
Wasserman et al., Loxoscelism and necrotic arachnidism. J Toxicol Clin Toxicol. 1983-1984;21(4-5):451-72.
Wedlock et al., Physiological effects and adjuvanticity of recombinant brushtail possum TNF-alpha. Immunol Cell Biol. Feb. 1999;77(1):28-33.
Wells, Additivity of Mutational Effects in Proteins. Biochemistry. 1990;29(37):8509-17.
Wermuth, Molecular Variations Based on Isosteric Replacements. Practice of Medicinal Chemistry.1996:203-37.
Wexler et al., Accurate identification of experimental pulmonary metastases. J Natl Cancer Inst. Apr. 1966;36(4):641-5.
Wibaut et al., Syntheses of 3,4-Dimethylpyridine, 2,3-Dimethylpridine and 2-Methyl-3-Ethylpyridine. Rec Trav Chim. 1944;63:231-38.
Wierda et al., CD40-ligand (CD154) gene therapy for chronic lymphocytic leukemia. Blood. Nov. 1, 2000;96(9):2917-24.
Wieseler-Frank et al., Central proinflammatory cytokines and pain enhancement. Neurosignals. 2005;14(4):166-74.
Williams et al., Grignard Reactions to Chiral Oxazolidine Aldehydes. Tetrahedron. 1996;52:11673-94.
Wilson et al., Spiders and spider bites. Dermatol Clin. Apr. 1990;8(2):277-86.
Wozniak et al., The amination of 3-nitro-1, 5-naphthyridines by liquid ammonia/potassium permanganate1,2. A new and convenient animation method. J. Royal Netherlands Chem Soc. Dec. 12, 1983(102):511-3.
Wright et al., Clinical presentation and outcome of brown recluse spider bite. Ann Emerg Med. Jul. 1997;30(1):28-32.
Wu et al., Murine B16 melanoma vaccination-induced tumor immunity: identification of specific immune cells and functions involved. J Interferon Cytokine Res. Dec. 2001;21(12):1117-27.
Yamamoto et al., Essential role for TIRAP in activation of the signalling cascade shared by TLR2 and TLR4. Nature. Nov. 21, 2002;420(6913):324-9.
Yeung-Yue et al., The management of herpes simplex virus infections. Curr Opin Infect Dis. Apr. 2002;15(2):115-22.
Yutilov et al., Synthesis and some reactions of 4-nitroimidazo[4-5-c]pyridin-2-ones. CAPLUS English Abstract DN 91:175261. VINITI. 1978:1193-78. Abstract Only.
Zagon et al., Immunoelectron microscopic localization of the opioid growth factor receptor (OGFr) and OGF in the cornea. Brain Res. 2003;967:37-47.
Zagon et al., Opioids and the apoptotic pathway in human cancer cells. Neuropeptides. 2003;37:79-88.
Zagon et al., The biology of the opioid growth factor receptor (OGFr). Brain Res Rev. Feb. 2002;38(3):351-76. Review.
Zagon et al., The expression and function of the OGF-OGFr axis—a tonically active negative regulator of growth—in COS cells. Neuropeptides. Oct. 2003;37(5):290-7.
Zambon, Periodontal diseases: microbial factors. Ann Periodontol. Nov. 1996;1(1):879-925.
Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.
Zhang et al., Structural features of azidopyridinyl neonicotinoid probes conferring high affinity and selectivity for mammalian alpha4beta2 and *Drosophila* nicotinic receptors. J Med Chem. Jun. 20, 2002;45(13):2832-40.
Zhu et al., Inhibition of murine dendritic cell activation by synthetic phosphorothioate oligodeoxynucleotides. J Leukoc Biol. Dec. 2002;72(6):1154-63.
Zhu et al., Inhibition of murine macrophage nitric oxide production by synthetic oligonucleotides. J Leukoc Biol. Apr. 2002;71(4):686-94.
Ziegler-Heitbrock et al., Favorable response of early stage B CLL patients to treatment with IFN-alpha 2. Blood. May 1, 1989;73(6):1426-30.
Zyryanov et al., Heterocyclization of 1-(2'-Carbethoxyphenyl)-5-Methyltetrazole. Chemistry of Heterocylic Compounds. English Edition. 1981;16(12):1286-88.
Supplementary European Search Report for EP 06720400.8 dated Mar. 30, 2010.
Chollet et al., Development of a Topically Active Imiquimod Formulation. Pharma Dev Technol. 1999;4(1):35-43.
Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.
Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;8475:Abstract 3030.
Shiller et al. 2006. *Experimental Dermatology*. 15:331-341. "Immune response modifiers—mode of action".

* cited by examiner

AQUEOUS GEL FORMULATIONS CONTAINING IMMUNE RESPONSE MODIFIERS

CROSS REFERENCE TO RELATED APPLICATIONS

This application is a divisional of U.S. application Ser. No. 11/883,665, filed Aug. 3, 2007, now pending, which is a national stage filing under 35 U.S.C. 371 of PCT/US2006/04201, filed Feb. 3, 2006, which claims priority to U.S. Provisional Application No. 60/650,030, filed Feb. 4, 2005, the disclosures of which are incorporated by reference in their entirety herein.

BACKGROUND

Many imidazoquinoline amine, imidazopyridine amine, 6,7-fused cycloalkylimidazopyridine amine, 1,2-bridged imidazoquinoline amine, thiazoloquinoline amine, oxazoloquinoline amine, thiazolopyridine amine, oxazolopyridine amine, imidazonaphthyridine amine, imidazotetrahydronaphthyridine amine, and thiazolonaphthyridine amine compounds have demonstrated potent immunostimulating, antiviral and antitumor (including anticancer) activity, and have also been shown to be useful as vaccine adjuvants and for the treatment of TH2-mediated diseases. These compounds are hereinafter collectively referred to as "IRM" (immune response modifier) compounds.

The mechanism for the immunostimulatory activity of these IRM compounds is thought to be due in substantial part to enhancement of the immune response by induction of various important cytokines (e.g., interferons, interleukins, tumor necrosis factor, etc.). Such compounds have been shown to stimulate a rapid release of certain monocyte/macrophage-derived cytokines and are also capable of stimulating B cells to secrete antibodies, which play an important role in these IRM compounds' activities. One of the predominant immunostimulating responses to these compounds is the induction of interferon (IFN)-α production, which is believed to be very important in the acute antiviral and antitumor activities seen. Moreover, up regulation of other cytokines such as, for example, tumor necrosis factor (TNF), Interleukin-1 (IL-1), IL-6, and IL-12 also have potentially beneficial activities and are believed to contribute to the antiviral and antitumor properties of these compounds.

Although some of the beneficial effects of IRMs are known, the ability to provide therapeutic benefit via topical application of an IRM compound for treatment of a particular condition at a particular location may be hindered by a variety of factors. These factors include irritation of the dermal or mucosal tissue to which the formulation is applied, ciliary clearance of the formulation, formulation wash away, insolubility and/or degradation of the IRM compound in the formulation, physical instability of the formulation (e.g., separation of components, thickening, precipitation/agglomeration of active ingredient, and the like), and poor permeation, for example. Accordingly, there is a continuing need for new methods and formulations to provide the greatest therapeutic benefit from this class of compounds.

SUMMARY

The present invention is directed to aqueous gel formulations, kits, and methods of use. Herein, a "gel" is a composition that is substantially free of oil (and hence, is not a cream or a lotion). Preferably, gels of the present invention have a viscosity of at least 1000 Centipoise (cps) at room temperature (i.e., about 25° C.). Preferably, gels of the present invention have a viscosity of no greater than 50,000 cps, and more preferably no greater than 30,000 cps.

Aqueous gels are not easily formed using certain IRMs due to the low intrinsic aqueous solubility of the free base (typically, less than 500 µg at 25° C.). As a result, a cosolvent is typically used or a salt of the IRM is prepared in situ. This can result in the need for negatively charged thickeners, particularly two negatively charged thickeners, to provide the desirable viscosity. In preferred embodiments of the present invention, the negatively charged thickeners are not covalently bonded to the IRM.

In one embodiment, such aqueous gels include: water; an immune response modifier (IRM) other than 1-(2-methylpropyl)-1H-imidazo[4,5-c][1,5]naphthyridin-4-amine; a pharmaceutically acceptable acid; a water-miscible cosolvent; and a thickener system including a negatively charged thickener; wherein the aqueous gel has a viscosity of at least 1000 cps at 25° C.

In one embodiment, such aqueous gels are prepared by a method that includes combining components including: water; an immune response modifier (IRM) other than 1-(2-methylpropyl)-1H-imidazo[4,5-c][1,5]naphthyridin-4-amine, or a salt thereof; a water-miscible cosolvent; and a thickener system including a negatively charged thickener; wherein the aqueous gel has a viscosity of at least 1000 cps at 25° C.

Gel formulations of the present invention can provide desirable vehicles for an IRM compound and can allow for easier manufacture and increased residence time of an IRM compound, particularly on dermal and/or mucosal tissue.

Furthermore, the use of negatively charged thickeners in the aqueous gels of the present invention reduces systemic exposure to the drug and hence reduces systemic levels of cytokines. This is desirable for many conditions for which treatment at a particular location (e.g., cervical dysplasia) is preferred. The use of a combination of negatively charged thickeners (i.e., at least two) is desirable when higher levels of cosolvents are used due to the low solubility of the drug (whether in free base or salt form) in water. This results in an aqueous gel that reduces systemic exposure and is physically stable.

In certain embodiments, the immune response modifier is selected from the group consisting of imidazoquinoline amines, tetrahydroimidazoquinolines, imidazopyridine amines, 6,7-fused cycloalkylimidazopyridine amines, imidazonaphthyridine amines, tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; 1H-imidazo dimers fused to pyridine amines, quinoline amines, tetrahydroquinoline amines, naphthyridine amines, or tetrahydronaphthyridine amines; and combinations thereof.

The present invention also provides methods of using the formulations of the present invention. In one embodiment, the present invention provides a method for delivering an IRM compound to mucosal tissue of a subject, the method including applying an aqueous gel of the present invention. Preferably, the mucosal tissue is associated with a condition selected from the group consisting of a cervical dysplasia, a papilloma virus infection of the cervix, a low-grade squamous intraepithelial lesion, a high-grade squamous intraepithelial lesion, atypical squamous cells of undetermined significance, a cervical intraepithelial neoplasia, an atopic allergic response, allergic rhinitis, a neoplastic lesion, and a premalignant lesion.

In another method, the aqueous gels of the present invention can be used to treat a dermal and/or mucosal condition in a subject in need thereof. The method includes applying an aqueous gel of the invention to the affected area of the subject. The present invention also provides kits that include a barrel type applicator and an aqueous gel of the present invention, which can be in a separate container or prefilled in the barrel type applicator.

The terms "comprises" and variations thereof do not have a limiting meaning where these terms appear in the description and claims.

As used herein, "a," "an," "the," "at least one," and "one or more" are used interchangeably. Thus, for example, an aqueous formulation that comprises "an" immune response modifier can be interpreted to mean that the formulation includes "one or more" immune response modifiers. Similarly, a formulation comprising "a" preservative can be interpreted to mean that the formulation includes "one or more" preservatives.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides aqueous gel formulations, kits, and methods of use. Such gels are compositions that are substantially free of oil (and hence, they are not creams or lotions). Preferably, gels of the present invention have a viscosity of at least 1000 Centipoise (cps) at 25° C. Preferably, gels of the present invention have a viscosity of no greater than 50,000 cps, and more preferably no greater than 30,000 cps.

In one embodiment, such aqueous gels include: water; an immune response modifier (IRM) other than 1-(2-methylpropyl)-1H-imidazo[4,5-c][1,5]naphthyridin-4-amine; a pharmaceutically acceptable acid; a water-miscible cosolvent; and a thickener system including a negatively charged thickener (preferably, at least two negatively charged thickeners, which are typically of different charge density); wherein the aqueous gel has a viscosity of at least 1000 cps at 25° C.

In one embodiment, such aqueous gels are prepared by a method that includes combining components including: water; an immune response modifier (IRM) other than 1-(2-methylpropyl)-1H-imidazo[4,5-c][1,5]naphthyridin-4-amine, or a salt thereof; a water-miscible cosolvent; and a thickener system including a negatively charged thickener (preferably, at least two negatively charged thickeners, which are typically of different charge density); wherein the aqueous gel has a viscosity of at least 1000 cps at 25° C.

The immune response modifier is substantially completely dissolved at a therapeutic level (i.e., therapeutically effective amount) in the formulation at room temperature. This amount is effective to treat and/or prevent a specified condition. In general, the amount of IRM present in an aqueous gel formulation of the invention will be an amount effective to provide a desired physiological effect, e.g., to treat a targeted condition (e.g., reduce symptoms of allergic rhinitis), to prevent recurrence of the condition, or to promote immunity against the condition. For certain embodiments, an amount effective to treat or inhibit a viral infection is an amount that will cause a reduction in one or more manifestations of viral infections, such as viral load, rate of virus production, or mortality as compared to untreated control animals.

In certain methods of the present invention, the mucosal tissue is associated with a condition selected from the group consisting of a cervical dysplasia, a papilloma virus infection of the cervix, a low-grade squamous intraepithelial lesion, a high-grade squamous intraepithelial lesion, atypical squamous cells of undetermined significance, a cervical intraepithelial neoplasia, an atopic allergic response, allergic rhinitis, a neoplastic lesion, and a premalignant lesion.

In certain methods of the present invention, the mucosal tissue is on the cervix and the associated condition is selected from the group consisting of cervical dysplasia, high-grade squamous intraepithelial lesions, low-grade squamous intraepithelial lesions, and atypical squamous cells of undetermined significance with the presence of high risk HPV.

In certain methods of the present invention, the mucosal tissue is on the cervix and the associated condition is atypical squamous cells of undetermined significance with the presence of high risk HPV.

In certain methods of the present invention, the mucosal tissue is on the cervix and the associated condition is a papilloma virus infection of the cervix.

The amount of IRM compound that will be therapeutically effective in a specific situation will depend on such things as the dosing regimen, the application site, the particular formulation and the condition being treated. As such, it is generally not practical to identify specific administration amounts herein; however, those skilled in the art will be able to determine appropriate therapeutically effective amounts based on the guidance provided herein, information available in the art pertaining to these compounds, and routine testing.

In some embodiments, the methods of the present invention include administering sufficient formulation to provide a dose of an IRM compound of, for example, from 100 ng/kg to 50 mg/kg to the subject, although in some embodiments the methods may be performed by administering an IRM compound in concentrations outside this range. In some of these embodiments, the method includes administering sufficient formulation to provide a dose of an IRM compound of from 10 µg/kg to 5 mg/kg to the subject, for example, a dose of from 100 µg/kg to 1 mg/kg.

In certain embodiments of the formulations of the invention, the amount or concentration of an IRM compound is at least 0.0001% by weight (wt-%), in other embodiments, at least 0.001 wt-%, in other embodiments at least 0.01 wt-%, and in other embodiments at least 0.1 wt-%, based on the total weight of the aqueous gel. In certain embodiments, the amount of an IRM compound is no greater than 7 wt-%, in other embodiments no greater than 5 wt-%, in other embodiments no greater than 3 wt-%, in other embodiments no greater than 2 wt-%, and in other embodiments no greater than 1 wt-%, based on the total weight of the aqueous gel.

One or more IRM compounds may be present in the formulation as the sole therapeutically active ingredient or in combination with other therapeutic agents. Such other therapeutic agents may include, for example, antibiotics, such as penicillin or tetracycline, corticosteroids, such as hydrocortisone or betamethasone, nonsteroidal antiinflammatories, such as flurbiprofen, ibuprofen, or naproxen, or antivirals, such as acyclovir or valcyclovir.

In some embodiments, the above-described formulations are particularly advantageous for application for a period of time sufficient to obtain a desired therapeutic effect without undesired systemic absorption of the IRM compound.

The IRM of the present invention is present in the gel formulations in combination with a pharmaceutically acceptable acid. Such acid is preferably present in a stoichiometric amount relative to the IRM.

A wide range of pharmaceutically acceptable acids can be used to form salts of IRMs. Examples of such acids are described in Berge et al., J. Pharm. Sciences, 66, 1-19 (1977). Preferred pharmaceutically acceptable acids (e.g., suitable for incorporation in the gels of the present invention or for forming salts of the IRM of the present invention) include, for example, an alkylsulfonic acid, an arylsulfonic acid, a carboxylic acid, a halo acid, sulfuric acid, phosphoric acid, a dicarboxylic acid, a tricarboxylic acid, and combinations thereof. More preferred pharmaceutically acceptable acids include acetic acid, hydrobromic acid, hydrochloric acid, D-gluconic acid, D- and L-lactic acid, methanesulfonic acid, ethanesulfonic acid, propionic acid, benzenesulfonic acid, citric acid, phosphoric acid, succinic acid, sulfuric acid, D- and L-tartaric acid, p-toluenesulfonic acid, and combinations thereof. Particularly preferred salts of the IRM are alkylsulfonate salts (e.g., ethanesulfonate or methanesulfonate).

An IRM compound, and salts thereof, described herein include any of their pharmaceutically acceptable forms, such as isomers (e.g., diastereomers and enantiomers), solvates, polymorphs, and the like. In particular, if a compound is optically active, the invention specifically includes the use of each of the compound's enantiomers as well as racemic combinations of the enantiomers. Also, if a salt is optically active, the invention specifically includes the use of each of the salt's enantiomers as well as racemic combinations of the enantiomers.

IRM Compounds

Preferred IRM compounds suitable for use in the formulations of the invention preferably include compounds having a 2-aminopyridine fused to a five membered nitrogen-containing heterocyclic ring. Other small organic molecules known to function as IRM compounds are also suitable for use in the formulations of the invention.

Certain IRMs are small organic molecules (e.g., molecular weight under about 1000 Daltons, preferably under about 500 Daltons, as opposed to large biologic protein, peptides, and the like) such as those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; and 6,818,650; U.S. Patent Publication Nos. 2004/0091491; 2004/0147543; and 2004/0176367; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, and WO2005/094531.

IRM compounds suitable for use in the invention preferably include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In certain embodiments of the present invention, the IRM is an imidazoquinoline amine.

In certain embodiments of the present invention, the IRM is 1-(2-methylpropyl)-1H-imidazo[4,5-c]quinolin-4-amine (imiquimod).

In certain embodiments of the present invention, the IRM is 2-propylthiazolo[4,5-c]quinolin-4-amine.

In certain embodiments of the present invention, IRM is an amide substituted imidazoquinoline amine. Preferably, the IRM is selected from the group consisting of 3-(4-amino-2-propyl-1H-imidazo[4,5-c]quinolin-1-yl)propionamide, N-[2-(4-amino-7-benzyloxy-2-ethoxymethyl-1H-imidazo[4,5-c]quinolin-1-yl)-1,1-dimethylethyl]acetamide, and 4-(4-amino-2-propyl-1H-imidazo[4,5-c]quinolin-1-yl)-N-propylbutyramide.

In certain embodiments of the present invention, the IRM is N-[2-(4-amino-7-benzyloxy-2-ethoxymethyl-1H-imidazo[4,5-c]quinolin-1-yl)-1,1-dimethylethyl]acetamide.

In certain embodiments of the present invention, the IRM is a urea substituted imidazoquinoline amine. Preferably, the IRM is N-[2-(4-amino-2-ethoxymethyl-1H-imidazo[4,5-c]quinolin-1-yl)ethyl]-N'-isopropylurea.

Exemplary IRM Compounds

In certain embodiments of the present invention the IRM compound can be chosen from 1H-imidazo[4,5-c]quinolin-4-amines defined by one of Formulas I-V below:

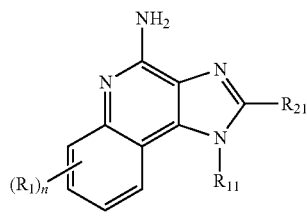

I wherein $R_{11}$ is selected from alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from alkyl of one to four carbon atoms, alkoxy of one to four carbon atoms and halogen, with the proviso that if said benzene ring is substituted by two of said moieties, then said moieties together contain no more than six carbon atoms;

$R_{21}$ is selected from hydrogen, alkyl of one to eight carbon atoms, benzyl, (phenyl)ethyl and phenyl, the benzyl, (phenyl)ethyl or phenyl substituent being optionally substituted on the benzene ring by one or two moieties independently selected from alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently selected from alkoxy of one to four carbon atoms, halogen, and alkyl of one to four carbon atoms, and n is an integer from 0 to 2, with the proviso that if n is 2, then said $R_1$ groups together contain no more than six carbon atoms;

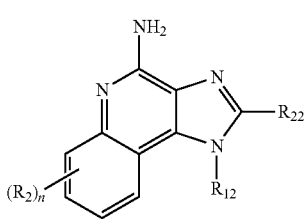

II wherein $R_{12}$ is selected from straight chain or branched chain alkenyl containing two to ten carbon atoms and substituted straight chain or branched chain alkenyl containing two to ten carbon atoms, wherein the substituent is selected from straight chain or branched chain alkyl containing one to four carbon atoms and cycloalkyl containing three to six carbon atoms; and cycloalkyl containing three to six carbon atoms substituted by straight chain or branched chain alkyl containing one to four carbon atoms; and $R_{22}$ is selected from hydrogen, straight chain or branched chain alkyl containing one to eight carbon atoms, benzyl, (phenyl)ethyl and phenyl, the benzyl, (phenyl)ethyl or phenyl substituent being optionally substituted on the benzene ring by one or two moieties independently selected from straight chain or branched chain alkyl containing one to four carbon atoms, straight chain or branched chain alkoxy containing one to four carbon atoms, and halogen, with the proviso that when the benzene ring is substituted by two such moieties, then the moieties together contain no more than six carbon atoms; and each $R_2$ is independently selected from straight chain or branched chain alkoxy containing one to four carbon atoms, halogen, and straight chain or branched chain alkyl containing one to four carbon atoms, and n is an integer from zero to 2, with the proviso that if n is 2, then said $R_2$ groups together contain no more than six carbon atoms;

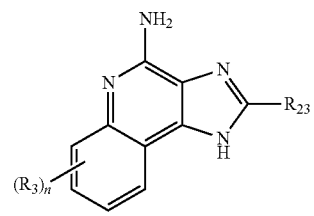

III wherein $R_{23}$ is selected from hydrogen, straight chain or branched chain alkyl of one to eight carbon atoms, benzyl, (phenyl)ethyl and phenyl, the benzyl, (phenyl)ethyl or phenyl substituent being optionally substituted on the benzene ring by one or two moieties independently selected from straight chain or branched chain alkyl of one to four carbon atoms, straight chain or branched chain alkoxy of one to four carbon atoms, and halogen, with the proviso that when the benzene ring is substituted by two such moieties, then the moieties together contain no more than six carbon atoms; and each $R_3$ is independently selected from straight chain or branched chain alkoxy of one to four carbon atoms, halogen, and straight chain or branched chain alkyl of one to four carbon atoms, and n is an integer from zero to 2, with the proviso that if n is 2, then said $R_3$ groups together contain no more than six carbon atoms;

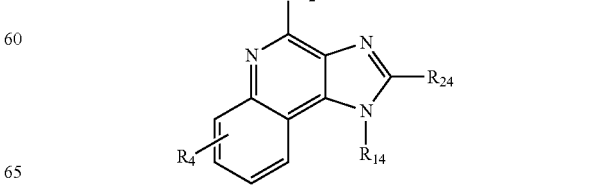

IV wherein

R$_{14}$ is —CHR$_x$R$_y$, wherein R$_y$ is hydrogen or a carbon-carbon bond, with the proviso that when R$_y$ is hydrogen R$_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, or 2-, 3-, or 4-pyridyl, and with the further proviso that when R$_y$ is a carbon-carbon bond R$_y$ and R$_x$ together form a tetrahydrofuranyl group optionally substituted with one or more substituents independently selected from hydroxy and hydroxyalkyl of one to four carbon atoms;

R$_{24}$ is selected from hydrogen, alkyl of one to four carbon atoms, phenyl, and substituted phenyl wherein the substituent is selected from alkyl of one to four carbon atoms, alkoxy of one to four carbon atoms, and halogen; and R$_4$ is selected from hydrogen, straight chain or branched chain alkoxy containing one to four carbon atoms, halogen, and straight chain or branched chain alkyl containing one to four carbon atoms;

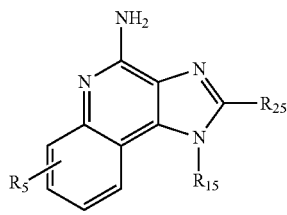

V wherein

R$_{15}$ is selected from hydrogen; straight chain or branched chain alkyl containing one to ten carbon atoms and substituted straight chain or branched chain alkyl containing one to ten carbon atoms, wherein the substituent is selected from cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is selected from cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from alkyl of one to four carbon atoms, alkoxy of one to four carbon atoms, and halogen, with the proviso that when said benzene ring is substituted by two of said moieties, then the moieties together contain no more than six carbon atoms;

R$_{25}$ is

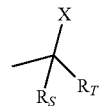

wherein

R$_S$ and R$_T$ are independently selected from hydrogen, alkyl of one to four carbon atoms, phenyl, and substituted phenyl wherein the substituent is selected from alkyl of one to four carbon atoms, alkoxy of one to four carbon atoms, and halogen;

X is selected from alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and R$_5$ is selected from hydrogen, straight chain or branched chain alkoxy containing one to four carbon atoms, halogen, and straight chain or branched chain alkyl containing one to four carbon atoms;

and pharmaceutically acceptable salts of any of the foregoing.

In another embodiment, the IRM compound can be chosen from 6,7 fused cycloalkylimidazopyridine amines defined by Formula VI below:

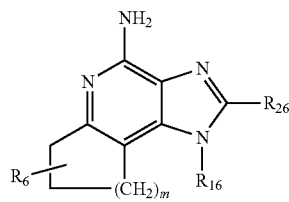

VI wherein m is 1, 2, or 3;

R$_{16}$ is selected from hydrogen; cyclic alkyl of three, four, or five carbon atoms; straight chain or branched chain alkyl containing one to ten carbon atoms and substituted straight chain or branched chain alkyl containing one to ten carbon atoms, wherein the substituent is selected from cycloalkyl containing three to six carbon atoms and cycloalkyl containing three to six carbon atoms substituted by straight chain or branched chain alkyl containing one to four carbon atoms; fluoro- or chloroalkyl containing from one to ten carbon atoms and one or more fluorine or chlorine atoms; straight chain or branched chain alkenyl containing two to ten carbon atoms and substituted straight chain or branched chain alkenyl containing two to ten carbon atoms, wherein the substituent is selected from cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from alkyl of one to four carbon atoms, alkoxy of one to four carbon atoms, and halogen, with the proviso that when said benzene ring is substituted by two of said moieties, then the moieties together contain no more than six carbon atoms; and —$CHR_xR_y$
wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from hydroxy and hydroxyalkyl of one to four carbon atoms;

$R_{26}$ is selected from hydrogen; straight chain or branched chain alkyl containing one to eight carbon atoms; straight chain or branched chain hydroxyalkyl containing one to six carbon atoms; morpholinoalkyl; benzyl; (phenyl)ethyl; and phenyl, the benzyl, (phenyl)ethyl, or phenyl substituent being optionally substituted on the benzene ring by a moiety selected from methyl, methoxy, and halogen; and —$C(R_S)(R_T)(X)$ wherein $R_S$ and $R_T$ are independently selected from hydrogen, alkyl of one to four carbon atoms, phenyl, and substituted phenyl wherein the substituent is selected from alkyl of one to four carbon atoms, alkoxy of one to four carbon atoms, and halogen;

X is selected from alkoxy containing one to four carbon atoms, alkoxyalkyl wherein the alkoxy moiety contains one to four carbon atoms and the alkyl moiety contains one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, alkylthio of one to four carbon atoms, and morpholinoalkyl wherein the alkyl moiety contains one to four carbon atoms; and $R_6$ is selected from hydrogen, fluoro, chloro, straight chain or branched chain alkyl containing one to four carbon atoms, and straight chain or branched chain fluoro- or chloroalkyl containing one to four carbon atoms and at least one fluorine or chlorine atom; and pharmaceutically acceptable salts thereof.

In another embodiment, the IRM compound can be chosen from imidazopyridine amines defined by Formula VII below:

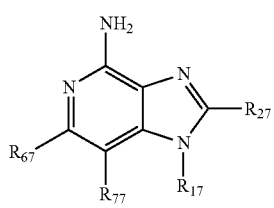

VII wherein $R_{17}$ is selected from hydrogen; —$CH_2R_W$ wherein $R_W$ is selected from straight chain, branched chain, or cyclic alkyl containing one to ten carbon atoms, straight chain or branched chain alkenyl containing two to ten carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, and phenylethyl; and —$CH=CR_ZR_Z$ wherein each $R_Z$ is independently straight chain, branched chain, or cyclic alkyl of one to six carbon atoms;

$R_{27}$ is selected from hydrogen; straight chain or branched chain alkyl containing one to eight carbon atoms; straight chain or branched chain hydroxyalkyl containing one to six carbon atoms; alkoxyalkyl wherein the alkoxy moiety contains one to four carbon atoms and the alkyl moiety contains one to six carbon atoms; benzyl, (phenyl)ethyl and phenyl, the benzyl, (phenyl)ethyl and phenyl being optionally substituted on the benzene ring by a moiety selected from methyl, methoxy, and halogen; and morpholinoalkyl wherein the alkyl moiety contains one to four carbon atoms;

$R_{67}$ and $R_{77}$ are independently selected from hydrogen and alkyl of one to five carbon atoms, with the proviso that $R_{67}$ and $R_{77}$ taken together contain no more than six carbon atoms, and with the further proviso that when $R_{77}$ is hydrogen then $R_{67}$ is other than hydrogen and $R_{27}$ is other than hydrogen or morpholinoalkyl, and with the further proviso that when $R_{67}$ is hydrogen then $R_{77}$ and $R_{27}$ are other than hydrogen; and pharmaceutically acceptable salts thereof.

In another embodiment, the IRM compound can be chosen from 1,2 bridged imidazoquinoline amines defined by Formula VIII below:

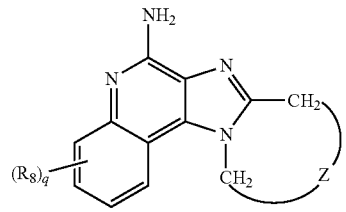

VIII wherein

Z is selected from

—$(CH_2)_p$— wherein p is 1 to 4;

—$(CH_2)_a$—$C(R_DR_E)(CH_2)_b$—, wherein a and b are integers and a+b is 0 to 3, $R_D$ is hydrogen or alkyl of one to four carbon atoms, and $R_E$ is selected from alkyl of one to four carbon atoms, hydroxy, —$OR_F$ wherein $R_F$ is alkyl of one to four carbon atoms, and —$NR_GR'_G$ wherein $R_G$ and $R'_G$ are independently hydrogen or alkyl of one to four carbon atoms; and —$(CH_2)_a$—(Y)—$(CH_2)_b$— wherein a and b are integers and a+b is 0 to 3, and Y is O, S, or —$NR_J$— wherein $R_J$ is hydrogen or alkyl of one to four carbon atoms;

q is 0 or 1; and $R_8$ is selected from alkyl of one to four carbon atoms, alkoxy of one to four carbon atoms, and halogen, and pharmaceutically acceptable salts thereof.

In another embodiment, the IRM compound can be chosen from thiazoloquinoline amines, oxazoloquinoline amines, thiazolopyridine amines, oxazolopyridine amines, thiazolonaphthyridine amines and oxazolonaphthyridine amines defined by Formula IX below:

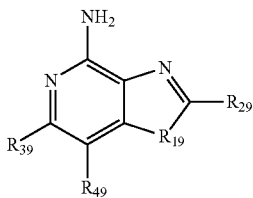

wherein:
R$_{19}$ is selected from oxygen, sulfur and selenium;
R$_{29}$ is selected from
-hydrogen;
-alkyl;
-alkyl-OH;
-haloalkyl;
-alkenyl;
-alkyl-X-alkyl;
-alkyl-X-alkenyl;
-alkenyl-X-alkyl;
-alkenyl-X-alkenyl;
-alkyl-N(R$_{59}$)$_2$;
-alkyl-N$_3$;
-alkyl-O—C(O)—N(R$_{59}$)$_2$;
-heterocyclyl;
-alkyl-X-heterocyclyl;
-alkenyl-X-heterocyclyl;
-aryl;
-alkyl-X-aryl;
-alkenyl-X-aryl;
-heteroaryl;
-alkyl-X-heteroaryl; and
-alkenyl-X-heteroaryl;
R$_{39}$ and R$_{49}$ are each independently:
-hydrogen;
—X-alkyl;
-halo;
-haloalkyl;
—N(R$_{59}$)$_2$;
or when taken together, R$_{39}$ and R$_{49}$ form a fused aromatic, heteroaromatic, cycloalkyl or heterocyclic ring;
X is selected from —O—, —S—, —NR$_{59}$—, —C(O)—, —C(O)O—, —OC(O)—, and a bond; and
each R$_{59}$ is independently H or C$_{1-8}$alkyl;
and pharmaceutically acceptable salts thereof.

In another embodiment, the IRM compound can be chosen from imidazonaphthyridine amines and imidazotetrahydronaphthyridine amines defined by Formulas X and XI below:

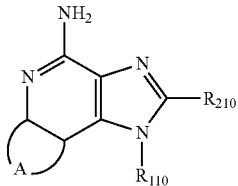

wherein
A is =N—CR=CR—CR=; =CR—N=CR—CR=; =CR—CR=N—CR=; or =CR—CR=CR—N=;

R$_{110}$ is selected from:
-hydrogen;
—C$_{1-20}$ alkyl or C$_{2-20}$ alkenyl that is unsubstituted or substituted by one or more substituents selected from:
-aryl;
-heteroaryl;
-heterocyclyl;
—O—C$_{1-20}$ alkyl;
—O—(C$_{1-20}$ alkyl)$_{0-1}$-aryl;
—O—(C$_{1-20}$ alkyl)$_{0-1}$-heteroaryl;
—O—(C$_{1-20}$ alkyl)$_{0-1}$-heterocyclyl;
—CO—O—C$_{1-20}$ alkyl;
—S(O)$_{0-2}$—C$_{1-20}$ alkyl;
—S(O)$_{0-2}$—(C$_{1-20}$ alkyl)$_{0-1}$-aryl;
—S(O)$_{0-2}$—(C$_{1-20}$ alkyl)$_{0-1}$-heteroaryl;
—S(O)$_{0-2}$—(C$_{1-20}$ alkyl)$_{0-1}$-heterocyclyl;
—N(R$_{310}$)$_2$;
—N$_3$;
oxo;
-halogen;
—NO$_2$;
—OH; and
—SH; and
—C$_{1-20}$ alkyl-NR$_{310}$-Q-X—R$_{410}$ or —C$_{2-20}$ alkenyl-NR$_{310}$-Q-X—R$_{410}$ wherein Q is —CO— or —SO$_2$—; X is a bond, —O— or —NR$_{310}$— and R$_{410}$ is aryl; heteroaryl; heterocyclyl; or —C$_{1-20}$ alkyl or C$_{2-20}$ alkenyl that is unsubstituted or substituted by one or more substituents selected from:
-aryl;
-heteroaryl;
-heterocyclyl;
—O—C$_{1-20}$ alkyl;
—O—(C$_{1-20}$ alkyl)$_{0-1}$-aryl;
—O—(C$_{1-20}$ alkyl)$_{0-1}$-heteroaryl;
—O—(C$_{1-20}$ alkyl)$_{0-1}$-heterocyclyl;
—CO—O—C$_{1-20}$ alkyl;
—S(O)$_{0-2}$—C$_{1-20}$ alkyl;
—S(O)$_{0-2}$—(C$_{1-20}$ alkyl)$_{0-1}$-aryl;
—S(O)$_{0-2}$—(C$_{1-20}$ alkyl)$_{0-1}$-heteroaryl;
—S(O)$_{0-2}$—(C$_{1-20}$ alkyl)$_{0-1}$-heterocyclyl;
—N(R$_{310}$)$_2$;
—NR$_{310}$—CO—O—C$_{1-20}$ alkyl;
—N$_3$;
oxo;
-halogen;
—NO$_2$;
—OH; and
—SH; or R$_{410}$ is

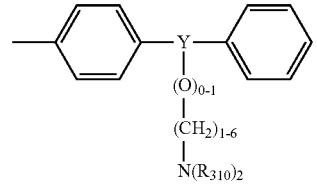

wherein Y is —N— or —CR—;
R$_{210}$ is selected from:
-hydrogen;
—C$_{1-10}$ alkyl;
—C$_{2-10}$ alkenyl;
-aryl;
—C$_{1-10}$ alkyl-O—C$_{1-10}$ alkyl;

—$C_{1-10}$ alkyl-O—$C_{2-10}$ alkenyl; and
—$C_{1-10}$ alkyl or $C_{2-10}$ alkenyl substituted by one or more substituents selected from:
  —OH;
  -halogen;
  —$N(R_{310})_2$;
  —CO—$N(R_{310})_2$;
  —CO—$C_{1-10}$ alkyl;
  —$N_3$;
  -aryl;
  -heteroaryl;
  -heterocyclyl;
  —CO-aryl; and
  —CO-heteroaryl;
each $R_{310}$ is independently selected from hydrogen and $C_{1-10}$ alkyl; and
each R is independently selected from hydrogen, $C_{1-10}$ alkyl, $C_{1-10}$ alkoxy, halogen and trifluoromethyl;

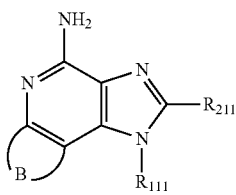

XI wherein
B is —NR—C(R)$_2$—C(R)$_2$—C(R)$_2$—; —C(R)$_2$—NR—C(R)$_2$—C(R)$_2$—; —C(R)$_2$—C(R)$_2$—NR—C(R)$_2$— or —C(R)$_2$—C(R)$_2$—C(R)$_2$—NR—;
$R_{111}$ is selected from:
-hydrogen;
—$C_{1-20}$ alkyl or $C_{2-20}$ alkenyl that is unsubstituted or substituted by one or more substituents selected from:
  -aryl;
  -heteroaryl;
  -heterocyclyl;
  —O—$C_{1-20}$ alkyl;
  —O—($C_{1-20}$ alkyl)$_{0-1}$-aryl;
  —O—($C_{1-20}$ alkyl)$_{0-1}$-heteroaryl;
  —O—($C_{1-20}$ alkyl)$_{0-1}$-heterocyclyl;
  —CO—O—$C_{1-20}$ alkyl;
  —S(O)$_{0-2}$—$C_{1-20}$ alkyl;
  —S(O)$_{0-2}$—($C_{1-20}$ alkyl)$_{0-1}$-aryl;
  —S(O)$_{0-2}$—($C_{1-20}$ alkyl)$_{0-1}$-heteroaryl;
  —S(O)$_{0-2}$—($C_{1-20}$ alkyl)$_{0-1}$-heterocyclyl;
  —$N(R_{311})_2$;
  —$N_3$;
  oxo;
  -halogen;
  —$NO_2$;
  —OH; and
  —SH; and
$C_{1-20}$ alkyl-$NR_{311}$-Q-X—$R_{411}$ or —$C_{2-20}$ alkenyl-$NR_{311}$-Q-X—$R_{411}$ wherein Q is —CO— or —$SO_2$—; X is a bond, —O— or —$NR_{311}$— and $R_{411}$ is aryl; heteroaryl; heterocyclyl; or —$C_{1-20}$ alkyl or $C_{2-20}$ alkenyl that is unsubstituted or substituted by one or more substituents selected from:
  -aryl;
  -heteroaryl;
  -heterocyclyl;
  —O—$C_{1-20}$ alkyl;
  —O—($C_{1-20}$ alkyl)$_{0-1}$-aryl;
  —O—($C_{1-20}$ alkyl)$_{0-10}$-heteroaryl;
  —O—($C_{1-20}$ alkyl)$_{0-1}$-heterocyclyl;
  —CO—O—$C_{1-20}$ alkyl;
  —S(O)$_{0-2}$—$C_{1-20}$ alkyl;
  —S(O)$_{0-2}$—($C_{1-20}$ alkyl)$_{0-1}$-aryl;
  —S(O)$_{0-2}$—($C_{1-20}$ alkyl)$_{0-1}$-heteroaryl;
  —S(O)$_{0-2}$—($C_{1-20}$ alkyl)$_{0-1}$-heterocyclyl;
  —$N(R_{311})_2$;
  —$NR_{311}$—CO—O—$C_{1-20}$ alkyl;
  —$N_3$;
  oxo;
  -halogen;
  —$NO_2$;
  —OH; and
  —SH; or $R_{411}$ is

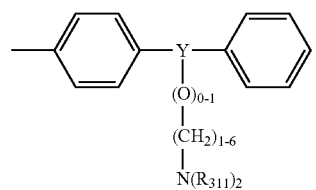

wherein Y is —N— or —CR—;
$R_{211}$ is selected from:
-hydrogen;
—$C_{1-10}$ alkyl;
—$C_{2-10}$ alkenyl;
-aryl;
—$C_{1-10}$ alkyl-O—$C_{1-10}$-alkyl;
—$C_{1-10}$ alkyl-O—$C_{2-10}$ alkenyl; and
—$C_{1-10}$ alkyl or $C_{2-10}$ alkenyl substituted by one or more substituents selected from:
  —OH;
  -halogen;
  —$N(R_{311})_2$;
  —CO—$N(R_{311})_2$;
  —CO—$C_{1-10}$ alkyl;
  —$N_3$;
  -aryl;
  -heteroaryl;
  -heterocyclyl;
  —CO-aryl; and
  —CO-heteroaryl;
each $R_{311}$ is independently selected from hydrogen and $C_{1-10}$ alkyl; and
each R is independently selected from hydrogen, $C_{1-10}$ alkyl, $C_{1-10}$ alkoxy, halogen, and trifluoromethyl;
and pharmaceutically acceptable salts thereof.
In another embodiment, the IRM compound can be chosen from 1H-imidazo[4,5-c]quinolin-4-amines and tetrahydro-1H-imidazo[4,5-c]quinolin-4-amines defined by Formulas XII, XIII and XIV below:

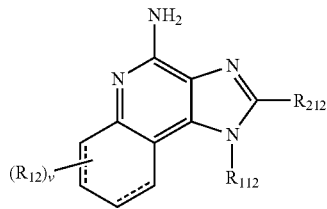

XII wherein $R_{112}$ is -alkyl-$NR_{312}$—CO—$R_{412}$ or -alkenyl-$NR_{312}$—CO—$R_{412}$ wherein $R_{412}$ is aryl, heteroaryl, alkyl or alkenyl, each of which may be unsubstituted or substituted by one or more substituents selected from:
- -alkyl;
- -alkenyl;
- -alkynyl;
- -(alkyl)$_{0-1}$-aryl;
- -(alkyl)$_{0-1}$-(substituted aryl);
- -(alkyl)$_{0-1}$-heteroaryl;
- -(alkyl)$_{0-1}$-(substituted heteroaryl);
- —O-alkyl;
- —O-(alkyl)$_{0-1}$-aryl;
- —O-(alkyl)$_{0-1}$-(substituted aryl);
- —O-(alkyl)$_{0-1}$-heteroaryl;
- —O-(alkyl)$_{0-1}$-(substituted heteroaryl);
- —CO-aryl;
- —CO-(substituted aryl);
- —CO-heteroaryl;
- —CO-(substituted heteroaryl);
- —COOH;
- —CO—O-alkyl;
- —CO-alkyl;
- —S(O)$_{0-2}$-alkyl;
- —S(O)$_{0-2}$-(alkyl)$_{0-1}$-aryl;
- —S(O)$_{0-2}$-(alkyl)$_{0-1}$-(substituted aryl);
- —S(O)$_{0-2}$-(alkyl)$_{0-1}$-heteroaryl;
- —S(O)$_{0-2}$-(alkyl)$_{0-1}$-(substituted heteroaryl);
- —P(O)(O$R_{312}$)$_2$;
- —$NR_{312}$—CO—O-alkyl;
- —$N_3$;
- -halogen;
- —$NO_2$;
- —CN;
- -haloalkyl;
- 13 O-haloalkyl;
- —CO-haloalkyl;
- —OH;
- —SH; and in the case that $R_{412}$ is alkyl, alkenyl, or heterocyclyl, oxo; or $R_{412}$ is

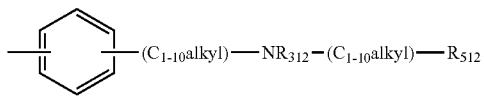

wherein $R_{512}$ is an aryl, (substituted aryl), heteroaryl, (substituted heteroaryl), heterocyclyl or (substituted heterocyclyl) group;

$R_{212}$ is selected from:
- -hydrogen;
- -alkyl;
- -alkenyl;
- -aryl;
- -(substituted aryl);
- -heteroaryl;
- -(substituted heteroaryl);
- -heterocyclyl;
- -(substituted heterocyclyl);
- -alkyl-O-alkyl;
- -alkyl-O-alkenyl; and
- -alkyl or alkenyl substituted by one or more substituents selected from:
  - —OH;
  - -halogen;
  - —N($R_{312}$)$_2$;
  - —CO—N($R_{312}$)$_2$;
  - —CO—$C_{1-10}$ alkyl;
  - —CO—O—$C_{1-10}$ alkyl;
  - —$N_3$;
  - -aryl;
  - -(substituted aryl);
  - -heteroaryl;
  - -(substituted heteroaryl);
  - -heterocyclyl;
  - -(substituted heterocyclyl);
  - —CO-aryl; and
  - —CO-heteroaryl;

each $R_{312}$ is independently selected from hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

v is 0 to 4;

and each $R_{12}$ present is independently selected from $C_{1-10}$ alkyl, $C_{1-10}$ alkoxy, halogen, and trifluoromethyl;

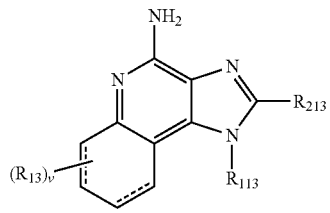

XIII wherein $R_{113}$ is -alkyl-$NR_{313}$—SO$_2$—X—$R_{413}$ or -alkenyl-$NR_{313}$—SO$_2$—X—$R_{413}$;

X is a bond or —$NR_{513}$—;

$R_{413}$ is aryl, heteroaryl, heterocyclyl, alkyl or alkenyl, each of which may be unsubstituted or substituted by one or more substituents selected from:
- -alkyl;
- -alkenyl;
- -aryl;
- -heteroaryl;
- -heterocyclyl;
- -substituted cycloalkyl;
- -substituted aryl;
- -substituted heteroaryl;
- -substituted heterocyclyl;
- —O-alkyl;
- —O-(alkyl)$_{0-1}$-aryl;
- —O-(alkyl)$_{0-1}$-substituted aryl;
- —O-(alkyl)$_{0-1}$-heteroaryl;
- —O-(alkyl)$_{0-1}$-substituted heteroaryl;
- —O-(alkyl)$_{0-1}$-heterocyclyl;
- —O-(alkyl)$_{0-1}$-substituted heterocyclyl;
- —COOH;
- —CO—O-alkyl;
- —CO-alkyl;
- —S(O)$_{0-2}$-alkyl;
- —S(O)$_{0-2}$-(alkyl)$_{0-1}$-aryl;
- —S(O)$_{0-2}$-(alkyl)$_{0-1}$-substituted aryl;
- —S(O)$_{0-2}$-(alkyl)$_{0-1}$-heteroaryl;
- —S(O)$_{0-2}$-(alkyl)$_{0-1}$-substituted heteroaryl;
- —S(O)$_{0-2}$-(alkyl)$_{0-1}$-heterocyclyl;
- —S(O)$_{0-2}$-(alkyl)$_{0-1}$-substituted heterocyclyl;
- -(alkyl)$_{0-1}$-$NR_{313}R_{313}$;
- -(alkyl)$_{0-1}$-$NR_{313}$—CO—O-alkyl;
- -(alkyl)$_{0-1}$-$NR_{313}$—CO-alkyl;

-(alkyl)$_{0-1}$-NR$_{313}$—CO-aryl;
-(alkyl)$_{0-1}$-NR$_{313}$—CO-substituted aryl;
-(alkyl)$_{0-1}$-NR$_{313}$—CO-heteroaryl;
-(alkyl)$_{0-1}$-NR$_{313}$—CO-substituted heteroaryl;
—N$_3$;
-halogen;
-haloalkyl;
-haloalkoxy;
—CO-haloalkyl;
—CO-haloalkoxy;
—NO$_2$;
—CN;
—OH;
—SH; and in the case that R$_{413}$ is alkyl, alkenyl, or heterocyclyl, oxo;
R$_{213}$ is selected from:
-hydrogen;
-alkyl;
-alkenyl;
-aryl;
-substituted aryl;
-heteroaryl;
-substituted heteroaryl;
-alkyl-O-alkyl;
-alkyl-O-alkenyl; and
-alkyl or alkenyl substituted by one or more substituents selected from:
 —OH;
 -halogen;
 —N(R$_{313}$)$_2$;
 —CO—N(R$_{313}$)$_2$;
 —CO—C$_{1-10}$ alkyl;
 —CO—O—C$_{1-10}$ alkyl;
—N$_3$;
 -aryl;
 -substituted aryl;
 -heteroaryl;
 -substituted heteroaryl;
 -heterocyclyl;
 -substituted heterocyclyl;
 —CO-aryl;
 —CO-(substituted aryl);
 —CO-heteroaryl; and
 —CO-(substituted heteroaryl);
each R$_{313}$ is independently selected from hydrogen and C$_{1-10}$ alkyl; or when X is a bond R$_{313}$ and R$_{413}$ can join to form a 3 to 7 membered heterocyclic or substituted heterocyclic ring;
R$_{513}$ is selected from hydrogen and C$_{1-10}$ alkyl, or R$_{413}$ and R$_{513}$ can combine to form a 3 to 7 membered heterocyclic or substituted heterocyclic ring;
v is 0 to 4;
and each R$_{13}$ present is independently selected from C$_{1-10}$ alkyl, C$_{1-10}$ alkoxy, halogen, and trifluoromethyl;

XIV

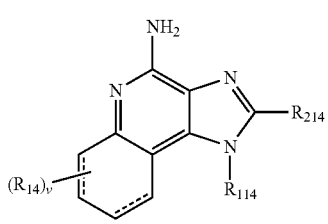

wherein
R$_{114}$ is -alkyl-NR$_{314}$—CY—NR$_{514}$—X—R$_{414}$ or
-alkenyl-NR$_{314}$—CY—NR$_{514}$—X—R$_{414}$
wherein
Y is =O or =S;
X is a bond, —CO— or —SO$_2$—;
R$_{414}$ is aryl, heteroaryl, heterocyclyl, alkyl or alkenyl, each of which may be unsubstituted or substituted by one or more substituents selected from:
-alkyl;
-alkenyl;
-aryl;
-heteroaryl;
-heterocyclyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-substituted aryl;
—S(O)$_{0-2}$-(alkyl)$_{0-1}$-heteroaryl;
—S(O)$_{0-2}$-(alkyl)$_{0-1}$-substituted heteroaryl;
—S(O)$_{0-2}$-(alkyl)$_{0-1}$-heterocyclyl;
—S(O)$_{0-2}$-(alkyl)$_{0-1}$-substituted heterocyclyl;
-(alkyl)$_{0-1}$-NR$_{314}$R$_{314}$;
-(alkyl)$_{0-1}$-NR$_{314}$—CO—O-alkyl;
-(alkyl)$_{0-1}$-NR$_{314}$—CO-alkyl;
-(alkyl)$_{0-1}$-NR$_{314}$—CO-aryl;
-(alkyl)$_{0-1}$-NR$_{314}$—CO-substituted aryl;
-(alkyl)$_{0-1}$-NR$_{314}$—CO-heteroaryl;
-(alkyl)$_{0-1}$-NR$_{314}$—CO-substituted heteroaryl;
—N$_3$;
-halogen;
-haloalkyl;
-haloalkoxy;
—CO-haloalkoxy;
—NO$_2$;
—CN;
—OH;
—SH; and, in the case that R$_{414}$ is alkyl, alkenyl or heterocyclyl, oxo; with the proviso that when X is a bond R$_{414}$ can additionally be hydrogen;
R$_{214}$ is selected from:
-hydrogen;
-alkyl;
-alkenyl;
-aryl;
-substituted aryl;
-heteroaryl;
-substituted heteroaryl;
-alkyl-O-alkyl;
-alkyl-O-alkenyl; and
-alkyl or alkenyl substituted by one or more substituents selected from:
 —OH;
 -halogen;
 —N(R$_{314}$)$_2$;

—CO—N($R_{314}$)$_2$;
—CO—C$_{1-10}$ alkyl;
—CO—O—C$_{1-10}$ alkyl;
—N$_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);

each $R_{314}$ is independently selected from hydrogen and C$_{1-10}$ alkyl;

$R_{514}$ is selected from hydrogen and C$_{1-10}$ alkyl, or $R_{414}$ and $R_{514}$ can combine to form a 3 to 7 membered heterocyclic or substituted heterocyclic ring;

v is 0 to 4;

and each $R_{14}$ present is independently selected from C$_{1-10}$ alkyl, C$_{1-10}$ alkoxy, halogen, and trifluoromethyl;
and pharmaceutically acceptable salts thereof.

In another embodiment, the IRM compound can be chosen from 1H-imidazo[4,5-c]quinolin-4-amines and tetrahydro-1H-imidazo[4,5-c]quinolin-4-amines defined by Formulas XV, XVI, XVII, XVIII, XIX, XX, XXI, XXII, XXIII, XXIV, XXV, and XXVI below:

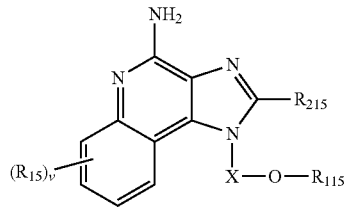

XV

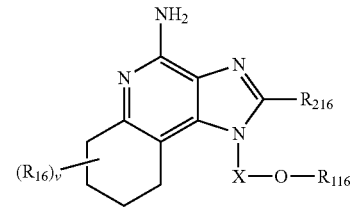

XVI wherein: X is —CHR$_{515}$—, —CHR$_{515}$-alkyl-, or —CHR$_{515}$-alkenyl-;

$R_{115}$ is selected from:
—$R_{415}$—CR$_{315}$—Z—R$_{615}$-alkyl;
—$R_{415}$—CR$_{315}$—Z—R$_{615}$-alkenyl;
—$R_{415}$—CR$_{315}$—Z—R$_{615}$-aryl;
—$R_{415}$—CR$_{315}$—Z—R$_{615}$-heteroaryl;
—$R_{415}$—CR$_{315}$—Z—R$_{615}$-heterocyclyl;
—$R_{415}$—CR$_{315}$—Z—H;
—$R_{415}$—NR$_{715}$—CR$_{315}$—R$_{615}$-alkyl;
—$R_{415}$—NR$_{715}$—CR$_{315}$—R$_{615}$-alkenyl;
—$R_{415}$—NR$_{715}$—CR$_{315}$—R$_{615}$-aryl;
—$R_{415}$—NR$_{715}$—CR$_{315}$—R$_{615}$-heteroaryl;
—$R_{415}$—NR$_{715}$—CR$_{315}$—R$_{615}$-heterocyclyl; and
—$R_{415}$—NR$_{715}$—CR$_{315}$—R$_{815}$;

Z is —NR$_{515}$—, —O—, or —S—;

$R_{215}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and -alkyl or alkenyl substituted by one or more substituents selected from:
—OH;
-halogen;
—N($R_{515}$)$_2$;
—CO—N($R_{515}$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

$R_{315}$ is =O or =S;

$R_{415}$ is alkyl or alkenyl, which may be interrupted by one or more —O— groups;

each $R_{515}$ is independently H or C$_{1-10}$ alkyl;

$R_{615}$ is a bond, alkyl, or alkenyl, which may be interrupted by one or more —O— groups;

$R_{715}$ is H, C$_{1-10}$ alkyl, or arylalkyl; or $R_{415}$ and $R_{715}$ can join together to form a ring;

$R_{815}$ is H or C$_{1-10}$ alkyl; or $R_{715}$ and $R_{815}$ can join together to form a ring;

Y is —O— or —S(O)$_{0-2}$—;

v is 0 to 4; and each $R_{15}$ present is independently selected from C$_{1-10}$ alkyl, C$_{1-10}$ alkoxy, hydroxy, halogen, and trifluoromethyl;

wherein: X is —CHR$_{516}$—, —CHR$_{516}$-alkyl-, or —CHR$_{516}$-alkenyl-;

$R_{116}$ is selected from:
—$R_{416}$—CR$_{316}$—Z—R$_{616}$-alkyl;
—$R_{416}$—CR$_{316}$—Z—R$_{616}$-alkenyl;
—$R_{416}$—CR$_{316}$—Z—R$_{616}$-aryl;
—$R_{416}$—CR$_{316}$—Z—R$_{616}$-heteroaryl;
—$R_{416}$—CR$_{316}$—Z—R$_{616}$-heterocyclyl;
—$R_{416}$—CR$_{316}$—Z—H;
—$R_{416}$—NR$_{716}$—CR$_{316}$—R$_{616}$-alkyl;
—$R_{416}$—NR$_{716}$—CR$_{316}$—R$_{616}$-alkenyl;
—$R_{416}$—NR$_{716}$—CR$_{316}$—R$_{616}$-aryl;
—$R_{416}$—NR$_{716}$—CR$_{316}$—R$_{616}$-heteroaryl;
—$R_{416}$—NR$_{716}$—CR$_{316}$—R$_{616}$-heterocyclyl; and
—$R_{416}$—NR$_{716}$—CR$_{316}$—R$_{816}$;

Z is —NR$_{516}$—, —O—, or —S—;

$R_{216}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and -alkyl or alkenyl substituted by one or more substituents selected from:
  —OH;
  -halogen;
  —N($R_{516}$)$_2$;
  —CO—N($R_{516}$)$_2$;
  —CO—$C_{1-10}$ alkyl;
  —CO—O—$C_{1-10}$ alkyl;
  —$N_3$;
  -aryl;
  -heteroaryl;
  -heterocyclyl;
  —CO-aryl; and
  —CO-heteroaryl;
$R_{316}$ is =O or =S;
$R_{416}$ is alkyl or alkenyl, which may be interrupted by one or more —O— groups;
each $R_{516}$ is independently H or $C_{1-10}$ alkyl;
$R_{616}$ is a bond, alkyl, or alkenyl, which may be interrupted by one or more —O— groups;
$R_{716}$ is H, $C_{1-10}$ alkyl, arylalkyl; or $R_{416}$ and $R_{716}$ can join together to form a ring;
$R_{816}$ is H or $C_{1-10}$ alkyl; or $R_{716}$ and $R_{816}$ can join together to form a ring;
Y is —O— or —S(O)$_{0-2}$—;
v is 0 to 4; and
each $R_{16}$ present is independently selected from $C_{1-10}$ alkyl, $C_{1-10}$ alkoxy, hydroxy, halogen, and trifluoromethyl;

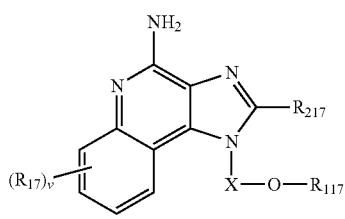

XVII wherein: X is —CH$R_{317}$—, —CH$R_{317}$-alkyl-, or —CH$R_{317}$-alkenyl-;
$R_{117}$ is selected from:
  -alkenyl;
  -aryl; and
  —$R_{417}$-aryl;
$R_{217}$ is selected from:
  -hydrogen;
  -alkyl;
  -alkenyl;
  -aryl;
  -heteroaryl;
  -heterocyclyl;
  -alkyl-Y-alkyl;
  -alkyl-Y-alkenyl;
  -alkyl-Y-aryl; and
  -alkyl or alkenyl substituted by one or more substituents selected from:
    —OH;
    -halogen;
    —N($R_{317}$)$_2$;
    —CO—N($R_{317}$)$_2$;
    —CO—$C_{1-10}$ alkyl;
    —CO—O—$C_{1-10}$ alkyl;
    —$N_3$;
    -aryl;
    -heteroaryl;
    -heterocyclyl;
    —CO-aryl; and
    —CO-heteroaryl;
$R_{417}$ is alkyl or alkenyl, which may be interrupted by one or more —O— groups;
each $R_{317}$ is independently H or $C_{1-10}$ alkyl;
each Y is independently —O— or —S(O)$_{0-2}$—;
v is 0 to 4; and
each $R_{17}$ present is independently selected from $C_{1-10}$ alkyl, $C_{1-10}$ alkoxy, hydroxy, halogen, and trifluoromethyl;

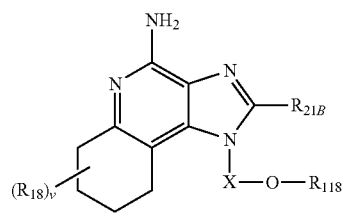

XVIII wherein: X is —CH$R_{318}$—, —CH$R_{318}$-alkyl-, or —CH$R_{318}$-alkenyl-;
$R_{118}$ is selected from:
  -aryl;
  -alkenyl; and
  —$R_{418}$-aryl;
$R_{218}$ is selected from:
  -hydrogen;
  -alkyl;
  -alkenyl;
  -aryl;
  -heteroaryl;
  -heterocyclyl;
  -alkyl-Y-alkyl;
  -alkyl-Y-aryl;
  -alkyl-Y-alkenyl; and
  -alkyl or alkenyl substituted by one or more substituents selected from:
    —OH;
    -halogen;
    —N($R_{318}$)$_2$;
    —CO—N($R_{318}$)$_2$;
    —CO—$C_{1-10}$ alkyl;
    —CO—O—$C_{1-10}$ alkyl;
    —$N_3$;
    -aryl;
    -heteroaryl;
    -heterocyclyl;
    —CO-aryl; and
    —CO-heteroaryl;
$R_{418}$ is alkyl or alkenyl, which may be interrupted by one or more —O— groups;
each $R_{318}$ is independently H or $C_{1-10}$ alkyl;
each Y is independently —O— or —S(O)$_{0-2}$—;
v is 0 to 4; and
each $R_{18}$ present is independently selected $C_{1-10}$ alkyl, $C_{1-10}$ alkoxy, hydroxy, halogen, and trifluoromethyl;

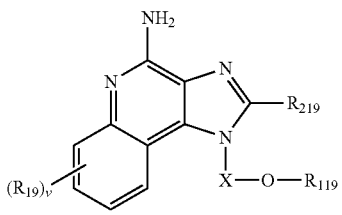

XIX wherein: X is —CHR$_{319}$—, —CHR$_{319}$-alkyl-, or —CHR$_{319}$-alkenyl-;
R$_{119}$ is selected from:
- -heteroaryl;
- -heterocyclyl;
- —R$_{419}$-heteroaryl; and
- —R$_{419}$-heterocyclyl;

R$_{219}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —N(R$_{319}$)$_2$;
  - —CO—N(R$_{319}$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

R$_{419}$ is alkyl or alkenyl, which may be interrupted by one or more —O— groups;
each R$_{319}$ is independently H or C$_{1-10}$ alkyl;
each Y is independently —O— or —S(O)$_{0-2}$—;
v is 0 to 4; and
each R$_{19}$ present is independently selected from C$_{1-10}$ alkyl, C$_{1-10}$ alkoxy, hydroxy, halogen, and trifluoromethyl;

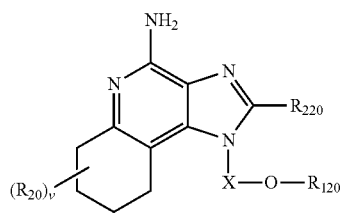

XX wherein: X is —CHR$_{320}$—, —CHR$_{320}$-alkyl-, or —CHR$_{320}$-alkenyl-;

R$_{120}$ is selected from:
- -heteroaryl;
- -heterocyclyl;
- —R$_{420}$-heteroaryl; and
- —R$_{420}$-heterocyclyl;

R$_{220}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —N(R$_{320}$)$_2$;
  - —CO—N(R$_{320}$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

R$_{420}$ is alkyl or alkenyl, which may be interrupted by one or more —O— groups;
each R$_{320}$ is independently H or C$_{1-10}$ alkyl;
each Y is independently —O— or —S(O)$_{0-2}$—;
v is 0 to 4; and
each R$_{20}$ present is independently selected from C$_{1-10}$ alkyl, C$_{1-10}$ alkoxy, hydroxy, halogen, and trifluoromethyl;

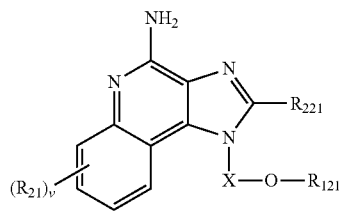

XXI wherein: X is —CHR$_{521}$—, —CHR$_{521}$-alkyl-, or —CHR$_{521}$-alkenyl-;
R$_{121}$ is selected from:
- —R$_{421}$—NR$_{321}$—SO$_2$—R$_{621}$-alkyl;
- —R$_{421}$—NR$_{321}$—SO$_2$—R$_{621}$-alkenyl;
- —R$_{421}$—NR$_{321}$—SO$_2$—R$_{621}$-aryl;
- —R$_{421}$—NR$_{321}$—SO$_2$—R$_{621}$-heteroaryl;
- —R$_{421}$—NR$_{321}$—SO$_2$—R$_{621}$-heterocyclyl;
- —R$_{421}$—NR$_{321}$—SO$_2$—R$_{721}$;
- —R$_{421}$—NR$_{321}$—SO$_2$—NR$_{521}$—R$_{621}$-alkyl;
- —R$_{421}$—NR$_{321}$—SO$_2$—NR$_{521}$—R$_{621}$-alkenyl;
- —R$_{421}$—NR$_{321}$—SO$_2$—NR$_{521}$—R$_{621}$-aryl;
- —R$_{421}$—NR$_{321}$—SO$_2$—NR$_{521}$—R$_{621}$-heteroaryl;
- —R$_{421}$—NR$_{321}$—SO$_2$—NR$_{521}$—R$_{621}$-heterocyclyl; and
- —R$_{421}$—NR$_{321}$—SO$_2$—NH$_2$;

$R_{221}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —N($R_{521}$)$_2$;
  - —CO—N($R_{521}$)$_2$;
  - —CO—C$_{1-10}$ alkyl;
  - —CO—O—C$_{1-10}$ alkyl;
  - —$_3$;
  - -aryl;
  - -heteroaryl;
  - -heterocyclyl;
  - —CO-aryl; and
  - —CO-heteroaryl;

Y is —O— or —S(O)$_{0-2}$—;
$R_{321}$ is H, C$_{1-10}$ alkyl, or arylalkyl;
each $R_{421}$ is independently alkyl or alkenyl, which may be interrupted by one or more —O— groups; or $R_{321}$ and $R_{421}$ can join together to form a ring;
each $R_{521}$ is independently H, C$_{1-10}$ alkyl, or C$_{2-10}$ alkenyl;
$R_{621}$ is a bond, alkyl, or alkenyl, which may be interrupted by one or more —O— groups;
$R_{721}$ is C$_{1-10}$ alkyl; or $R_{321}$ and $R_{721}$ can join together to form a ring;
v is 0 to 4; and
each $R_{21}$ present is independently selected from C$_{1-10}$ alkyl, C$_{1-10}$ alkoxy, hydroxy, halogen, and trifluoromethyl;

$R_{222}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —N($R_{522}$)$_2$;
  - —CO—N($R_{522}$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

Y is —O— or —S(O)$_{0-2}$—;
$R_{322}$ is H, C$_{1-10}$ alkyl, or arylalkyl;
each $R_{422}$ is independently alkyl or alkenyl, which may be interrupted by one or more —O— groups; or $R_{322}$ and $R_{422}$ can join together to form a ring;
each $R_{522}$ is independently H, C$_{1-10}$ alkyl, or C$_{2-10}$ alkenyl;
$R_{622}$ is a bond, alkyl, or alkenyl, which may be interrupted by one or more —O— groups;
$R_{722}$ is C$_{1-10}$ alkyl; or $R_{322}$ and $R_{722}$ can join together to form a ring;
v is 0 to 4; and
each $R_{22}$ present is independently selected from C$_{1-10}$ alkyl, C$_{1-10}$ alkoxy, hydroxy, halogen, and trifluoromethyl;

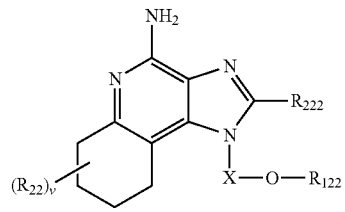

XXII

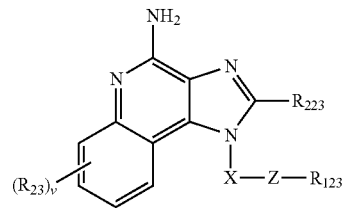

XXIII wherein: X is —CHR$_{522}$—, —CHR$_{522}$-alkyl-, or —CHR$_{522}$-alkenyl-;
$R_{122}$ is selected from:
- —$R_{422}$—NR$_{322}$—SO$_2$—$R_{622}$-alkyl;
- —$R_{422}$—NR$_{322}$—SO$_2$—$R_{622}$-alkenyl;
- —$R_{422}$—NR$_{322}$—SO$_2$—$R_{622}$-aryl;
- —$R_{422}$—NR$_{322}$—SO$_2$—$R_{622}$-heteroaryl;
- —$R_{422}$—NR$_{322}$—SO$_2$—$R_{622}$-heterocyclyl;
- —$R_{422}$—NR$_{322}$—SO$_2$—$R_{722}$;
- —$R_{422}$—NR$_{322}$—SO$_2$—NR$_{522}$—$R_{622}$-alkyl;
- —$R_{422}$—NR$_{322}$—SO$_2$—NR$_{522}$—$R_{622}$-alkenyl;
- —$R_{422}$—NR$_{322}$—SO$_2$—NR$_{522}$—$R_{622}$-alkyl;
- —$R_{422}$—NR$_{322}$—SO$_2$—NR$_{522}$—$R_{622}$-heteroaryl;
- —$R_{422}$—NR$_{322}$—SO$_2$—NR$_{522}$—$R_{622}$-heterocyclyl; and
- —$R_{422}$—NR$_{322}$—SO$_2$—NH$_2$;

wherein: X is —CHR$_{323}$—, —CHR$_{323}$-alkyl-, or —CHR$_{323}$-alkenyl-;
Z is —S—, —SO—, or —SO$_2$—;
$R_{123}$ is selected from:
- -alkyl;
- -aryl;
- -heteroaryl;
- -heterocyclyl;
- -alkenyl;
- —$R_{423}$-aryl;
- —$R_{423}$-heteroaryl; and
- —$R_{423}$-heterocyclyl;
$R_{223}$ is selected from:
- -hydrogen;
- -alkyl;
- -alkenyl;

-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N($R_{323}$)$_2$;
—CO—N($R_{323}$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;
each $R_{323}$ is independently H or $C_{1-10}$ alkyl;
each $R_{423}$ is independently alkyl or alkenyl;
each Y is independently —O— or —S(O)$_{0-2}$—;
v is 0 to 4; and
each $R_{23}$ present is independently selected from $C_{1-10}$ alkyl, $C_{1-10}$ alkoxy, hydroxy, halogen, and trifluoromethyl;

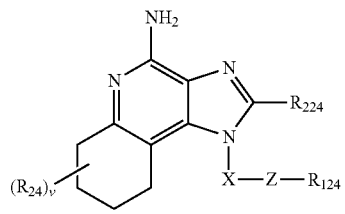

XXIV wherein: X is —CH$R_{324}$—, —CH$R_{324}$-alkyl-, or —CH$R_{324}$-alkenyl-;
Z is —S—, —SO—, or —SO$_2$—;
$R_{124}$ is selected from:
-alkyl;
-aryl;
-heteroaryl;
-heterocyclyl;
-alkenyl;
—$R_{424}$-aryl;
—$R_{424}$-heteroaryl; and
—$R_{424}$-heterocyclyl;
$R_{224}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N($R_{324}$)$_2$;
—CO—N($R_{324}$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;
each $R_{324}$ is independently H or $C_{1-10}$ alkyl;
each $R_{424}$ is independently alkyl or alkenyl;
each Y is independently —O— or —S(O)$_{0-2}$—;
v is 0 to 4; and
each $R_{24}$ present is independently selected from $C_{1-10}$ alkyl, $C_{1-10}$ alkoxy, hydroxy, halogen, and trifluoromethyl;

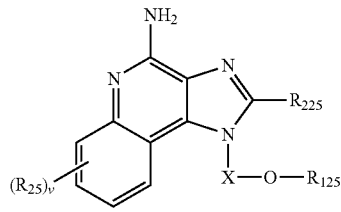

XXV wherein: X is —CH$R_{525}$—, —CH$R_{525}$-alkyl-, or —CH$R_{525}$-alkenyl-;
$R_{125}$ is selected from:
—$R_{425}$—N$R_{825}$—C$R_{325}$—N$R_{525}$—Z—$R_{625}$-alkyl;
—$R_{425}$—N$R_{825}$—C$R_{325}$—N$R_{525}$—Z—$R_{625}$-alkenyl;
—$R_{425}$—N$R_{825}$—C$R_{325}$—N$R_{525}$—Z—$R_{625}$-aryl;
—$R_{425}$—N$R_{825}$—C$R_{325}$—N$R_{525}$—Z—$R_{625}$-heteroaryl;
—$R_{425}$—N$R_{825}$—C$R_{325}$—N$R_{525}$—Z—$R_{625}$-heterocyclyl;
—$R_{425}$—N$R_{825}$—C$R_{325}$—N$R_{525}R_{725}$;
—$R_{425}$—N$R_{825}$—C$R_{325}$—N$R_{925}$—Z—$R_{625}$-alkyl;
—$R_{425}$—N$R_{825}$—C$R_{325}$—N$R_{925}$—Z—$R_{625}$-alkenyl;
—$R_{425}$—N$R_{825}$—C$R_{325}$—N$R_{925}$—Z—$R_{625}$-aryl;
—$R_{425}$—N$R_{825}$—C$R_{325}$—N$R_{925}$—Z—$R_{625}$-heteroaryl; and
—$R_{425}$—N$R_{825}$—C$R_{325}$—N$R_{925}$—Z—$R_{625}$-heterocyclyl;
$R_{225}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N($R_{525}$)$_2$;
—CO—N($R_{525}$)$_2$;
—CO—$C_{1-10}$ alkyl;
—CO—O—$C_{1-10}$ alkyl;
—$N_3$;
-aryl;
-heteroaryl;
-heterocyclyl;

—CO-aryl; and
—CO-heteroaryl;
each $R_{325}$ is =O or =S;
each $R_{425}$ is independently alkyl or alkenyl, which may be interrupted by one or more —O— groups;
each $R_{525}$ is independently H or $C_{1-10}$ alkyl;
$R_{625}$ is a bond, alkyl, or alkenyl, which may be interrupted by one or more —O— groups;
$R_{725}$ is H or $C_{1-10}$ alkyl which may be interrupted by a hetero atom, or $R_{725}$ can join with $R_{525}$ to form a ring;
$R_{825}$ is H, $C_{1-10}$ alkyl, or arylalkyl; or $R_{425}$ and $R_{825}$ can join together to form a ring;
$R_{925}$ is $C_{1-10}$ alkyl which can join together with $R_{825}$ to form a ring; each Y is independently —O— or —S(O)$_{0-2}$—;
Z is a bond, —CO—, or —SO$_2$—;
v is 0 to 4; and
each $R_{25}$ present is independently selected $C_{1-10}$ alkyl, $C_{1-10}$ alkoxy, hydroxy, halogen, and trifluoromethyl;

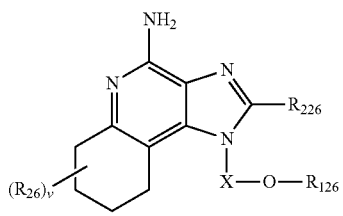

XXVI wherein: X is —CHR$_{526}$—, —CHR$_{526}$-alkyl-, or —CHR$_{526}$-alkenyl-;
$R_{126}$ is selected from:
—R$_{426}$—NR$_{826}$—CR$_{326}$—NR$_{526}$—Z—R$_{626}$-alkyl;
—R$_{426}$—NR$_{826}$—CR$_{326}$—NR$_{526}$—Z—R$_{626}$-alkenyl;
—R$_{426}$—NR$_{826}$—CR$_{326}$—NR$_{526}$—Z—R$_{626}$-aryl;
—R$_{426}$—NR$_{826}$—CR$_{326}$—NR$_{526}$—Z—R$_{626}$-heteroaryl;
—R$_{426}$—NR$_{826}$—CR$_{326}$—NR$_{526}$—Z—R$_{626}$-heterocyclyl;
—R$_{426}$—NR$_{826}$—CR$_{326}$—NR$_{526}$R$_{726}$;
—R$_{426}$—NR$_{826}$—CR$_{326}$—NR$_{926}$—Z—R$_{626}$-alkyl;
—R$_{426}$—NR$_{826}$—CR$_{326}$—NR$_{926}$—Z—R$_{626}$-alkenyl;
—R$_{426}$—NR$_{826}$—CR$_{326}$—NR$_{926}$—Z—R$_{626}$-aryl;
—R$_{426}$—NR$_{826}$—CR$_{326}$—NR$_{926}$—Z—R$_{626}$-heteroaryl; and
—R$_{426}$—NR$_{826}$—CR$_{326}$—NR$_{926}$—Z—R$_{626}$-heterocyclyl;
$R_{226}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N(R$_{526}$)$_2$;
—CO—N(R$_{526}$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;
each $R_{326}$ is =O or =S;
each $R_{426}$ is independently alkyl or alkenyl, which may be interrupted by one or more —O— groups;
each $R_{526}$ is independently H or $C_{1-10}$ alkyl;
$R_{626}$ is a bond, alkyl, or alkenyl, which may be interrupted by one or more —O— groups;
$R_{726}$ is H or $C_{1-10}$ alkyl which may be interrupted by a hetero atom, or $R_{726}$ can join with $R_{526}$ to form a ring;
$R_{826}$ is H, $C_{1-10}$ alkyl, or arylalkyl; or $R_{426}$ and $R_{826}$ can join together to form a ring;
$R_{926}$ is $C_{1-10}$ alkyl which can join together with $R_{826}$ to form a ring;
each Y is independently —O— or —S(O)$_{0-2}$—;
Z is a bond, —CO—, or —SO$_2$—;
v is 0 to 4; and
each $R_{26}$ present is independently selected from $C_{1-10}$ alkyl, $C_{1-10}$ alkoxy, hydroxy, halogen, and trifluoromethyl;
and pharmaceutically acceptable salts of any of the foregoing.

In another embodiment, the IRM compound can be chosen from 1H-imidazo[4,5-c]pyridin-4-amines defined by Formula XXVII below:

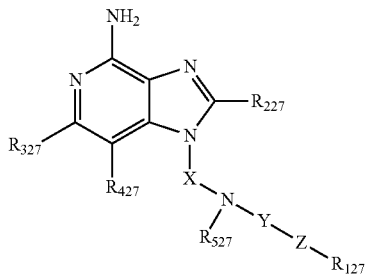

XXVII wherein X is alkylene or alkenylene;
Y is —CO— or —CS;
Z is a bond, —O—, or —S—;
$R_{127}$ is aryl, heteroaryl, heterocyclyl, alkyl or alkenyl, each of which may be unsubstituted or substituted by one or more substituents independently selected from:
-alkyl;
-alkenyl;
-aryl;
-heteroaryl;
-heterocyclyl;
-substituted cycloalkyl;
-substituted aryl;
-substituted heteroaryl;
-substituted heterocyclyl;
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—O-(alkyl)$_{0-1}$-heterocyclyl;
—O-(alkyl)$_{0-1}$-(substituted heterocyclyl);
—COOH;

—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—S(O)$_{0-2}$-(alkyl)$_{0-1}$-heterocyclyl;
—S(O)$_{0-2}$-(alkyl)$_{0-1}$-(substituted heterocyclyl);
-(alkyl)$_{0-1}$-N(R$_{627}$)$_2$;
-(alkyl)$_{0-1}$-NR$_{627}$—CO—O-alkyl;
-(alkyl)$_{0-1}$-NR$_{627}$—CO-alkyl;
-(alkyl)$_{0-1}$-NR$_{627}$—CO-aryl;
-(alkyl)$_{0-1}$-NR$_{627}$—CO-(substituted aryl);
-(alkyl)$_{0-1}$-NR$_{627}$—CO-heteroaryl;
-(alkyl)$_{0-1}$-NR$_{627}$—CO-(substituted heteroaryl);
—N$_3$;
-halogen;
-haloalkyl;
-haloalkoxy;
—CO-haloalkyl;
—CO-haloalkoxy;
—NO$_2$;
—CN;
—OH;
—SH; and in the case of alkyl, alkenyl, and heterocyclyl, oxo;

R$_{227}$ is selected from:
-hydrogen;
-alkyl;
-alkenyl;
-aryl;
-substituted aryl;
-heteroaryl;
-substituted heteroaryl;
-alkyl-O-alkyl;
-alkyl-S-alkyl;
-alkyl-O-aryl;
-alkyl-S-aryl:
-alkyl-O-alkenyl;
-alkyl-S-alkenyl; and
-alkyl or alkenyl substituted by one or more substituents selected from:
—OH;
-halogen;
—N(R$_{627}$)$_2$;
—CO—N(R$_{627}$)$_2$;
—CS—N(R$_{627}$)$_2$;
—SO$_2$—N(R$_{627}$)$_2$;
—NR$_{627}$—CO—C$_{1-10}$ alkyl;
—NR$_{627}$—CS—C$_{1-10}$ alkyl;
—NR$_{627}$—SO$_2$—C$_{1-10}$ alkyl;
—CO—C$_{1-10}$ alkyl;
—CO—O—C$_{1-10}$ alkyl;
—N$_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);

R$_{327}$ and R$_{427}$ are independently selected from hydrogen, alkyl, alkenyl, halogen, alkoxy, amino, alkylamino, dialkylamino, and alkylthio;

R$_{527}$ is H or C$_{1-10}$ alkyl, or R$_{527}$ can join with X to form a ring that contains one or two heteroatoms; or when R$_{127}$ is alkyl, R$_{527}$ and R$_{127}$ can join to form a ring;

each R$_{627}$ is independently H or C$_{1-10}$ alkyl;

and pharmaceutically acceptable salts thereof.

In another embodiment, the IRM compound can be chosen from 1H-imidazo[4,5-c]pyridin-4-amines defined by Formula XXVIII below:

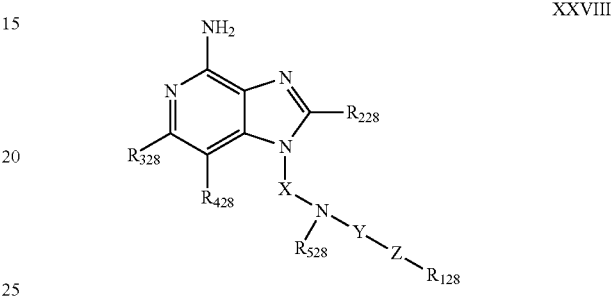

XXVIII wherein X is alkylene or alkenylene;
Y is —SO$_2$—;
Z is a bond or —NR$_{628}$—;
R$_{128}$ is aryl, heteroaryl, heterocyclyl, alkyl or alkenyl, each of which may be unsubstituted or substituted by one or more substituents independently selected from:
-alkyl;
-alkenyl;
-aryl;
-heteroaryl;
-heterocyclyl;
-substituted cycloalkyl;
-substituted aryl;
-substituted heteroaryl;
-substituted heterocyclyl;
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—O-(alkyl)$_{0-1}$-heterocyclyl;
—O-(alkyl)$_{0-1}$-(substituted heterocyclyl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—S(O)$_{0-2}$-(alkyl)$_{0-1}$-heterocyclyl;
—S(O)$_{0-2}$-(alkyl)$_{0-1}$-(substituted heterocyclyl);
-(alkyl)$_{0-1}$-N(R$_{628}$)$_2$;
-(alkyl)$_{0-1}$-NR$_{628}$—CO—O-alkyl;
-(alkyl)$_{0-1}$-NR$_{628}$—CO-alkyl;
-(alkyl)$_{0-1}$-NR$_{628}$—CO-aryl;
-(alkyl)$_{0-1}$-NR$_{628}$—CO-(substituted aryl);
-(alkyl)$_{0-1}$-NR$_{628}$—CO-heteroaryl;
-(alkyl)$_{0-1}$-NR$_{628}$—CO-(substituted heteroaryl);
—N$_3$;
-halogen;

-haloalkyl;
-haloalkoxy;
—CO-haloalkyl;
—CO-haloalkoxy;
—NO$_2$;
—CN;
—OH;
—SH; and in the case of alkyl, alkenyl, and heterocyclyl, oxo;

R$_{228}$ is selected from:
  -hydrogen;
  -alkyl;
  -alkenyl;
  -aryl;
  -substituted aryl;
  -heteroaryl;
  -substituted heteroaryl;
  -alkyl-O-alkyl;
  -alkyl-S-alkyl;
  -alkyl-O-aryl;
  -alkyl-S-aryl:
  -alkyl-O-alkenyl;
  -alkyl-S-alkenyl; and
  -alkyl or alkenyl substituted by one or more substituents selected from:
    —OH;
    -halogen;
    —N(R$_{628}$)$_2$;
    —CO—N(R$_{628}$)$_2$;
    —CS—N(R$_{628}$)$_2$;
    —SO$_2$—N(R$_{628}$)$_2$;
    —NR$_{628}$—CO—C$_{1-10}$ alkyl;
    —NR$_{628}$—CS—C$_{1-10}$ alkyl;
    —NR$_{628}$—SO$_2$—C$_{1-10}$ alkyl;
    —CO—C$_{1-10}$ alkyl;
    —CO—O—C$_{1-10}$ alkyl;
    —N$_3$;
    -aryl;
    -substituted aryl;
    -heteroaryl;
    -substituted heteroaryl;
    -heterocyclyl;
    -substituted heterocyclyl;
    —CO-aryl;
    —CO-(substituted aryl);
    —CO-heteroaryl; and
    —CO-(substituted heteroaryl);

R$_{328}$ and R$_{428}$ are independently selected from hydrogen, alkyl, alkenyl, halogen, alkoxy, amino, alkylamino, dialkylamino, and alkylthio;

R$_{528}$ is H or C$_{1-10}$ alkyl, or R$_{528}$ can join with X to form a ring; or when R$_{128}$ is alkyl, R$_{528}$ and R$_{128}$ can join to form a ring;

each R$_{628}$ is independently H or C$_{1-10}$ alkyl;
and pharmaceutically acceptable salts thereof.

In another embodiment, the IRM compound can be chosen from 1H-imidazo[4,5-c]pyridin-4-amines defined by Formula XXIX below:

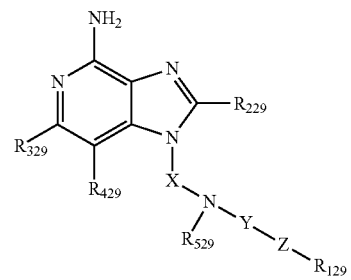

XXIX wherein X is alkylene or alkenylene;
Y is —CO— or —CS;
Z is —NR$_{629}$—, —NR$_{629}$—CO—, —NR$_{629}$—SO$_2$—, or —NR$_{729}$—;
R$_{129}$ is aryl, heteroaryl, heterocyclyl, alkyl or alkenyl, each of which may be unsubstituted or substituted by one or more substituents independently selected from:
  -alkyl;
  -alkenyl;
  -aryl;
  -heteroaryl;
  -heterocyclyl;
  -substituted cycloalkyl;
  -substituted aryl;
  -substituted heteroaryl;
  -substituted heterocyclyl;
  —O-alkyl;
  —O-(alkyl)$_{0-1}$-aryl;
  —O-(alkyl)$_{0-1}$-(substituted aryl);
  —O-(alkyl)$_{0-1}$-heteroaryl;
  —O-(alkyl)$_{0-1}$-(substituted heteroaryl);
  —O-(alkyl)$_{0-1}$-heterocyclyl;
  —O-(alkyl)$_{0-1}$-(substituted heterocyclyl);
  —COOH;
  —CO—O-alkyl;
  —CO-alkyl;
  —S(O)$_{0-2}$-alkyl;
  —S(O)$_{0-2}$-(alkyl)$_{0-1}$-aryl;
  —S(O)$_{0-2}$-(alkyl)$_{0-1}$-(substituted aryl);
  —S(O)$_{0-2}$-(alkyl)$_{0-1}$-heteroaryl;
  —S(O)$_{0-2}$-(alkyl)$_{0-1}$-(substituted heteroaryl);
  —S(O)$_{0-2}$-(alkyl)$_{0-1}$-heterocyclyl;
  —S(O)$_{0-2}$-(alkyl)$_{0-1}$-(substituted heterocyclyl);
  -(alkyl)$_{0-1}$-N(R$_{629}$)$_2$;
  -(alkyl)$_{0-1}$-NR$_{629}$—CO—O-alkyl;
  -(alkyl)$_{0-1}$-NR$_{629}$—CO-alkyl;
  -(alkyl)$_{0-1}$-NR$_{629}$—CO-aryl;
  -(alkyl)$_{0-1}$-NR$_{629}$—CO-(substituted aryl);
  -(alkyl)$_{0-1}$-NR$_{629}$—CO-heteroaryl;
  (alkyl)$_{0-1}$-NR$_{629}$—CO-(substituted heteroaryl);
  —P(O)(O-alkyl)$_2$;
  —N$_3$;
  -halogen;
  -haloalkyl;
  -haloalkoxy;
  —CO-haloalkyl;
  —CO-haloalkoxy;
  —NO$_2$;
  —CN;
  —OH;
  —SH; and in the case of alkyl, alkenyl, and heterocyclyl, oxo;

$R_{229}$ is selected from:
- hydrogen;
- alkyl;
- alkenyl;
- aryl;
- substituted aryl;
- heteroaryl;
- substituted heteroaryl;
- alkyl-O-alkyl;
- alkyl-S-alkyl;
- alkyl-O-aryl;
- alkyl-S-aryl:
- alkyl-O-alkenyl;
- alkyl-S-alkenyl; and
- alkyl or alkenyl substituted by one or more substituents selected from:
  —OH;
  -halogen;
  —N($R_{629}$)$_2$;
  —CO—N($R_{629}$)$_2$;
  —CS—N($R_{629}$)$_2$;
  —SO$_2$—N($R_{629}$)$_2$;
  —NR$_{629}$—CO—C$_{1-10}$ alkyl;
  —NR$_{629}$—CS—C$_{1-10}$ alkyl;
  —NR$_{629}$—SO$_2$—C$_{1-10}$ alkyl;
  —CO—C$_{1-10}$ alkyl;
  —CO—O—C$_{1-10}$ alkyl;
  —N$_3$;
  -aryl;
  -substituted aryl;
  -heteroaryl;
  -substituted heteroaryl;
  -heterocyclyl;
  -substituted heterocyclyl;
  —CO-aryl;
  —CO-(substituted aryl);
  —CO-heteroaryl; and
  —CO-(substituted heteroaryl);

$R_{329}$ and $R_{429}$ are independently selected from hydrogen, alkyl, alkenyl, halogen, alkoxy, amino, alkylamino, dialkylamino, and alkylthio;

$R_{529}$ is H or C$_{1-10}$ alkyl, or $R_{529}$ can join with X to form a ring that contains one or two heteroatoms;

each $R_{629}$ is independently H or C$_{1-10}$ alkyl;

$R_{729}$ is H or C$_{1-10}$ alkyl which may be interrupted by a heteroatom; or when $R_{129}$ is alkyl, $R_{729}$ and $R_{129}$ can join to form a ring;

and pharmaceutically acceptable salts thereof.

In another embodiment, the IRM compound can be chosen from 1-position ether or thioether substituted 1H-imidazo[4,5-c]pyridin-4-amines defined by Formula XXX below:

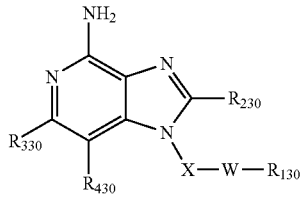

XXX wherein:
X is —CH($R_{530}$)—, —CH($R_{530}$)-alkylene-, —CH($R_{530}$)-alkenylene-, or CH($R_{530}$)-alkylene-Y-alkylene-;

Y is —O—, or —S(O)$_{02}$—;
—W—$R_{130}$ is selected from —O—$R_{130-1-5}$ and —S(O)$_{0-2}$—$R_{130-6}$;
$R_{130-1-5}$ is selected from
—$R_{630}$—C($R_{730}$)—Z—$R_{830}$-alkyl;
—$R_{630}$—C($R_{730}$)—Z—$R_{830}$-alkenyl;
—$R_{630}$—C($R_{730}$)—Z—$R_{830}$-aryl;
—$R_{630}$—C($R_{730}$)—Z—$R_{380}$-heteroaryl;
—$R_{630}$—C($R_{730}$)—Z—$R_{830}$-heterocyclyl;
—$R_{630}$—C($R_{730}$)—Z—H;
—$R_{630}$—N($R_{930}$)—C($R_{730}$)—$R_{830}$-alkyl;
—$R_{630}$—N($R_{930}$)—C($R_{730}$)—$R_{830}$-alkenyl;
—$R_{630}$—N($R_{930}$)—C($R_{730}$)—$R_{830}$-aryl;
—$R_{630}$—N($R_{930}$)—C($R_{730}$)—$R_{830}$-heteroaryl;
—$R_{630}$—N($R_{930}$)—C($R_{730}$)—$R_{830}$-heterocyclyl;
—$R_{630}$—N($R_{930}$)—C($R_{730}$)—$R_{1030}$;
—$R_{630}$—N($R_{930}$)—SO$_2$—$R_{830}$-alkyl;
—$R_{630}$—N($R_{930}$)—SO$_2$—$R_{830}$-alkenyl;
—$R_{630}$—N($R_{930}$)—SO$_2$—$R_{830}$-aryl;
—$R_{630}$—N($R_{930}$)—SO$_2$—$R_{830}$-heteroaryl;
—$R_{630}$—N($R_{930}$)—SO$_2$—$R_{830}$-heterocyclyl;
—$R_{630}$—N($R_{930}$)—SO$_2$—$R_{1030}$;
—$R_{630}$—N($R_{930}$)—SO$_2$—N($R_{530}$)—$R_{830}$-alkyl;
—$R_{630}$—N($R_{930}$)—SO$_2$—N($R_{530}$)—$R_{830}$-alkenyl;
—$R_{630}$—N($R_{930}$)—SO$_2$—N($R_{530}$)—$R_{830}$-aryl;
—$R_{630}$—N($R_{930}$)—SO$_2$—N($R_{530}$)—$R_{830}$-heteroaryl;
—$R_{630}$—N($R_{930}$)—SO$_2$—N($R_{530}$)—$R_{830}$-heterocyclyl;
—$R_{630}$—N($R_{930}$)—SO$_2$—$R_{1030}$;
—$R_{630}$—N($R_{930}$)—C($R_{730}$)—N($R_{530}$)-Q-$R_{830}$-alkyl;
—$R_{630}$—N($R_{930}$)—C($R_{730}$)—N($R_{530}$)-Q-$R_{830}$-alkenyl;
—$R_{630}$—N($R_{930}$)—C($R_{730}$)—N($R_{530}$)-Q-$R_{830}$-aryl;
—$R_{630}$—N($R_{930}$)—C($R_{730}$)—N($R_{530}$)-Q-$R_{830}$-heteroaryl;
—$R_{630}$—N($R_{930}$)—C($R_{730}$)—N($R_{530}$)-Q-$R_{830}$-heterocyclyl;
—$R_{630}$—N($R_{930}$)—C($R_{730}$)—N($R_{530}$)$_2$;

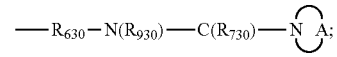

—$R_{630}$—N($R_{930}$)—C($R_{730}$)—N($R_{1130}$)-Q-$R_{830}$-alkyl;
—$R_{630}$—N($R_{930}$)—C($R_{730}$)—N($R_{1130}$)-Q-$R_{830}$-alkenyl;
—$R_{630}$—N($R_{930}$)—C($R_{730}$)—N($R_{1130}$)-Q-$R_{830}$-aryl;
—$R_{630}$—N($R_{930}$)—C($R_{730}$)—N($R_{1130}$)-Q-$R_{830}$-heteroaryl;
—$R_{630}$—N($R_{930}$)—C($R_{730}$)—N($R_{1130}$)-Q-$R_{830}$-heterocyclyl;
—$R_{630}$—N($R_{930}$)—C($R_{730}$)—N($R_{1130}$)H;
-alkenyl;
-aryl;
—$R_{630}$-aryl;
-heteroaryl;
-heterocyclyl;
—$R_{630}$-heteroaryl; and
—$R_{630}$-heterocyclyl;

Z is —N($R_{530}$)—, —O—, or —S—;
Q is a bond, —CO—, or —SO$_2$—;
A represents the atoms necessary to provide a 5- or 6-membered heterocyclic or heteroaromatic ring that contains up to three heteroatoms;
$R_{130-6}$ is selected from:
-;
-aryl;
-heteroaryl;
-heterocyclyl;

-alkenyl;
—$R_{630}$-aryl;
—$R_{630}$-heteroaryl; and
—$R_{630}$-heterocyclyl;

each $R_{530}$ is independently hydrogen, $C_{1-10}$ alkyl, or $C_{2-10}$ alkenyl;

$R_{630}$ is alkylene, alkenylene, or alkynylene, which may be interrupted by one or more —O— groups;

$R_{730}$ is =O or =S;

$R_{830}$ is a bond, alkylene, alkenylene, or alkynylene, which may be interrupted by one or more —O— groups;

$R_{930}$ is hydrogen, $C_{1-10}$ alkyl, or arylalkyl; or $R_{930}$ can join together with any carbon atom of $R_{630}$ to form a ring of the formula

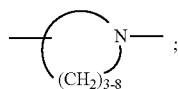

$R_{1030}$ is hydrogen or $C_{1-10}$ alkyl; or $R_{930}$ and $R_{1030}$ can join together to form a ring selected from

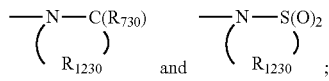

$R_{1130}$ is $C_{1-10}$ alkyl; or $R_{930}$ and $R_{1130}$ can join together to form a ring having the structure

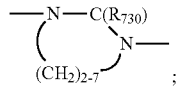

$R_{1230}$ is $C_{2-7}$ alkylene which is straight chain or branched, wherein the branching does not prevent formation of the ring; and $R_{230}$, $R_{330}$ and $R_{430}$ are independently selected from hydrogen and non-interfering substituents;
and pharmaceutically acceptable salts thereof.

Illustrative non-interfering $R_{230}$ substituents include:
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
  —OH;
  -halogen;
  —N($R_{530}$)$_2$;
  —C(O)—$C_{1-10}$ alkyl;
  —C(O)—O—$C_{1-10}$ alkyl;
  —$N_3$;
  -aryl;
  -heteroaryl;
  -heterocyclyl;
  —C(O)-aryl; and
  —C(O)-heteroaryl.

Illustrative non-interfering $R_{330}$ and $R_{430}$ substituents include: $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro.

In another embodiment, the IRM compound can be chosen from 1H-imidazo dimers of the formula (XXXI):

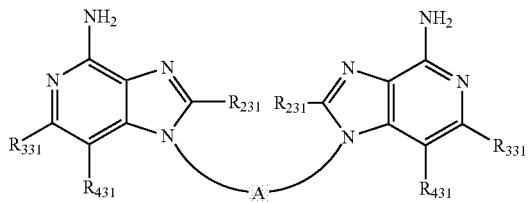

XXXI wherein:
A is a divalent linking group selected from the group consisting of:
  straight or branched chain $C_{4-20}$ alkylene;
  straight or branched chain $C_{4-20}$ alkenylene;
  straight or branched chain $C_{4-20}$ alkynylene; and
  Z—Y—W—Y—Z—;
each Z is independently selected from the group consisting of:
  straight or branched chain $C_{2-20}$ alkylene;
  straight or branched chain $C_{4-20}$ alkenylene; and
  straight or branched chain $C_{4-20}$ alkynylene;
  any of which may be optionally interrupted by —O—, —N($R_{531}$)—, or —S(O)$_2$—;
each Y is independently selected from the group consisting of:
  a bond;
  —N($R_{531}$)C(O)—;
  —C(O)N($R_{531}$)—;
  —N($R_{531}$)C(O)N($R_{531}$)—;
  —N($R_{531}$)S(O)$_2$—;
  —S(O)$_2$N($R_{531}$)—;
  —OC(O)O—;
  —OC(O)—;
  —C(O)O—;
  —N($R_{531}$)C(O)O—; and
  —OC(O)N($R_{531}$)—;
W is selected from the group consisting of:
  straight or branched chain $C_{2-20}$ alkylene;
  straight or branched chain $C_{2-20}$ alkenylene;
  straight or branched chain $C_{4-20}$ alkynylene;
  straight or branched chain perfluoro $C_{2-20}$ alkylene;
  $C_{1-4}$ alkylene-O—$C_{1-4}$ alkylene;
  —C(O)—;
  —S(O)$_2$—;
  —OC(O)O—;
  —N($R_{531}$)C(O)N($R_{531}$)—;

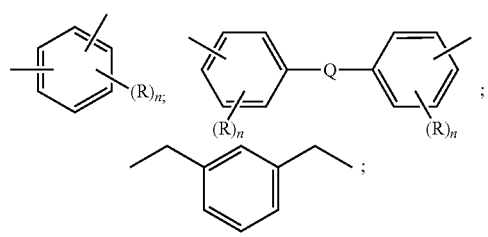

1,5-naphthylene;
2,6-pyridinylene;
1,2-cyclohexylene;
1,3-cyclohexylene;
1,4-cyclohexylene;
trans-1,4-cyclohexylene;

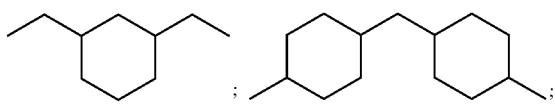

and
trans-5-norbornen-2,3-diyl;
wherein n is 0-4; each R is independently selected from the group consisting of $C_{1-4}$ alkyl, $C_{1-4}$ alkoxy, and halogen; and Q is selected from the group consisting of a bond, —$CH_2$—, and —O—;
$R_{231}$ is selected from the group consisting of:
-hydrogen;
-alkyl;
-alkenyl;
-aryl;
-substituted aryl;
-heteroaryl;
-substituted heteroaryl;
-alkyl-X-alkyl;
-alkyl-X-aryl;
-alkyl-X-alkenyl; and
-alkyl or alkenyl substituted by one or more substituents selected from the group consisting of:
  —OH;
  -halogen;
  —$N(R_{631})_2$;
  —C(O)—$N(R_{631})_2$;
  —C(S)—$N(R_{631})_2$;
  —$S(O)_2$—$N(R_{631})_2$;
  —$N(R_{631})$—C(O)—$C_{1-10}$ alkyl;
  —$N(R_{631})$—C(S)—$C_{1-10}$ alkyl;
  —$N(R_{631})$—$S(O)_2$—$C_{1-10}$ alkyl;
  —C(O)—$C_{1-10}$ alkyl;
  —C(O)—O—$C_{1-10}$ alkyl;
  —$N_3$;
  -aryl;
  -substituted aryl;
  -heteroaryl;
  -substituted heteroaryl;
  -heterocyclyl;
  -substituted heterocyclyl;
  —C(O)-aryl;
  —C(O)-(substituted aryl);
  —C(O)-heteroaryl; and
  —C(O)-(substituted heteroaryl);
$R_{331}$ and $R_{431}$ are each independently selected from the group consisting of:
-hydrogen;
-halogen;
-alkyl;
-alkenyl;
—X-alkyl; and
—$N(R_{631})_2$;
or when taken together, $R_{331}$ and $R_{431}$ form a fused aryl or heteroaryl ring that is unsubstituted or substituted by one or more substituents selected from the group consisting of:
-halogen;
-alkyl;
-alkenyl;
—X-alkyl; and
—$N(R_{631})_2$;
or when taken together, $R_{331}$ and $R_{431}$ form a fused 5 to 7 membered saturated ring, containing 0 to 2 heteroatoms and unsubstituted or substituted by one or more substituents selected from the group consisting of:
-halogen;
-alkyl;
-alkenyl;
—X-alkyl; and
—$N(R_{631})_2$;
each $R_{531}$ is independently selected from the group consisting of:
hydrogen;
$C_{1-6}$ alkyl;
$C_{3-7}$ cycloalkyl; and
benzyl; or
when Y is —$N(R_{531})C(O)$—, —$C(O)N(R_{531})$—, —$N(R_{531})C(O)N(R_{531})$—, —$N(R_{531})S(O)_2$—, —$S(O)_2N(R_{531})$—, —$N(R_{531})C(O)O$—, or —$OC(O)N(R_{531})$— and the nitrogen of the $N(R_{531})$ group is bonded to Z, then $R_{531}$ can join with Z to form a ring having the structure

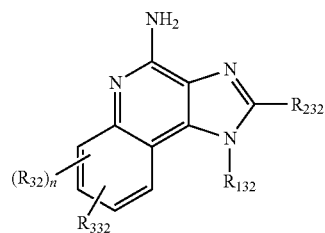

each $R_{631}$ is independently hydrogen or $C_{1-10}$ alkyl;
$R_{731}$ is $C_{3-8}$ alkylene; and
X is —O— or —S—;
with the proviso that if W is —C(O)—, —$S(O)_2$—, —OC(O)O—, or —$N(R_{531})C(O)N(R_{531})$— then each Y is a bond; and pharmaceutically acceptable salts thereof.

In another embodiment, the IRM compound can be chosen from 6-, 7-, 8-, or 9-position aryl or heteroaryl substituted 1H-imidazo[4,5-c]quinolin-4-amines of the following Formula (XXXII):

XXXII wherein:
$R_{32}$ is selected from the group consisting of alkyl, alkoxy, hydroxy, and trifluoromethyl;
n is 0 or 1;
$R_{132}$ and $R_{232}$ are independently selected from the group consisting of hydrogen and non-interfering substituents;
$R_{332}$ is selected from the group consisting of:
  —Z—Ar,
  —Z—Ar'—Y—$R_{432}$,
  —Z—Ar'—X—Y—$R_{432}$,
  —Z—Ar'—$R_{532}$, and
  —Z—Ar'—X—$R_{532}$;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N(R$_{832}$)—,
—C(R$_{632}$)—,
—C(R$_{632}$)—O—,
—O—C(R$_{632}$)—,
—O—C(O)—O—,
—N(R$_{832}$)-Q-,
—C(R$_{632}$)—N(R$_{832}$)—,
—O—C(R$_{632}$)—N(R$_{832}$)—,
—C(R$_{632}$)—N(OR$_{932}$)—,

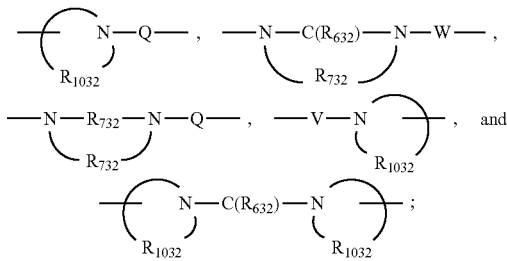

Z is selected from the group consisting of a bond, alkylene, alkenylene, and alkynylene;

R$_{432}$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_{532}$ is selected from the group consisting of:

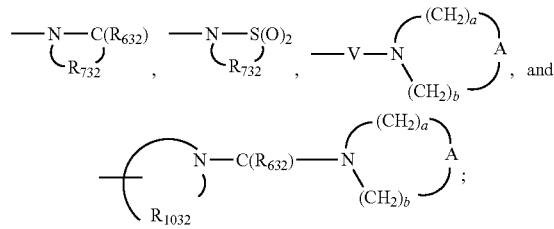

each R$_{632}$ is independently selected from the group consisting of =O and =S;
each R$_{732}$ is independently C$_{2-7}$ alkylene;
each R$_{832}$ is independently selected from the group consisting of hydrogen, alkyl, alkoxyalkylenyl, and arylalkylenyl;
R$_{932}$ is selected from the group consisting of hydrogen and alkyl;
each R$_{1032}$ is independently C$_{3-8}$ alkylene;
A is selected from the group consisting of —O—, —C(O)—, —S(O)$_{0-2}$—, —CH$_2$—, and —N(R$_{432}$)—;
Q is selected from the group consisting of a bond, —C(R$_{632}$)—, —C(R$_{632}$)—C(R$_{632}$), —S(O)$_2$—, —C(R$_{632}$)—N(R$_{832}$)—W—, —S(O)$_2$—N(R$_{832}$)—, —C(R$_{632}$)—O—, and —C(R$_{632}$)—N(OR$_{932}$)—;
V is selected from the group consisting of —C(R$_{632}$)—, —O—C(R$_{632}$)—, —N(R$_{832}$)—C(R$_{632}$)—, and —S(O)$_2$—;
W is selected from the group consisting of a bond, —C(O)—, and —S(O)$_2$—; and
a and b are independently integers from 1 to 6 with the proviso that a+b is ≤7; and pharmaceutically acceptable salts thereof.

Illustrative non-interfering R$_{132}$ substituents include:
—R$_{432}$,
—X—R$_{432}$,
—X—Y—R$_{432}$,
—X—Y—X—Y—R$_{432}$, and
—X—R$_{532}$;

wherein:
each X is independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:
—S(O)$_{0-2}$—,
—S(O)$_2$—N(R$_{832}$)—,
—C(R$_{632}$)—,
—C(R$_{632}$)—O—,
—O—C(R$_{632}$)—,
—O—C(O)—O—,
—N(R$_{832}$)-Q-,
—C(R$_{632}$)—N(R$_{832}$)—,
—O—C(R$_{632}$)—N(R$_{832}$)—,
—C(R$_{632}$)—N(OR$_{932}$)—,

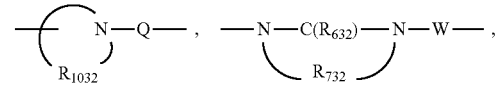

-continued

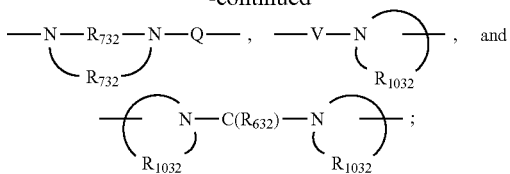, 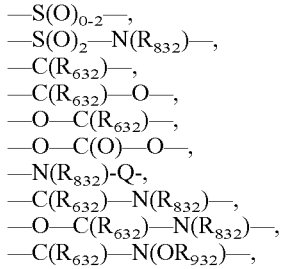, and

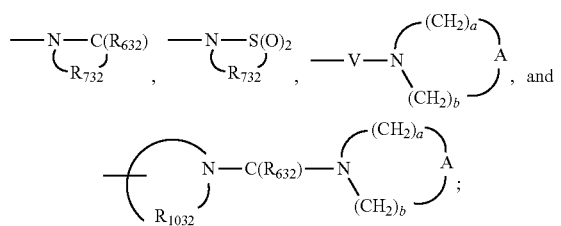;

$R_{432}$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_{532}$ is selected from the group consisting of:

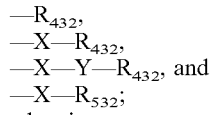;

each $R_{632}$ is independently selected from the group consisting of =O and =S;
each $R_{732}$ is independently $C_{2-7}$ alkylene;
each $R_{832}$ is independently selected from the group consisting of hydrogen, alkyl, alkoxyalkylenyl, and arylalkylenyl;
each $R_{932}$ is independently selected from the group consisting of hydrogen and alkyl;
each $R_{1032}$ is independently $C_{3-8}$ alkylene;
A is selected from the group consisting of —O—, —C(O)—, —S(O)$_{0-2}$—, —CH$_2$—, and —N(R$_{432}$)—;
each Q is independently selected from the group consisting of a bond, —C(R$_{632}$)—, —C(R$_{632}$)—C(R$_{632}$)—, —S(O)$_2$—, —C(R$_{632}$)—N(R$_{832}$)—W—, —S(O)$_2$—N(R$_{832}$)—, —C(R$_{632}$)—O—, and —C(R$_{632}$)—N(OR$_{932}$)—;
each V is independently selected from the group consisting of —C(R$_{632}$)—, —O—C(R$_{632}$)—, —N(R$_{832}$)—C(R$_{632}$)—, and —S(O)$_2$—;
each W is independently selected from the group consisting of a bond, —C(O)—, and —S(O)$_2$—; and
a and b are independently integers from 1 to 6 with the proviso that a+b is ≤7;

Illustrative non-interfering $R_{232}$ substituents include:
—$R_{432}$,
—X—$R_{432}$,
—X—Y—$R_{432}$, and
—X—$R_{532}$;
wherein:
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—S(O)$_{0-2}$—,
—S(O)$_2$—N(R$_{832}$)—,
—C(R$_{632}$)—,
—C(R$_{632}$)—O—,
—O—C(R$_{632}$)—,
—O—C(O)—O—,
—N(R$_{832}$)-Q-,
—C(R$_{632}$)—N(R$_{832}$)—,
—O—C(R$_{632}$)—N(R$_{832}$)—,
—C(R$_{632}$)—N(OR$_{932}$)—,

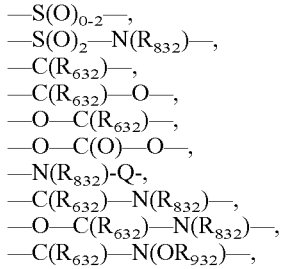, 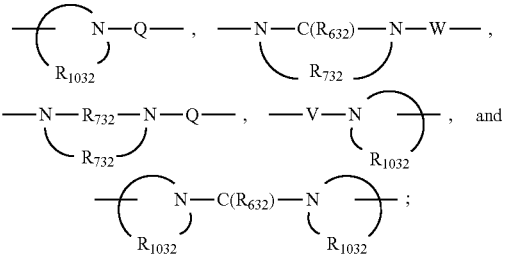,

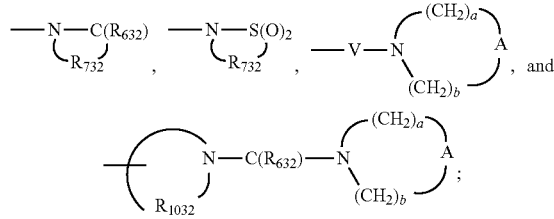;

$R_{432}$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_{532}$ is selected from the group consisting of:

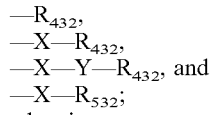;

each $R_{632}$ is independently selected from the group consisting of =O and =S;
each $R_{732}$ is independently $C_{2-7}$ alkylene;
each $R_{832}$ is independently selected from the group consisting of hydrogen, alkyl, alkoxyalkylenyl, and arylalkylenyl;
$R_{932}$ is selected from the group consisting of hydrogen and alkyl;
each $R_{1032}$ is independently $C_{3-8}$ alkylene;
A is selected from the group consisting of —O—, —C(O)—, —S(O)$_{0-2}$—, —CH$_2$—, and —N(R$_{432}$)—;

Q is selected from the group consisting of a bond, —C($R_{632}$)—, —C($R_{632}$)—C($R_{632}$)—, —S(O)$_2$—, —C($R_{632}$)—N($R_{832}$)—W—, —S(O)$_2$—N($R_{832}$)—, —C($R_{632}$)—O—, and —C($R_{632}$)—N(O$R_{932}$)—;

V is selected from the group consisting of —C($R_{632}$)—, —O—C($R_{632}$)—, —N($R_{832}$)—C($R_{632}$)—, and —S(O)$_2$—;

W is selected from the group consisting of a bond, —C(O)—, and —S(O)$_2$—; and a and b are independently integers from 1 to 6 with the proviso that a+b is ≤7;

In some embodiments the IRM can be chosen from amide substituted 1H-imidazo[4,5-c]quinolin-4-amines, tetrahydro-1H-imidazo[4,5-c]quinolin-4-aminess, 1H-imidazo[4,5-c]pyridin-4-amines, 1H-imidazo[4,5-c]naphthyridin-4-amines, or tetrahydro-1H-imidazo[4,5-c]naphthyridin-4-aminess of the following Formula XXXIII.

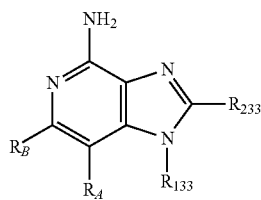

XXXIII wherein:

$R_{133}$ is selected from the group consisting of:
—X'—C(O)—N($R_{133}$')($R_{133}$") and

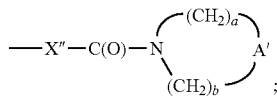

X' is selected from the group consisting of —CH($R_{933}$)—, —CH($R_{933}$)-alkylene-, and —CH($R_{933}$)-alkenylene-;

X" is selected from the group consisting of —CH($R_{933}$)—, —CH($R_{933}$)-alkylene-, and —CH($R_{933}$)-alkenylene-; wherein the alkylene and alkenylene are optionally interrupted with one or more —O— groups;

$R_{133}$' and $R_{133}$" are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;

A' is selected from the group consisting of —O—, —C(O)—, —CH$_2$—, —S(O)$_{0-2}$—, and —N(Q-$R_{433}$)—;

a and b are independently integers from 1 to 6 with the proviso that a+b is ≤7;

$R_A$ and $R_B$ are independently selected from the group consisting of:
hydrogen,
halogen,
alkyl,
alkenyl,
alkoxy,
alkylthio, and
N($R_{933}$)$_2$;

or $R_A$ and $R_B$ taken together form either a fused aryl ring that is unsubstituted or substituted by one or more $R_a$ groups, or a fused 5 to 7 membered saturated ring that is unsubstituted or substituted by one or more $R_c$ groups;

or $R_A$ and $R_B$ taken together form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups;

each $R_a$ is independently selected from the group consisting of halogen, alkyl, haloalkyl, alkoxy, and —N($R_{933}$)$_2$;

each $R_b$ is independently selected from the group consisting of halogen, hydroxy, alkyl, haloalkyl, alkoxy, and —N($R_{933}$)$_2$;

each $R_c$ is independently selected from the group consisting of halogen, hydroxy, alkyl, alkenyl, haloalkyl, alkoxy, alkylthio, and —N($R_{933}$)$_2$;

$R_{233}$ is selected from the group consisting of:
—$R_{433}$,
—X—$R_{433}$,
—X—Y—$R_{433}$, and
—X—$R_{533}$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:
—S(O)$_{0-2}$—,
—S(O)$_2$—N($R_{833}$)—,
—C($R_{633}$)—,
—C($R_{633}$)—O—,
—O—C($R_{633}$)—,
—O—C(O)—O—,
—N($R_{833}$)-Q-,
—C($R_{633}$)—N($R_{833}$)—,
—O—C($R_{633}$)—N($R_{833}$)—,
—C($R_{633}$)—N(O$R_{933}$)—,

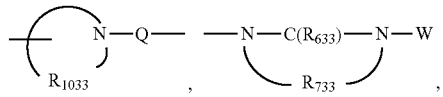

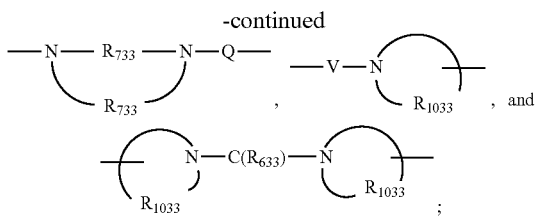

each $R_{433}$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_{533}$ is selected from the group consisting of:

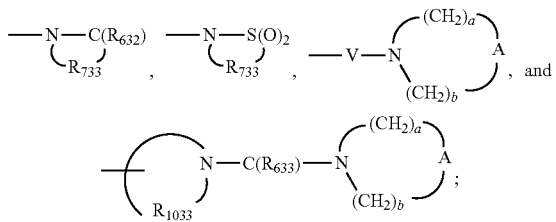

each $R_{633}$ is independently selected from the group consisting of =O and =S;

each $R_{733}$ is independently $C_{2-7}$ alkylene;

each $R_{833}$ is independently selected from the group consisting of hydrogen, alkyl, alkoxyalkylenyl, and arylalkylenyl;

each $R_{933}$ is independently selected from the group consisting of hydrogen and alkyl;

each $R_{1033}$ is independently $C_{3-8}$ alkylene;

A is selected from the group consisting of —O—, —C(O)—, —S(O)$_{0-2}$—, —CH$_2$—, and —N(R$_{433}$)—;

each Q is independently selected from the group consisting of a bond, —C(R$_{633}$)—, —C(R$_{633}$)—C(R$_{633}$)—, —S(O)$_2$—, —C(R$_{633}$)—N(R$_{833}$)—W—, —S(O)$_2$—N(R$_{833}$)—, —C(R$_{633}$)—O—, and —C(R$_{633}$)—N(OR$_{933}$)—;

V is selected from the group consisting of —C(R$_{633}$)—, —O—C(R$_{633}$)—, —N(R$_{833}$)—C(R$_{633}$)—, and —S(O)$_2$—; and each W is independently selected from the group consisting of a bond, —C(O)—, and —S(O)$_2$—;

with the proviso that when $R_A$ and $R_B$ form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups, then $R_{133}$ can also be —X″—C(O)—N(R$_{133}$′)(R$_{133}$″);

or a pharmaceutically acceptable salt thereof.

In another embodiment, the IRM compound can be chosen from aryloxy or arylalkyleneoxy substituted 1H-imidaz[4,5-c]quinoline-4-amines of the following Formula XXXIV:

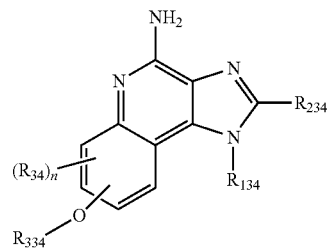

wherein:

$R_{334}$ is selected from the group consisting of:
—Z—Ar,
—Z—Ar′—Y—R$_{434}$,
—Z—Ar′—X—Y—R$_{434}$,
—Z—Ar′—R$_{534}$, and
—Z—Ar′—X—R$_{534}$;

Z is selected from the group consisting of a bond, alkylene, alkenylene, and alkynylene wherein alkylene, alkenylene, and alkynylene are optionally interrupted with —O—;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

Ar′ is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

$R_{34}$ is selected from the group consisting of alkyl, alkoxy, hydroxy, halogen, and trifluoromethyl;

n is 0 or 1;

$R_{134}$ is selected from the group consisting of:
—R$_{434}$,
—X—R$_{434}$,
—X—Y—R$_{434}$,
—X—Y—X—Y—R$_{434}$, and
—X—R$_{534}$;

$R_{234}$ is selected from the group consisting of:
—R$_{434}$,
—X—R$_{434}$,
—X—Y—R$_{434}$, and
—X—R$_{534}$;

each X is independently selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups;

each Y is independently selected from the group consisting of:
- —S(O)$_{0-2}$—,
- —S(O)$_2$—N(R$_{834}$)—,
- —C(R$_{634}$)—,
- —C(R$_{634}$)—O—,
- —O—C(R$_{634}$)—,
- —O—C(O)—O—,
- —N(R$_{834}$)-Q-,
- —C(R$_{634}$)—N(R$_{834}$)—,
- —O—C(R$_{634}$)—N(R$_{834}$)—,
- —C(R$_{634}$)—N(OR$_{934}$)—,

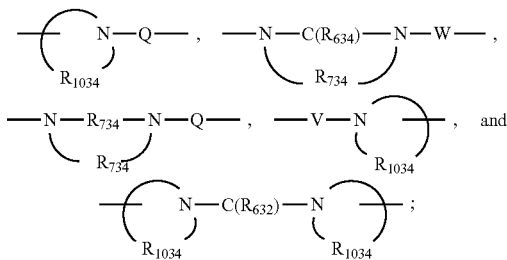

each R$_{434}$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R$_{534}$ is independently selected from the group consisting of:

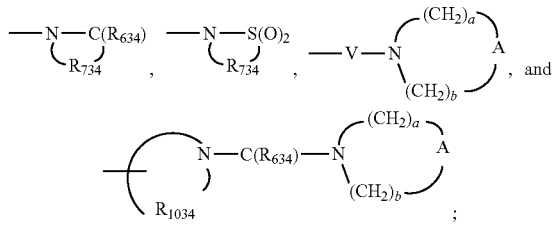

each R$_{634}$ is independently selected from the group consisting of =O and =S;

each R$_{734}$ is independently C$_{2-7}$ alkylene;

each R$_{834}$ is independently selected from the group consisting of hydrogen, alkyl, alkoxyalkylenyl, and arylalkylenyl;

each R$_{934}$ is independently selected from the group consisting of hydrogen and alkyl;

each R$_{1034}$ is independently C$_{3-8}$alkylene;

each A is independently selected from the group consisting of —O—, —C(O)—, —S(O)$_{0-2}$—, —CH$_2$—, and —N(R$_{434}$)—;

each Q is independently selected from the group consisting of a bond, —C(R$_{634}$)—, —C(R$_{634}$)—C(R$_{634}$)—, —S(O)$_2$—, —C(R$_{634}$)—N(R$_{834}$)—W—, —S(O)$_2$—N(R$_{834}$)—, —C(R$_{634}$)—O—, and —C(R$_{634}$)—N(OR$_{934}$)—;

each V is independently selected from the group consisting of —C(R$_{634}$)—, —O—C(R$_{634}$)—, —N(R$_{834}$)—C(R$_{634}$)—, and —S(O)$_2$—;

each W is independently selected from the group consisting of a bond, —C(O)—, and —S(O)$_2$—; and a and b are independently integers from 1 to 6 with the proviso that a+b is ≤7;

or a pharmaceutically acceptable salt thereof.

Herein, "non-interfering" means that the ability of the compound or salt to modulate (e.g., induce or inhibit) the biosynthesis of one or more cytokines is not destroyed by the non-interfering substituent.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. Likewise, "alkylenyl", "alkenylenyl", and "alkynylenyl" are the divalent forms of the "alkyl", "alkenyl", and "alkynyl" groups defined above. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Similarly, the term "fluoroalkyl" is inclusive of groups that are substituted by one or more fluorine atoms, including perfluorinated groups (e.g., trifluoromethyl).

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, homopiperazinyl, and the like.

The terms "arylene," "heteroarylene," and "heterocyclylene" are the divalent forms of the "aryl," "heteroaryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

Unless otherwise specified, the aryl, heteroaryl, and heterocyclyl groups of Formulas IX-XXXIV can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, heterocyclylcarbonyl, aryloxycarbonyl, heteroaryloxycarbonyl, arylthiocarbonyl, heteroarylthiocarbonyl, alkanoyloxy, alkanoylthio, alkanoylamino, aroyloxy, aroylthio, aroylamino, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylarnino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonyl, dialkylaminocarbonyl, arylaminocarbonyl, arylalkylaminocarbonyl, alkenylaminocarbonyl, heteroarylaminocarbonyl, heteroarylalkylaminocarbonyl, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If any other groups are identified as being "substituted" or "optionally substituted", then those groups can also be substituted by one or more of the above enumerated substituents.

When a group (or substituent or variable) is present more that once in any Formula described herein, each group (or substituent or variable) is independently selected, whether explicitly stated or not. For example, for the formula —N($R_{631}$)$_2$ each $R_{631}$ group is independently selected. In another example, when an $R_{232}$ and an $R_{332}$ group both contain an $R_{432}$ group, each $R_{432}$ group is independently selected. In a further example, when more than one Y group is present (i.e. $R_{232}$ and $R_{332}$ both contain a Y group) and each Y group contains one or more $R_{832}$ groups, then each Y group is independently selected, and each $R_{832}$ group is independently selected.

In certain embodiments, the immune response modifier is selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, imidazotetrahydronaphthyridine amines, oxazoloquinoline amines, thiazoloquinoline amines, oxazolopyridine amines, thiazolopyridine amines, oxazolonaphthyridine amines, thiazolonaphthyridine amines, pyrazolopyridine amines, pyrazoloquinoline amines, tetrahydropyrazoloquinoline amines, pyrazolonaphthyridine amines, tetrahydropyrazolonaphthyridine amines, 1H-imidazo dimers fused to pyridine amines, quinoline amines, tetrahydroquinoline amines, naphthyridine amines, or tetrahydronaphthyridine amines, and combinations thereof.

In certain embodiments, the immune response modifier is selected from the group consisting of imidazoquinoline amines, tetrahydroimidazoquinoline amines, imidazopyridine amines, and combinations thereof.

In certain embodiments, the immune response modifier is selected from the group consisting of amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, 6-, 7-, 8-, or 9-aryl, heteroaryl, aryloxy or arylalkyleneoxy substituted imidazoquinoline amines, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, thioether substituted imidazopyridine amines, and combinations thereof.

In certain embodiments, the immune response modifier is selected from the group consisting of amide substituted imidazoquinoline amines, urea substituted imidazoquinoline amines, and combinations thereof.

Cosolvents

Aqueous gel formulations of the invention include a water-miscible cosolvent. The water-miscible cosolvent assists in dissolving the immune response modifier in salt form. The cosolvent can be a single component or a combination. Examples of suitable cosolvents include monopropylene glycol, dipropylene glycol, hexylene glycol, butylene glycol, glycerin, polyethylene glycol (of various molecular weights, e.g., 300 or 400), diethylene glycol monoethyl ether, and combinations thereof. Monopropylene glycol (i.e., propylene glycol) is particularly preferred as a cosolvent.

In certain embodiments, the cosolvent (or combination of cosolvents) is present in an amount of at least 10 wt-%, in other embodiments in an amount of greater than 25 wt-%, and in other embodiments at least 30 wt-%, based on the total weight of the aqueous gel. In certain embodiments, the cosolvent (or combination of cosolvents) is present in an amount of no greater than 90 wt-%, in other embodiments no greater than 80 wt-%, in other embodiments no greater than 70 wt-%, in other embodiments no greater than 60 wt-%, based on the total weight of the aqueous gel.

In certain embodiments, water is present in an amount of at least 10 wt-%, in other embodiments at least 15 wt-%, in other embodiments at least 20 wt-%, and in other embodiments at least 25 wt-%, based on the total weight of the aqueous gel. In certain embodiments, water is present in an amount of no greater than 95 wt-%, in other embodiments no greater than 90 wt-%, and in other embodiments no greater than 85 wt-%, based on the total weight of the aqueous gel.

Thickeners

Aqueous gel formulations of the invention include a negatively charged thickener, preferably at least two negatively charged thickeners (typically of differing charge density). Preferably the thickeners are mucoadhesives. Examples of suitable negatively charged thickeners include: cellulose ethers such as carboxymethylcellulose sodium; polysaccharide gums such as xanthan gum; and acrylic acid polymers (i.e., homopolymers and copolymers) made from acrylic acid crosslinked with, for example, allyl sucrose or allyl pentaerythritol such as those polymers designated as carbomers in the United States Pharmacopoeia, and acrylic acid polymers made from acrylic acid crosslinked with divinyl glycol such as those polymers designated as polycarbophils in the United States Pharmacopoeia. Combinations of such thickeners can be used if desired.

In some embodiments of the invention, the negatively charged thickeners include carboxylic acid and/or carboxylate groups. Examples of such agents include carboxymethylcellulose sodium, xanthan gum, and the acrylic acid polymers. Preferably, certain embodiments of the present invention include a combination of an acrylic acid polymer (i.e., polyacrylic acid polymer) and a polysaccharide gum (e.g., xanthan gum).

Carbomers are exemplary (and preferred) acrylic acid polymers. Suitable carbomers include, for example, those commercially available under the trade designation CARBOPOL (all available from Noveon, Inc., Cleveland, Ohio, USA). CARBOPOL polymers can provide a range of viscosities. For example, a 0.5% solution of CARBOPOL 971P or CARBOPOL 941 has a viscosity of 4,000-11,000 cPs (pH 7.5, 25° C., Brookfield viscometer at 20 rpm); a 0.5% solution of CARBOPOL 934P or CARBOPOL 974P has a viscosity of 29,400-39,400 cPs (pH 7.5, 25° C., Brookfield viscometer at 20 rpm); and a 0.5% solution of CARBOPOL 940 or CARBOPOL 980 has a viscosity of 40,000-60,000 cPs (pH 7.5, 25° C., Brookfield viscometer at 20 rpm). For certain embodiments, carbomers such as CARBOPOL 934P, CARBOPOL 974P, CARBOPOL 940, and CARBOPOL 980 are preferred. A particularly preferred carbomer is CARBOPOL 974P.

For certain embodiments, it is desirable to have a relatively highly crosslinked carbomer. Preferred relatively highly crosslinked carbomers include CARBOPOL 974P, CARBOPOL 940, and CARBOPOL 980. A particularly preferred relatively highly crosslinked carbomer is CARBOPOL 974P.

Suitable polycarbophils include, for example, those commercially available under the trade designation NOVEON polycarbophils (all available from Noveon, Inc., Cleveland, Ohio, USA). A preferred polycarbophil is NOVEON AA-1 USP Polycarbophil.

Various grades of carboxymethylcellulose sodium are commercially available that have differing aqueous viscosities. Aqueous 1% weight by volume (w/v) solutions with viscosities of 5-13,000 cps may be obtained. Examples include carboxymethylcellulose sodium, high viscosity, USP (CA194); carboxymethylcellulose sodium, medium viscosity, USP (CA192); and carboxymethylcellulose sodium, low viscosity, USP (CA193); all of which are available from Spectrum Chemicals and Laboratory Products, Inc., Gardena, Calif., USA; and AKUCELL AF 3085 (high viscosity), AKUCELL AF 2785 (medium viscosity), and AKUCELL AF 0305 (low viscosity), all of which are available from Akzo Nobel Functional Chemicals, Amersfoort, The Netherlands.

In certain embodiments, the thickener system includes a non-ionic thickener. Examples of suitable non-ionic thickeners include hydroxyethyl cellulose, hydroxymethyl cellulose, and hydroxypropyl cellulose. If included, the weight ratio of non-ionic thickener to negatively charged thickener (total weight of all negatively charged thickeners if more than one negatively charged thickener is included) is within the range of 1:4 to 1:10. In certain embodiments, the weight ratio is within the range of 1:4 to 1:7.

Hydroxypropyl cellulose is commercially available in a number of different grades that have various solution viscosities. Examples include KLUCEL HF and KLUCEL MF, both of which are available from the Aqualon Division of Hercules Incorporated, Wilmington, Del., USA.

In certain embodiments, the thickener system includes a polysaccharide gum and an acrylic acid polymer. Preferably, the weight ratio of polysaccharide gum to acrylic acid polymer is within a range of 1:20 to 20:1. In certain embodiments, the weight ratio is within a range of 1:10 to 10:1, in other embodiments the weight ratio is within a range of 1:5 to 5:1, in other embodiments the weight ratio is within a range of 1:3 to 3:1, and in other embodiments the weight ratio is within a range of 1:2 to 2:1. A particularly preferred ratio is 1:2.

The thickener system is present in formulations of the invention in an amount sufficient to bring the viscosity to a level of at least than 1000 Centipoise (cps), preferably at least 5,000 cps, more preferably at least 8000 cps, and most preferably at least 10,000 cps. The viscosity is determined at 20±0.5° C. using a Haake RS series rheometer equipped with a 35 mm 2° cone using a controlled rate step test between 1 and 80 s$^{-1}$ with an interpolation at 16 s$^{-1}$ for viscosity versus shear rate.

In certain embodiments, the amount or concentration of the thickener system is at least 0.1 wt-%, in other embodiments at least 0.5 wt-%, in other embodiments at least 1.0 wt-%, and in other embodiments at least 1.5 wt-%, based on the total weight of the aqueous gel. In certain embodiments, the amount of the thickener system is no greater than 7 wt-%, in other embodiments no greater than 6 wt-%, in other embodiments no greater than 5 wt-%, and in other embodiments no greater than 4 wt-%, based on the total weight of the aqueous gel.

pH Adjusting Agents and Buffers

Aqueous gel formulations of the invention can additionally include a pharmaceutically acceptable pH adjusting agent to adjust the pH of the formulation to the desired range. Generally, the pH is at least 2, and preferably at least 3. Generally, the pH is no greater than 6, preferably no greater than 5, and more preferably no greater than 4. The pH adjusting agent may be any pharmaceutically acceptable acid or base. Examples of suitable pH adjusting agents include hydrochloric acid, sodium hydroxide, tromethamine, and potassium hydroxide. Combinations of such agents can be used if desired.

Aqueous gel formulations of the invention can additionally include a pharmaceutically acceptable buffer to maintain the pH of the formulations in the desired range (preferably, 2 to 6, and more preferably 3 to 4). The buffer may be any pharmaceutically acceptable buffer that provides one or more of the desired pH ranges. Examples of suitable buffers include buffers containing lactic acid, tartaric acid, citric acid, and succinic acid. Combinations of buffers can be used if desired. The buffers can also function as tonicity adjusting agents.

Preservatives

Aqueous gel formulations of the invention can additionally include a preservative. The preservative includes one or more compounds that inhibit microbial growth (e.g., fungal and bacterial growth) within the composition. Suitable preservatives are water soluble and include quaternary ammonium compounds (e.g., benzalkonium chloride), benzethonium chloride, parabens (e.g., methylparaben, propylparaben), boric acid, isothiazolinone, organic acids (e.g., sorbic acid), alcohols (e.g., phenyl ethyl alcohol, cresol, chlorobutanol, benzyl alcohol), carbamates, chlorhexidine, and combinations thereof. Preferably, the preservative is methylparaben, propylparaben, or combinations thereof. Certain water-miscible cosolvents, such as glycerin or propylene glycol, also have antimicrobial properties.

In certain embodiments, the preservative (or combination of preservatives) is present in an amount of at least 0.005 wt-%, in other embodiments at least 0.01 wt-%, in other embodiments at least 0.015 wt-%, and in other embodiments at least 0.02 wt-%, based on the total weight of the aqueous gel. In certain embodiments, the preservative (or combination of preservatives) is present in an amount of no greater than 1.0 wt-%, in other embodiments at most 0.75 wt-%, in other embodiments at most 0.5 wt-%, and in other embodiments no greater than 0.4 wt-%, based on the total weight of the aqueous gel.

Chelating Agents

Aqueous gel formulations of the invention can additionally include a chelating agent. Chelating agents are compounds that complex metal ions. Examples of suitable chelating agents include ethylenediaminetetracetic acid (EDTA) and derivatives thereof such as the disodium salt, ethylenediaminetetracetic acid disodium salt dehydrate, and combinations thereof. Preferably, the chelating agent is ethylenediaminetetracetic acid disodium salt dihydrate (edetate disodium).

In certain embodiments, the chelating agent (or combination of chelating agents) is present in an amount of at least 0.001 wt-%, in other embodiments at least 0.01 wt-%, and in other embodiments at least 0.02 wt-%, based on the total weight of the aqueous gel. In certain embodiments, the chelating agent (or combination of chelating agents) is present in an amount of no greater than 2.0 wt-%, in other embodiments no greater than 1.5 wt-%, and in other embodiments no greater than 1.0 wt-%, based on the total weight of the aqueous gel.

Applications

Aqueous gel formulations of the present invention can be used to treat or prevent conditions associated with mucosal tissue. In some embodiments, the invention provides methods that are particularly advantageous for the topical application to the cervix for treatment of cervical conditions such as cervical dysplasias including dysplasia associated with human papillomavirus (HPV), low-grade squamous intraepithelial lesions, high-grade squamous intraepithelial lesions, atypical squamous cells of undetermined significance (typically, with the presence of high-risk HPV), and cervical intraepithelial neoplasia (CIN).

The present invention also provides methods of treating a mucosal associated condition. Alternatively stated, the present invention provides methods of treating a condition associated with mucosal tissue.

In the methods of the present invention, the aqueous gels of the present invention may be applied once a week or several times a week. For example, the aqueous gel may be applied twice a week, three times a week, five times a week, or even daily.

In the methods of the present invention, the applications of the aqueous gels of the present invention may extend for a total time period of at least one week, at least two weeks, at least three weeks, at least one month, at least two months, at least three months, or more, depending on the desired treatment regimen.

The actual dosing (treatment) regimen used for a given condition or subject may depend at least in part on many factors known in the art, including, but not limited to, the physical and chemical nature of the IRM compound, the nature of the delivery material, the amount of the IRM compound being administered, the state of the subject's immune system (e.g., suppressed, compromised, stimulated), the method of administering the IRM compound, and the species to which the IRM compound is being administered.

The methods of the present invention may be applicable for any suitable subject. Suitable subjects include, but are not limited to, animals such as, but not limited to, humans, non-human primates, rodents, dogs, cats, horses, pigs, sheep, goats, cows, or birds.

The methods of the present invention are suitable for a variety of medical objectives, including therapeutic, prophylactic (e.g., as a vaccine adjuvant), or diagnostic. As used herein, "treating" a condition or a subject includes therapeutic, prophylactic, and diagnostic treatments.

The term "an effective amount" (e.g., therapeutically or prophylactically) means an amount of the compound sufficient to induce a desired (e.g., therapeutic or prophylactic) effect, such as cytokine induction, inhibition of TH2 immune response, antiviral or antitumor activity, reduction or elimination of neoplastic cells. The amount of the IRM compound that will be therapeutically effective in a specific situation will depend on such things as the activity of the particular compound, the dosing regimen, the application site, the particular formulation and the condition being treated. As such, it is generally not practical to identify specific administration amounts herein; however, those skilled in the art will be able to determine appropriate therapeutically effective amounts based on the guidance provided herein and information available in the art pertaining to these compounds.

The aqueous gels of the present invention may be used for the application of an IRM compound to the affected area of a subject for treating a dermal and/or mucosal condition. Examples of such conditions include herpes, keloids, warts, molluscum, or combinations thereof. It will be understood by one of skill in the art that such conditions (e.g., warts) can be on both mucosal and dermal tissue.

The aqueous gels of the present invention may be used for the application of an IRM compound to mucosal tissue for the treatment of a mucosal associated condition.

As used herein, a "mucosal associated condition" means an inflammatory, infectious, neoplastic, or other condition that involves mucosal tissue or that is in sufficient proximity to a mucosal tissue to be affected by a therapeutic agent topically applied to the mucosal tissue. Examples of such conditions include a papilloma virus infection of the cervix, cervical dysplasias including dysplasia associated with human papillomavirus (HPV), low-grade squamous intraepithelial lesions, high-grade squamous intraepithelial lesions, atypical squamous cells of undetermined significance (typically, with the presence of high risk HPV), and cervical intraepithelial neoplasia, an atopic allergic response, allergic rhinitis, a neoplastic lesion, and a premalignant lesion.

As used herein, "mucosal tissue" includes mucosal membranes such as buccal, gingival, nasal, ocular, tracheal, bronchial, gastrointestinal, rectal, urethral, ureteral, vaginal, cervical, and uterine mucosal membranes. For example, one could treat oral lesions, vaginal lesions, or anal lesions by the methods described. One could also use the methods in combination with mucosal application of vaccines.

In one embodiment, the IRM compound can be applied to vaginal or supravaginal mucosal tissue for the treatment of a cervical dysplasia. In other embodiments, an IRM can be applied to the mucosal tissue of the rectum for the treatment of, e.g., anal canal condyloma.

Cervical dysplasias to be treated by the methods of the present invention preferably include dysplastic conditions such as low-grade squamous intraepithelial lesions, high-grade squamous intraepithelial lesions, atypical squamous cells of undetermined significance (typically, with the presence of high-risk HPV), and cervical intraepithelial neoplasia (CIN).

Approximately 16,000 new cases of invasive cancer of the cervix are diagnosed each year in the U.S. despite extensive screening of women to detect predictive cellular changes. There are also about 3,000 deaths due to cervical cancer in the U.S. alone and this is usually secondary to not detecting the primary cancerous lesion in a timely manner.

The Papanicoulaou Test (Pap smear) is the screening test that has been accepted since the 1950s as the method to detect abnormal cells of the cervix, including inflammation and dysplasia, which includes cervical cancer. This screening test has been widely adopted in industrialized countries and has had a profound impact on mortality associated with cervical cancers. An abnormal Pap smear prompts close observation for disease progression with the potential for the therapeutic interventions of destruction or excision of cancerous or pre-cancerous tissues. These excisional treatments are expensive, uncomfortable and associated with failure rates that range from 2% to 23% and with higher failure rates reported for the more advanced lesions. Failure rates have recently been documented to approximate 10% following laser treatment.

The etiologic agent for cervical cancer was originally thought to be the herpes virus. However, there was a gradual shift from this focus on herpes virus to the human papillomavirus (HPV). Improved experimental methods over the recent past have allowed the characterization of a full spectrum of HPV subtypes, which has resulted in the conclusion that the high risk HPV types (e.g., HPV 16, 18, and less frequently 31, 33, 35, 45) are very likely the exclusive initiating factor (i.e., oncogenic agent) for cervical dysplasia and subsequent cancers. The mechanism of HPV transformation of the normal cell to a dysplastic cell is associated with the HPV encoded oncoproteins (E6 and E7) from the high risk genotypes binding the cell's tumor suppressor gene products p53 and Rb resulting in disruption of the cell cycle control mechanism in which p53 and Rb play an important role. In addition, the application of these molecular methods has resulted in the epidemilogic observation that HPV is isolated from approximately 93% of cervical tumors, which has further strengthened the generally accepted conclusion that HPV infection is the most important initiating agent for cervical cancer.

Exposure to HPV is common in sexually active women, but it does not invariably lead to dysplasia or cancer in most of the exposed women. Infected women who harbor persistent viral DNA have about five times the chance of persistent dysplasia compared to women who are able to eradicate the virus. The importance of cell-mediated immune response to HPV infection is illustrated by the observation that the antibody mediated immune response is not effective in eliminating established infections as is demonstrated by the fact that patients with invasive cervical cancer often exhibit high antibody levels against the viral E6 and E7 proteins. This particular antibody response probably reflects extensive antigen exposure in the face of increasing tumor burden. In contrast to the apparently inconsequential effect of the humoral immune response; the cell-mediated immune response (Th-1-Type Response) appears to be effective in controlling tumor progression. Regression of intraepithelial lesions is accompanied by a cellular infiltrate consisting of $CD4^+$ T-cells, $CD8^+$ T-cells, natural killer cells (NK) and macrophages. This inflammatory infiltrate was usually associated with tumor regression that is in contrast to women who lack the ability to mount this inflammatory response and who experience disease progression. In addition, patients with a defect in cell-mediated immunity have increased cervical cancer rates, whereas those with defects in the production of antibody do not exhibit the same susceptibility.

Aqueous gels of the present invention may be applied to mucosal tissue with the use of a delivery device. Suitable devices include barrel type applicators, cervical caps, diaphragms, and solid matrices such as tampons, cotton sponges, cotton swabs, foam sponges, and suppositories. The IRM can be removed by withdrawing the device from contact with the mucosal tissue, if desired.

In some embodiments the device can be used in combination with the aqueous gel formulation. In one embodiment, a gel containing an IRM compound can be placed into the concave region of a cervical cap, which is then place directly over the cervix. In another embodiment, a cotton or foam sponge can be used in combination with an aqueous gel of the present invention.

In some embodiments, an applicator may be used to place the device and/or gel in the proper location on the mucosal tissue. Examples of such applicators include, for example, paperboard or plastic tube applicators commonly used for inserting tampons or suppositories. A preferred applicator is a barrel type applicator, which may be prefilled or supplied in a kit together with a container of gel and filled by the patient.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

The IRMs used to prepare the gels in the following examples are shown in Table 1.

TABLE 1

| IRM | Chemical Name | Reference |
|---|---|---|
| IRM1 | 4-(4-amino-2-propyl-1H-imidazo[4,5-c]quinolin-1-yl)-N-propylbutyramide | International Publication No. WO2005/094531 Example 2 |

TABLE 1-continued

| IRM | Chemical Name | Reference |
|---|---|---|
| IRM2 | N-[2-(4-amino-7-benzyloxy-2-ethoxymethyl-1H-imidazo[4,5-c]quinolin-1-yl)-1,1-dimethylethyl]acetamide | International Publication No. WO2005/020999 Example 142 |
| IRM3 | 3-(4-amino-2-propyl-1H-imidazo[4,5-c]quinolin-1-yl)propionamide hydrochloride | International Publication No. WO2005/094531 Example 18 |
| IRM4 | N-[2-(4-amino-2-ethoxymethyl-1H-imidazo[4,5-c]quinolin-1-yl)ethyl]-N'-isopropylurea | U.S. Pat. No. 6,541,485[#] |
| IRM5 | N-[4-(4-amino-2-buytl-1H-imidazo[4,5-c]quinolin-1-yl)butyl]methanesulfonamide | U.S. Pat. No. 6,331,539 Example 6 |
| IRM6 | N-{4-[4-amino-2-(2-methoxyethyl)-1H-imidazo[4,5-c]quinolin-1-yl]butyl}methanesulfonamide | U.S. Pat. No. 6,331,539 Example 111 |
| IRM7 | 1-(2-methylpropyl)-1H-imidazo[4,5-c]quinolin-4-amine (imiquimod) | U.S. Pat. No. 4,689,338 Example 99 |
| IRM8 | 2-propylthiazolo[4,5-c]quinolin-4-amine hydrochloride | U.S. Pat. No. 6,110,929 Example 14 |

[#]IRM4 is not specifically exemplified but can be readily prepared using the synthetic methods disclosed in the cited reference.

Test Method

In the examples below the serum and intravaginal cytokine data were obtained using the following general test method.

Rats were acclimated to collars (Lomir Biomedical, Malone, N.Y.) around the neck on two consecutive days prior to actual dosing. Rats were collared to prevent ingestion of the drug. Animals were then dosed intravaginally with 50 μL of gel. Single dosed rats received one intravaginal dose with samples collected at various times following dosing. Multiple dosed rats were dosed as described in the examples below with samples collected at various times following the final dose. Blood was collected by cardiac puncture. Blood was allowed to clot briefly at room temperature and serum was separated from the clot via centrifugation. The serum was stored at −20° C. until it was analyzed for cytokine concentrations.

Following blood collection, the rats were euthanized and their vaginal tract, including the cervix, was then removed and the tissue was weighed, placed in a sealed 1.8 mL cryovial and flash frozen in liquid nitrogen. The frozen vaginal tissue sample was then suspended in 1.0 mL of RPMI medium (Celox, St. Paul, Minn.) containing 10% fetal bovine serum (Atlas, Fort Collins, Colo.), 2 mM L-glutamine, penicillin/streptomycin and 2-mercaptoethanol (RPMI complete) combined with a protease inhibitor cocktail set III (Calbiochem, San Diego, Calif.). The tissue was homogenized using a Tissue Tearor (Biospec Products, Bartlesville, Okla.) for approximately one minute. The tissue suspension was then centrifuged at 2000 rpm for 10 minutes under refrigeration to pellet the debris, and the supernatant collected and stored at −20° C. until analyzed for cytokine concentrations.

ELISA kits for rat tumor necrosis factor-alpha (TNF) were purchased from BD PharMingen (San Diego, Calif.) and the rat monocyte chemoattractant protein-1 (MCP-1) ELISA kits were purchased from BioSource Intl. (Camarillo, Calif.). Both kits were performed according to manufacturer's specifications. Results for both TNF and MCP-1 are expressed in pg/mL and are normalized per 200 mg of tissue.

The sensitivity of the TNF ELISA, based on the lowest value used to form the standard curve, is 32 pg/mL and for the MCP-1 ELISA it is 12 pg/mL.

Examples 1 and 2

The gels shown in Table 2 below were prepared using the following method.
Step 1: The parabens were dissolved in the propylene glycol.
Step 2: The IRM was combined with the aqueous ethanesulfonic acid and a portion of the water.
Step 3: The solution from step 1 was combined with the mixture from step 2.
Step 4: Edetate disodium was dissolved in water. The carbomer was added to the solution and stirred until well hydrated.
Step 5: The dispersion from step 4 was combined with the mixture from step 3.
Step 6: 20% tromethamine was added to adjust the pH.
Step 7: Sufficient water was added to adjust the final weight and the gel was mixed well.

TABLE 2

| | Gels (% w/w) | |
|---|---|---|
| Ingredient | Ex 1 IRM1 | Ex 2 IRM2 |
| IRM | 0.1 | 0.1 |
| 0.25N ethanesulfonic acid | 0.594 | 0.452 |
| Carbomer 974P | 2.1 | 2.1 |
| Propylene glycol | 15 | 15 |
| Methylparaben | 0.15 | 0.15 |
| Propylparaben | 0.03 | 0.03 |
| Edetate disodium | 0.05 | 0.05 |
| 20% Tromethamine solution | 1.5 | 1.5 |
| Purified water | 80.48 | 80.62 |
| pH | 3.95 | 4.07 |

Example 3

The gel shown in Table 3 below was prepared using the following method.
Step 1: The parabens were dissolved in the propylene glycol.
Step 2: IRM3 was combined with a portion of the water.
Step 3: The solution from step 1 was combined with the mixture from step 2 and heated to 55° C. and ultrasonicated.
Step 4: Edetate disodium was dissolved in water. The carbomer was added to the solution and stirred until well hydrated.
Step 5: The dispersion from step 4 was combined with the mixture from step 3.
Step 6: 20% tromethamine was added to adjust the pH.
Step 7: Sufficient water was added to adjust the final weight and the gel was mixed well.

TABLE 3

| Ingredient | (% w/w) |
|---|---|
| IRM 3 | 0.1 |
| Carbomer 974P | 2.1 |
| Propylene glycol | 15 |
| Methylparaben | 0.15 |
| Propylparaben | 0.03 |
| Edetate disodium | 0.05 |
| 20% Tromethamine solution | 1.5 |

TABLE 3-continued

| Ingredient | (% w/w) |
| --- | --- |
| Purified water | 80.65 |
| pH | 3.99 |

The ability of the gels of Examples 1-3 to induce cytokines was determined using the test method described above. The animals received an intravaginal dose once a day on day 0 and on day 3 for a total of 2 doses. The results are shown in Table 4 below where each value is the mean of 3 animals±SEM (standard error of the mean).

TABLE 4

| Time (hours) Post Dose | Gel | Cytokine Concentrations | | | |
| --- | --- | --- | --- | --- | --- |
| | | TNF (pg/mL) | | MCP-1 (pg/mL) | |
| | | Serum | Tissue | Serum | Tissue |
| 2 | Example 1 | 36 ± 18 | 356 ± 14 | 136 ± 23 | 226 ± 35 |
| 2 | Example 2 | 84 ± 16 | 1736 ± 794 | 147 ± 33 | 588 ± 221 |
| 2 | Example 3 | 97 ± 6 | 568 ± 458 | 114 ± 33 | 282 ± 192 |
| 4 | Example 1 | 53 ± 10 | 273 ± 172 | 77 ± 28 | 501 ± 291 |
| 4 | Example 2 | 79 ± 6 | 1064 ± 290 | 15 ± 15 | 1839 ± 113 |
| 4 | Example 3 | 49 ± 9 | 188 ± 48 | 161 ± 13 | 637 ± 252 |
| 6 | Example 1 | 44 ± 3 | 210 ± 19 | 161 ± 38 | 756 ± 205 |
| 6 | Example 2 | 73 ± 10 | 743 ± 211 | 260 ± 14 | 1857 ± 276 |
| 6 | Example 3 | 56 ± 13 | 105 ± 37 | 218 ± 63 | 444 ± 298 |
| 4 | [1]Vehicle | 101 ± 32 | 94 ± 10 | 173 ± 20 | 176 ± 59 |

[1]Vehicle (2.1% carbomer 974, 15% propylene glycol, 0.15% methylparaben, 0.03% propylparaben, 0.05% edetate sodium, 1.35% 20% tromethamine solution, and 81.32% water)

Examples 4-6

The gels in Table 5 below were prepared using the following general method.
Step 1: The parabens were dissolved in the propylene glycol.
Step 2: IRM4 was dissolved in the aqueous ethanesulfonic acid.
Step 3: The solution from step 1 was combined with the solution from step 2.
Step 4: Edetate disodium was dissolved in water. The carbomer and xanthan gum, if used, were added to the solution and stirred until well hydrated.
Step 5: The dispersion from step 4 was combined with the solution from step 3.
Step 6: 20% tromethamine was added to adjust the pH.
Step 7: Sufficient water was added to adjust the final weight and the gel was mixed well.

TABLE 5

| Ingredient | Gels (% w/w) | | |
| --- | --- | --- | --- |
| | Ex 4 | Ex 5 | Ex 6 |
| IRM4 | 0.01 | 0.1 | 1 |
| 0.5N ethanesulfonic acid | 0.054 | 0.54 | 5.4 |
| Carbomer 974P | 1.7 | 1.7 | 2 |
| Xanthan gum | 0.0 | 0.0 | 0.56 |
| Propylene glycol | 15 | 15 | 30 |
| Methylparaben | 0.15 | 0.15 | 0.15 |
| Propylparaben | 0.03 | 0.03 | 0.03 |
| Edetate disodium | 0.05 | 0.05 | 0.05 |
| 20% Tromethamine solution | 0.7 | 0.5 | 1.9 |
| Purified water | 82.31 | 81.93 | 58.91 |
| pH | 3.9 | 3.9 | 4.3 |

The ability of the gels of Examples 4-6 to induce cytokines following a single dose was determined using the test method described above. The results are shown in Table 6 below where each value is the mean of 5 animals±SEM.

TABLE 6

| Time (hours) Post Dose | Gel | Cytokine Concentrations | | | |
| --- | --- | --- | --- | --- | --- |
| | | TNF (pg/mL) | | MCP-1 (pg/mL) | |
| | | Serum | Tissue | Serum | Tissue |
| 2 | Example 4 | 16 ± 2 | 331 ± 24 | 96 ± 4 | 134 ± 57 |
| 2 | Example 5 | 19 ± 6 | 433 ± 64 | 91 ± 11 | 298 ± 104 |
| 2 | Example 6 | 45 ± 21 | 853 ± 150 | 90 ± 6 | 501 ± 111 |
| 4 | Example 4 | 11 ± 6 | 257 ± 9 | 115 ± 10 | 112 ± 41 |
| 4 | Example 5 | 30 ± 6 | 397 ± 32 | 123 ± 13 | 462 ± 159 |
| 4 | Example 6 | 70 ± 32 | 700 ± 86 | 103 ± 9 | 866 ± 150 |
| 8 | Example 4 | 13 ± 5 | 297 ± 11 | 142 ± 13 | 283 ± 84 |
| 8 | Example 5 | 21 ± 5 | 275 ± 21 | 146 ± 16 | 337 ± 96 |
| 8 | Example 6 | 14 ± 2 | 557 ± 232 | 171 ± 23 | 641 ± 144 |
| 4 | [1]Vehicle | 37 ± 14 | 255 ± 15 | 108 ± 16 | 9 ± 3 |

[1]Vehicle (2% carbomer 974, 30% propylene glycol, 0.15% methylparaben, 0.03% propylparaben, 0.05% edetate sodium, 0.3% of 20% tromethamine solution, and 67.47% water)

Examples 7 and 8

The gels shown in Table 7 were prepared using the following general method.
Step 1: IRM2 was combined with the aqueous ethanesulfonic acid and a portion of the water. The combination was mixed until the IRM was dissolved.
Step 2: The parabens were dissolved in the propylene glycol.
Step 3: Edetate sodium was dissolved in water. The carbomer was added and the mixture was stirred until the carbomer was hydrated.
Step 4: The solution from step 2 was added to the solution from step 1 and the combination was mixed until uniform.
Step 5: The dispersion from step 3 was added to the solution from step 4 and the combination was mixed until a uniform, smooth gel was obtained.
Step 6: Sufficient 20% tromethamine was added to adjust the pH to about 4.
Step 7: Sufficient water was added to adjust the final weight and the gel was mixed well until uniform.

TABLE 7

| Ingredient | Gels (% w/w) | |
| --- | --- | --- |
| | Ex 7 | Ex 8 |
| IRM2 | 0.01 | 0.1 |
| Ethanesulfonic acid (0.5M + 5% extra) | 0.0455 | 0.455 |
| Carbomer 974P | 2.1 | 2.1 |
| Propylene glycol | 15 | 15 |
| Methylparaben | 0.15 | 0.15 |
| Propylparaben | 0.03 | 0.03 |
| Edetate disodium | 0.05 | 0.05 |
| 20% Tromethamine solution | qs pH 4 | qs pH 4 |
| Purified water | qs 100 | qs 100 |
| pH | 4.1 | 4.2 |

Example 9

The gel shown in Table 8 was prepared using the following general method.
Step 1: IRM2 was combined with the aqueous ethanesulfonic acid and a portion of the water. The combination was mixed until the IRM was dissolved.

Step 2: The parabens were dissolved in the propylene glycol.
Step 3: Edetate sodium was dissolved in water. The carbomer was added and the mixture was stirred until the carbomer was hydrated.
Step 4: The solution from step 2 was added to the solution from step 1 and the combination was mixed until uniform.
Step 5: The dispersion from step 3 was added to the solution from step 4. The combination was mixed well resulting in a milky, fluid dispersion.
Step 6: Sufficient 20% tromethamine was added to adjust the pH to about 4 and the dispersion thickened and foamed.
Step 7: Xanthan gum was mixed with water and then added to the dispersion from step 6. The mixture was heated at 50° C. with stirring for 4 hours. The gel was allowed to cool to ambient temperature overnight with stirring.

TABLE 8

| Ingredient | (% w/w) |
| --- | --- |
| IRM4 | 1 |
| Ethanesulfonic acid (0.5M + 5% extra) | 4.565 |
| Carbomer 974P | 2.1 |
| Xanthan gum | 0.2 |
| Propylene glycol | 15 |
| Methylparaben | 0.15 |
| Propylparaben | 0.03 |
| Edetate disodium | 0.05 |
| 20% Tromethamine solution | qs pH 4 |
| Purified water | qs 100 |
| pH | 4.0 |

The ability of the gels of Examples 7-9 to induce cytokines following a single dose was determined using the test method described above. The gel of Example 9 was stirred prior to dosing to minimize air bubbles. The results are shown in Table 9 below where each value is the mean of 6 animals±SEM.

TABLE 9

| Time (hours) Post Dose | Gel | Cytokine Concentrations | | | |
| --- | --- | --- | --- | --- | --- |
| | | TNF (pg/mL) | | MCP-1 (pg/mL) | |
| | | Serum | Tissue | Serum | Tissue |
| 0.5 | Example 7 | 159 ± 49 | 315 ± 63 | 212 ± 66 | 34 ± 1 |
| 0.5 | Example 8 | 716 ± 341 | 288 ± 22 | 239 ± 57 | 59 ± 21 |
| 0.5 | Example 9 | 359 ± 220 | 375 ± 85 | 130 ± 33 | 39 ± 2 |
| 1 | Example 7 | 199 ± 76 | 343 ± 79 | 110 ± 39 | 41 ± 7 |
| 1 | Example 8 | 237 ± 123 | 340 ± 93 | 156 ± 65 | 34 ± 2 |
| 1 | Example 9 | 306 ± 160 | 681 ± 222 | 119 ± 40 | 74 ± 30 |
| 4 | Example 7 | 165 ± 50 | 915 ± 175 | 261 ± 64 | 476 ± 127 |
| 4 | Example 8 | 105 ± 10 | 1165 ± 250 | 247 ± 32 | 1098 ± 307 |
| 4 | Example 9 | 233 ± 144 | 1628 ± 202 | 254 ± 38 | 1217 ± 271 |
| 8 | Example 7 | 133 ± 18 | 1190 ± 368 | 279 ± 27 | 583 ± 67 |
| 8 | Example 8 | 166 ± 51 | 1029 ± 268 | 259 ± 36 | 923 ± 131 |
| 8 | Example 9 | 159 ± 44 | 1336 ± 149 | 325 ± 44 | 1895 ± 254 |
| 4 | [1]Vehicle | 125 ± 0 | 642 ± 101 | 191 ± 39 | 88 ± 41 |

[1]Vehicle (2.1% carbomer 974, 0.4% xanthan gum, 15% propylene glycol, 0.15% methylparaben, 0.03% propylparaben, 0.05% edetate sodium, 20% tromethamine solution qs to pH 4.0, and water qs to 100%)

Examples 10 and 11

The gels shown in Table 10 were prepared using the following general method.
Step 1: The IRM was combined with the aqueous ethanesulfonic acid and the combination was mixed until the IRM was dissolved.
Step 2: The parabens were dissolved in the propylene glycol.
Step 3: Edetate sodium was dissolved in the bulk of the water. The carbomer was added and the mixture was stirred until the carbomer was hydrated.
Step 4: The solution from step 2 was added to the solution from step 1 and the combination was mixed until uniform.
Step 5: The dispersion from step 3 was added in portions to the solution from step 4 and the combination was mixed well.
Step 6: 20% tromethamine was added to adjust the pH to about 4.
Step 7: Sufficient water was added to adjust the final weight and the gel was mixed well until uniform.

TABLE 10

| | Gels (% w/w) | |
| --- | --- | --- |
| Ingredient | Ex 10 | Ex 11 |
| IRM | 0.05 IRM5 | 0.5 IRM6 |
| Ethanesulfonic acid (0.05N) | 2.76 | 0 |
| Ethanesulfonic acid (0.02N) | 0 | 6.8 |
| Carbomer 974P | 3.3 | 3.5 |
| Propylene glycol | 15 | 15 |
| Methylparaben | 0.15 | 0.15 |
| Propylparaben | 0.03 | 0.03 |
| Edetate disodium | 0.05 | 0.05 |
| 20% Tromethamine solution | 3.2 | 4.5 |
| Purified water | qs 100 | qs 100 |
| pH | * | 4.4 |

* Not measured

The ability of the gels of Examples 10 and 11 to induce cytokines following a single dose was determined using the test method described above except that the dose was 100 µL instead of 50 µL. The results are shown in Table 11 below where each value is the mean of 3 animals±SEM (standard error of the mean).

TABLE 11

| Time (hours) Post Dose | Gel | Cytokine Concentrations | | | |
| --- | --- | --- | --- | --- | --- |
| | | TNF (pg/mL) | | MCP-1 (pg/mL) | |
| | | Serum | Tissue | Serum | Tissue |
| 2 | Example 10 | 0 ± 0 | 230 ± 23 | 83 ± 7 | 276 ± 27 |
| 2 | Example 11 | 33 ± 33 | 101 ± 28 | 96 ± 7 | 31 ± 4 |
| 4 | Example 10 | 0 ± 0 | 169 ± 52 | 123 ± 36 | 411 ± 241 |
| 4 | Example 11 | 0 ± 0 | 214 ± 19 | 87 ± 6 | 197 ± 72 |
| 2 | Untreated | 0 ± 0 | 90 ± 17 | 77 ± 7 | 26 ± 2 |

Example 12

The gel shown in Table 12 was prepared using the following general method.
Step 1: IRM7 was combined with the aqueous methanesulfonic acid and mixed. Water was added in portions until the IRM was completely dissolved.
Step 2: The edetate sodium was dissolved in the bulk of the water.
Step 3: The hydroxypropyl cellulose was combined with propylene glycol (about two thirds of the amount used to achieve the final weight percent) and the combination was mixed to form a slurry.
Step 4: The carbomer was slowly added to the solution from step 2. The mixture was stirred until the carbomer was fully hydrated.

Step 5: The slurry from step 3 was added to the mixture from step 4 and mixed thoroughly.

Step 6: The parabens were dissolved in propylene glycol (about one third of the amount used to achieve the final weight percent).

Step 7: The solution from step 6 was added to the solution from step 1 and thoroughly mixed.

Step 8: The solution from step 7 was slowly added to the mixture from step 5 with mixing.

Step 9: 20% tromethamine was added to adjust the pH to 4.

TABLE 12

| Ingredient | (% w/w) |
| --- | --- |
| IRM7 | 0.05 |
| Methanesulfonic acid (0.15M) | 14.6 |
| Carbomer 974P | 3.5 |
| [1]Hydroxypropyl cellulose | 0.50 |
| Propylene glycol | 15 |
| Methylparaben | 0.15 |
| Propylparaben | 0.03 |
| Edetate disodium | 0.05 |
| 20% Tromethamine solution | qs pH 4 |
| Purified water | qs 100 |
| pH | 4.0 |

[1]KLUCEL HF

Examples 13-15

The gels in Table 13 below were prepared using the following general method.

Step 1: The parabens were dissolved in propylene glycol (about one third of the amount used to achieve the final weight percent).

Step 2: IRM8 and a small portion of the water were added to the solution from step 1. The mixture was stirred until the IRM was completely dissolved.

Step 3: The edetate sodium was dissolved in the bulk of the water.

Step 4: The hydroxypropyl cellulose was slowly added with stirring to propylene glycol (about two thirds of the amount used to achieve the final weight percent).

Step 5: The mixture from step 4 was added to the solution from step 3.

Step 6: The carbomer was slowly added with stirring to the mixture from step 5. Stirring was continued until the carbomer was fully hydrated.

Step 7: About half of the 20% tromethamine solution was slowly added with stirring to the mixture from step 6.

Step 8: The solution from step 2 was slowly added with stirring to the mixture from step 7.

Step 9: The remainder of the 20% tromethamine solution was slowly added with stirring to the mixture from step 8. Stirring was continued until a uniform gel was obtained.

TABLE 13

| | Gels (% w/w) | | |
| --- | --- | --- | --- |
| Ingredient | Ex 13 | Ex 14 | Ex 15 |
| IRM8 | 0.0574 | 0.574 | 1.148 |
| Carbomer 974P | 2.00 | 3.50 | 3.50 |
| Hydroxypropyl cellulose (HF grade) | 0.50 | 0.50 | 0.50 |
| Propylene glycol | 15.0 | 15.0 | 15.0 |
| Methylparaben | 0.15 | 0.15 | 0.15 |
| Propylparaben | 0.03 | 0.03 | 0.03 |
| Edetate disodium | 0.05 | 0.05 | 0.05 |
| 20% Tromethamine solution | 0.94 | 3.47 | 5.00 |
| Purified water | qs 100 | qs 100 | qs 100 |

Example 16

The gel shown in Table 14 below was prepared using the following general method of Examples 13-15 except that all of the 20% tromethamine solution was added in step 7.

TABLE 14

| Ingredient | (% w/w) |
| --- | --- |
| IRM8 | 0.00574 |
| Carbomer 974P | 2.0 |
| Hydroxypropyl cellulose (HF grade) | 0.5 |
| Propylene glycol | 15.0 |
| Methylparaben | 0.15 |
| Propylparaben | 0.03 |
| Edetate disodium | 0.05 |
| 20% Tromethamine solution | 0.94 |
| Purified water | qs 100 |
| pH | 4.0 |

The ability of the gels of Examples 13-16 to induce cytokines following a single dose was determined using the test method described above except that the dose was 100 μL instead of 50 μL. The results are shown in Table 15 below where each value is the mean of 6 animals±SEM (standard error of the mean).

TABLE 15

| Time | | Cytokine Concentrations | | | |
| --- | --- | --- | --- | --- | --- |
| (hours) | | TNF (pg/mL) | | MCP-1 (pg/mL) | |
| Post Dose | Gel | Serum | Tissue | Serum | Tissue |
| 2 | Example 16 | 2 ± 1 | 214 ± 29 | 83 ± 12 | 315 ± 122 |
| 2 | Example 13 | 0 ± 0 | 285 ± 52 | 115 ± 25 | 609 ± 111 |
| 2 | Example 14 | 2 ± 1 | 328 ± 18 | 98 ± 13 | 895 ± 132 |
| 2 | Example 15 | 3 ± 1 | 428 ± 27 | 95 ± 21 | 1202 ± 72 |
| 2 | [1]Vehicle | 7 ± 5 | 159 ± 18 | 94 ± 16 | 47 ± 7 |
| 4 | Example 16 | 0 ± 0 | 234 ± 34 | 118 ± 21 | 727 ± 172 |
| 4 | Example 13 | 5 ± 3 | 196 ± 26 | 121 ± 9 | 1027 ± 81 |
| 4 | Example 14 | 2 ± 1 | 246 ± 32 | 166 ± 33 | 1422 ± 120 |
| 4 | Example 15 | 0 ± 0 | 246 ± 25 | 175 ± 40 | 1257 ± 224 |
| 4 | [1]Vehicle | 0 ± 0 | 155 ± 25 | 117 ± 15 | 30 ± 3 |
| 6 | Example 16 | 0 ± 0 | 110 ± 10 | 160 ± 16 | 457 ± 88 |
| 6 | Example 13 | 2 ± 2 | 151 ± 19 | 137 ± 34 | 574 ± 71 |
| 6 | Example 14 | 1 ± 0 | 191 ± 37 | 188 ± 43 | 1121 ± 213 |
| 6 | Example 15 | 3 ± 3 | 177 ± 24 | 221 ± 27 | 1183 ± 139 |
| 6 | [1]Vehicle | 8 ± 5 | 117 ± 26 | 148 ± 16 | 28 ± 4 |

[1]Vehicle (2.00% carbomer 974, 0.50% hydroxypropyl cellulose, 15.0% propylene glycol, 0.15% methylparaben, 0.03% propylparaben, 0.05% edetate sodium, 0.94% 20% tromethamine solution, and water qs to 100%)

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An aqueous gel comprising:
   water;
   an immune response modifier (IRM);
   a pharmaceutically acceptable acid;
   a water-miscible cosolvent; and
   a thickener system comprising a negatively charged thickener;
   wherein the aqueous gel has a viscosity of at least 1000 cps at 25° C.;
   wherein the IRM is selected from the group consisting of amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and an IRM salt thereof; and
   wherein the aqueous gel does not contain oil.

2. An aqueous gel of claim 1 prepared by a method comprising combining components comprising:
   water;
   the immune response modifier (IRM);
   the water-miscible cosolvent; and
   the thickener system comprising a negatively charged thickener;
   wherein the aqueous gel has a viscosity of at least 1000 cps at 25° C.

3. The aqueous gel of claim 1 wherein the IRM in its free base form has an intrinsic aqueous solubility of less than 500μm at 25° C.

4. The aqueous gel of claim 1 wherein the pharmaceutically acceptable acid is present in a stoichiometric amount relative to the IRM.

5. The aqueous gel of claim 1 wherein the pharmaceutically acceptable acid is selected from the group consisting of an alkylsulfonic acid, an arylsulfonic acid, a carboxylic acid, a halo acid, sulfuric acid, phosphoric acid, a dicarboxylic acid, a tricarboxylic acid, and combinations thereof.

6. The aqueous gel of claim 5 wherein the acid is selected from the group consisting of acetic acid, hydrobromic acid, hydrochloric acid, methanesulfonic acid, ethanesulfonic acid, D-gluconic acid, D- and L-lactic acid, propionic acid, benzenesulfonic acid, citric acid, phosphoric acid, succinic acid, sulfuric acid, D- and L-tartaric acid, p-toluenesulfonic acid, and combinations thereof.

7. The aqueous gel of claim 1 wherein the IRM is a salt of an acid selected from the group consisting of an alkylsulfonic acid, an arylsulfonic acid, a carboxylic acid, a halo acid, sulfuric acid, phosphoric acid, a dicarboxylic acid, a tricarboxylic acid, and combinations thereof.

8. The aqueous gel of claim 7 wherein the IRM salt is a salt of an acid selected from the group consisting of hydrobromic acid, hydrochloric acid, methanesulfonic acid, ethanesulfonic acid, acetic acid, D-gluconic acid, D- and L-lactic acid, propionic acid, benzenesulfonic acid, citric acid, phosphoric acid, succinic acid, sulfuric acid, D- and L-tartaric acid, p-toluenesulfonic acid, and combinations thereof.

9. The aqueous gel of claim 7 wherein the IRM is an alkylsulfonate salt.

10. The aqueous gel of claim 1 wherein the IRM is selected from the group consisting of tetrahydroimidazoquinolines, imidazopyridine amines, 6,7-fused cycloalkylimidazopyridine amines, imidazonaphthyridine amines, tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; 1H-imidazo dimers fused to pyridine amines, quinoline amines, tetrahydroquinoline amines, naphthyridine amines, or tetrahydronaphthyridine amines; and combinations thereof.

11. The aqueous gel of claim 1 wherein the IRM is an amide substituted imidazoquinoline amine.

12. The aqueous gel of claim 11 wherein the IRM is selected from the group consisting of 3-(4-amino-2-propyl-1H-imidazo[4,5-c]quinolin-1-yl)propionamide, N-[2-(4-amino-7-benzyloxy-2-ethoxymethyl-1H-imidazo[4,5-c]quinolin-1-yl)-1,1-dimethylethyl]acetamide, and 4-(4-amino-2-propyl-1H-imidazo[4,5-c]quinolin-1-yl)-N-propylbutyramide.

13. The aqueous gel of claim 1 wherein the IRM is present in an amount of at least 0.0001 wt-%, based on the total weight of the aqueous gel.

14. The aqueous gel of claim 1 wherein the water-miscible cosolvent is present in an amount of at least 10 wt-%, based on the total weight of the aqueous gel.

15. The aqueous gel of claim 1 wherein the water-miscible cosolvent is selected from the group consisting of monopropylene glycol, dipropylene glycol, hexylene glycol, butylene glycol, glycerin, polyethylene glycol, diethylene glycol monoethyl ether, and combinations thereof.

16. The aqueous gel of claim 1 wherein the thickener system is present in an amount of at least 0.1 wt-% and no greater than 7 wt-%, based on the total weight of the aqueous gel.

17. The aqueous gel of claim 1 wherein water is present in an amount of at least 10 wt-%, based on the total weight of the aqueous gel.

18. The aqueous gel of claim 1 having a pH of 2 to 5.

19. A method of delivering an IRM to mucosal tissue of a subject, the method comprising applying the aqueous gel of claim 1 to the mucosal tissue.

20. The method of claim 19 wherein the aqueous gel is applied to the mucosal tissue using a device selected from the group consisting of a barrel type applicator, a tampon, a cervical cap, a diaphragm, a cotton swab, a cotton sponge, a foam sponge, and a suppository.

21. A kit comprising a barrel type applicator and an aqueous gel of claim 1.

22. The aqueous gel of claim 1 wherein the thickener system comprises a non-ionic thickener.

23. The aqueous gel of claim 1 wherein the thickener system comprises a negatively charged thickener.

24. The aqueous gel of claim 1 wherein the thickener system comprises a thickener that is not covalently bound to the IRM.

* * * * *

UNITED STATES PATENT AND TRADEMARK OFFICE
CERTIFICATE OF CORRECTION

Page 1 of 3

PATENT NO. : 10,071,156 B2
APPLICATION NO. : 14/971230
DATED : September 11, 2018
INVENTOR(S) : David Ma It is certified that error appears in the above-identified patent and that said Letters Patent is hereby corrected as shown below:

On the Title Page

Page 6 Column 2 (Other Publications)
Line 57, delete "Suppi" and insert -- Suppl --, therefor.

Page 8 Column 1 (Other Publications)
Line 26, delete "Left." and insert -- Lett. --, therefor.

Page 9 Column 1 (Other Publications)
Line 11, delete ";3(19):" and insert -- ;3(10): --, therefor.
Line 49, delete "lmmunol." and insert -- Immunol. --, therefor.

Page 11 Column 1 (Other Publications)
Line 4, delete ";266:" and insert -- ;26B: --, therefor.

Page 11 Column 2 (Other Publications)
Line 67, delete ";8475:" and insert -- ;S475: --, therefor.

In the Specification

Column 5
Line 10, delete "valcyclovir." and insert -- valacyclovir. --, therefor.

Column 10
Line 46, delete "1,2," and insert -- 1, 2, --, therefor.

Column 16
Line 1, delete "alkyl)$_{0-10}$" and insert -- alkyl)$_{0-1}$ --, therefor.

Signed and Sealed this
Sixteenth Day of April, 2019

Andrei Iancu
*Director of the United States Patent and Trademark Office*

CERTIFICATE OF CORRECTION (continued)

Column 17
Line 37, delete "13 O—haloalkyl;" and insert -- —O—haloalkyl; --, therefor.

Column 24
Line 15-25, delete " " and insert -- 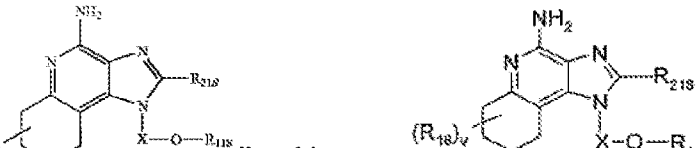 --, therefor.

Column 27
Line 19, delete "—₃;" and insert -- —N₃; --, therefor.
Line 63, delete "-alkyl;" and insert -- -aryl; --, therefor.

Column 31
Line 45, delete "—NR₃₂₆" and insert -- —NR₈₂₆ --, therefor.

Column 34
Line 7, delete "C$_{1-10}$ alkyl;" and insert -- C$_{1-10}$alkyl; --, therefor.

Column 35
Line 62, delete "C$_{1-10}$ alkyl;" and insert -- C$_{1-10}$alkyl; --, therefor.

Column 36
Line 55, delete "(alkyl)$_{0-1}$" and insert -- -(alkyl)$_{0-1}$ --, therefor.

Column 37
Line 44, delete "C$_{1-10}$ alkyl;" and insert -- C$_{1-10}$alkyl; --, therefor.

Column 38
Line 1, delete "—S(O)$_{02}$—;" and insert -- —S(O)$_{0-2}$—; --, therefor.
Line 8 (approx.), delete "—R$_{380}$-" and insert -- —R$_{830}$- --, therefor.
Line 28 (approx.), delete "—SO$_2$—R$_{1030}$;" and insert -- —SO$_2$-NH$_2$; --, therefor.
Line 64, delete "-;" and insert -- -alkyl; --, therefor.

Column 41
Line 15, delete "-norbornen-" and insert -- -norbornene- --, therefor.

Column 47
Line 13, delete "-aminess," and insert -- -amines, --, therefor.
Line 16, delete "aminess" and insert -- amines --, therefor.

Column 48
Line 20 (approx.), delete "N(R$_{933}$)$_2$;" and insert -- —N(R$_{933}$)$_2$; --, therefor.

Column 50
Line 2, delete "-imidaz" and insert -- -imidazo --, therefor.

Column 51
Line 23-26, delete " 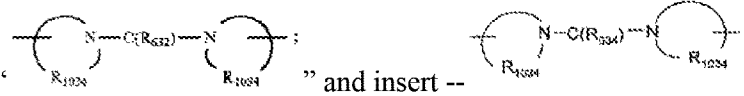 " and insert -- -- ; --, therefor.
Line 67, delete "$C_{3-8}$alkylene;" and insert -- $C_{3-8}$ alkylene; --, therefor.

Column 53
Line 31, delete "arylcarbonylarnino," and insert -- arylcarbonylamino, --, therefor.
Line 32, delete "heteroarylalkycarbonylamino," and insert -- heteroarylalkylcarbonylamino, --, therefor.
Line 47, delete "that" and insert -- than --, therefor.

Column 57
Line 34, delete "ethylenediaminetetracetic" and insert -- ethylenediaminetetraacetic --, therefor.
Line 36, delete "ethylenediaminetetracetic" and insert -- ethylenediaminetetraacetic --, therefor.
Line 38, delete "ethylenediaminetetracetic" and insert -- ethylenediaminetetraacetic --, therefor.

Column 59
Line 29, delete "Papanicoulaou" and insert -- Papanicolaou --, therefor.
Line 60, delete "epidemilogic" and insert -- epidemiologic --, therefor.

Column 61 (TABLE 1 continued)
Line 13 (approx.), delete "-buytl-" and insert -- -butyl- --, therefor.

In the Claims

Column 69
Line 35, in Claim 3, delete "500μm" and insert -- 500 μg --, therefor.